(12) United States Patent
Thorpe et al.

(10) Patent No.: US 6,406,693 B1
(45) Date of Patent: Jun. 18, 2002

(54) CANCER TREATMENT METHODS USING ANTIBODIES TO AMINOPHOSPHOLIPIDS

(75) Inventors: Philip E. Thorpe; Sophia Ran, both of Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/351,543

(22) Filed: Jul. 12, 1999

Related U.S. Application Data

(60) Provisional application No. 60/110,608, filed on Dec. 2, 1998, and provisional application No. 60/092,672, filed on Jul. 13, 1998.

(51) Int. Cl.[7] ...................... A61K 39/395; C07K 16/00; C07K 16/28; C07K 16/30; C12Q 1/68
(52) U.S. Cl. .................. 424/130.1; 424/132.1; 424/133.1; 424/135.1; 424/138.1; 424/141.1; 424/152.1; 424/184.1; 530/387.1; 435/6
(58) Field of Search ...................... 424/130.1, 184.1, 424/132.1, 133.1, 135.1, 138.1, 141.1, 152.1; 530/387.1; 435/6

(56) References Cited

U.S. PATENT DOCUMENTS

| | | | |
|---|---|---|---|
| 5,296,467 A | 3/1994 | Reutelingsperger | 514/12 |
| 5,344,758 A | 9/1994 | Krilis et al. | 433/4.1 |
| 5,627,036 A | 5/1997 | Reutelingsperger | 435/7.21 |
| 5,632,986 A | 5/1997 | Tait et al. | 424/94.64 |
| 5,632,991 A | 5/1997 | Gimbrone, Jr. | 424/178.1 |
| 5,658,877 A | 8/1997 | Tsao | 514/2 |
| 5,660,827 A | 8/1997 | Thorpe et al. | 424/152.1 |
| 5,757,298 A | 6/1998 | Daleke | 554/80 |
| 5,776,427 A | 7/1998 | Thorpe et al. | 424/1.49 |
| 5,855,866 A | 1/1999 | Thorpe et al. | 424/1.49 |
| 5,863,538 A | 1/1999 | Thorpe et al. | 424/136.1 |
| 5,877,289 A | 3/1999 | Thorpe et al. | 530/387.1 |
| 5,965,132 A | 10/1999 | Thorpe et al. | 424/149 |
| 6,004,554 A | 12/1999 | Thorpe et al. | 424/178.1 |
| 6,004,555 A | 12/1999 | Thorpe et al. | 424/181.1 |
| 6,036,955 A | 3/2000 | Thorpe et al. | 424/136.1 |
| 6,043,094 A | 3/2000 | Martin et al. | 435/458 |
| 6,051,230 A | 4/2000 | Thorpe et al. | 424/178.1 |
| 6,057,435 A | 5/2000 | Godowski et al. | 536/23.5 |
| 6,093,399 A | 7/2000 | Thorpe et al. | 424/182 |
| 6,197,278 B1 | 3/2001 | Blankenberg et al. | 424/1.69 |

FOREIGN PATENT DOCUMENTS

| | | |
|---|---|---|
| WO | WO 91/07187 | 5/1991 |
| WO | WO 93/17715 | 9/1993 |
| WO | WO 95/19791 | 7/1995 |
| WO | WO 95/27903 | 10/1995 |
| WO | WO 95/34315 | 12/1995 |
| WO | WO 96/01653 | 1/1996 |
| WO | WO 96/17618 | 6/1996 |
| WO | WO 97/17084 | 5/1997 |
| WO | WO 98/04294 | 2/1998 |
| WO | WO 98/29453 | 7/1998 |
| WO | WO98/43678 | 10/1998 |

OTHER PUBLICATIONS

Ferro et al., "Coexistence of Anti–Phospholipid Antibodies and Endothelial Perturbation in Systemic Lupus Erythematosus Patients with Ongoing Prothrombotic State," *Circulation*, 95(6);1425–1432, 1997.

Fishman et al., "Autoimmunity and Cancer—Beneficial Relationships: a new Concept for the Production of Human Monoclonal Antibodies (Review)," *International Journal of Oncology*, 10:901–904, 1997.

Tobelem, "Les Anticorps Antiphospholipides: Specificite et Mechanisme d'Action," *Ann. Med. Interne*, 141:257–260, 1990.

International Search Report for PCT/US99/15600, mailed Jan. 26, 2000.

Maisonpierre et al., "Angiopoietin–2, a Natural Antagonist for Tie2 that Disrupts In Vivo Angiogenesis," *Research Articles*, 277:55–60, 1997.

International Search Report for PCT/US00/18779, mailed Oct. 4, 2000.

Co–pending Application Ser. No. 09/351,149; Entitled: "Cancer Treatment Using Angiopoietins Targeted to Aminophospholipids," filed Jul. 10, 2000 (Attorney Docket No. 3999.002600; formerly UTSD:556–3).

Skolnick and Fetrow, "From genes to protein structure and function: novel applications of computational approaches in the genomic era," *Trends in Biotech*, 2000.

Diaz et al.; "Synthesis of Disulfide–Containing Phospholipid Analogs for the Preparation of Head Group–Specific Lipid Antigens: Generation of Phosphatidylserine Antibodies;" *Bioconjugate Chem.*; 9:250–254, 1998.

Kasina et al.; "Preformed Chelate TC–99m Radiolabeling of r–Annexin V for Arterial Thrombus Imaging;" *Nucl. Med.*; vol. 37, No. 5, 29P.

Rauch and Janoff; "Antibodies Against Phospholipids Other than Cardiolipin: Potential Roles for Both Phospholipid and Protein;" *Lupus*; 5:498–502, 1996.

(List continued on next page.)

*Primary Examiner*—Geetha P. Bansal
(74) *Attorney, Agent, or Firm*—Williams, Morgan and Amerson

(57) ABSTRACT

Disclosed are the surprising discoveries that aminophospholipids, such as phosphatidylserine and phosphatidylethanolamine, are stable and specific markers accessible on the luminal surface of tumor blood vessels, and that the administration of an anti-aminophospholipid antibody alone is sufficient to induce thrombosis, tumor necrosis and tumor regression in vivo. This invention therefore provides anti-aminophospholipid antibody-based methods and compositions for use in the specific destruction of tumor blood vessels and in the treatment of solid tumors. Although various antibody conjugates and combinations are thus provided, the use of naked, or unconjugated, anti-phosphatidylserine antibodies is a particularly important aspect of the invention, due to simplicity and effectiveness of the approach.

63 Claims, 3 Drawing Sheets

OTHER PUBLICATIONS

Sarrot–Reynauld and Massot; "Antiphospholipid Antibodies Paraneoplastic Syndrome Revealing Prostatic Cancer;" ; *Lupus*; vol. 5, No. 5, pp 528, 1996.

Thorpe et al.; "Tumor Infarction: Immunoconjugates that Coagulate the Vasculature of Solid Tumors;" *Proceedings of the Annual Meeting of the American Association for Cancer Research*; 36:488, 1995.

van Heerde et al.; "Binding of Recombinant Annexin V to endothelial Cells: Effect of Annexin V Binding on Endothelial–Cell–Mediated Thrombine Formation;" *Biochem.*; 302:305–312, 1994.

International Search Report for PCT/US99/15668, mailed Dec. 29, 1999.

Blankenberg et al., "In vivo Detection and Imaging of Phosphatidylserine Expression During Programmed Cell Death," *Proc. Natl. Acad. Sci. USA*, 95:6349–6354, 1998.

Bombeli et al., "Apoptotic Vascular Endothelial Cells Become Procoagulant," *Blood*, 89:2429–2442, 1997.

Bordron et al., "The Binding of some Human Antiendothelial Cell Antibodies Induces Endothelial Cell Apoptosis," *J. Clin. Invest.*, 101:2029–2035, 1998.

Burrows et al., "A Murine Model for Antibody–Directed Targeting of Vascular Endothelial Cells in Solid Tumors," *Cancer Research*, 52:5954–5962, 1992.

Burrows and Thorpe, "Eradication of Large Solid Tumors in Mice with an Immunotoxin Directed Against Tumor Vasculature," *Proc. Natl. Acad. Sci. USA*, 90:8996–9000, 1993.

Connor et al., "Differentiation–Dependent Expression of Phosphatidylserine in Mammalian Plasma Membranes: Quantitative Assessment of Outer–Leaflet Lipid by Prothrombinase Complex Formation," *Proc. Natl. Acad. Sci. USA*, 86:3184–3188, 1989.

de Jong et al., "Oxidative Damage Does Not Alter Membrane Phospholipid Asymmetry in Human Erythrocytes," *Biochemistry*, 36:6768–6776, 1997.

Denekamp, "Vascular Attack as a Therapeutic Strategy for Cancer," *Cancer and Metastasis Reviews*, 9:267–282, 1990.

Dvorak et al., "Structure of Solid Tumors and Their Vasculature: Implications for Therapy with Monoclonal Antibodies," *Cancer Cells*, vol. 3, No. 3, 1991.

Gaffet et al., "Transverse Redistribution of Phospholipids During Human Platelet Activation: Evidence for a Vectorial Outflux Specific to Aminophospholipids," *Biochemistry*, 34:6762–6769, 1995.

Hagemeier et al., "A Monoclonal Antibody Reacting with Endothelial Cells of Budding Vessels in Tumors and Inflammatory Tissues, and Non–Reactive with Normal Adult Tissues," *Int. J. Cancer*, 38:481–488, 1986.

Huang et al., "Tumor Infarction in Mice by Antibody–Directed Targeting of Tissue Factor to Tumor Vasculature," *Science*, 275:547–550, 1997.

Igarashi et al., "Effective Induction of Anti–Phospholipid and Anticoagualant Antibodies in Normal Mouse," *Thrombosis Research*, 61:135–148, 1991.

Jamasbi et al., "Epitope Masking of Rat Esophageal Carcinoma Tumor–Associated Antigen by Certain Coexisting Glycolipid and Phospholipid Molecules: A Potential Mechanism for Tumor Cell Escape form the Host Immune Responses," *Cancer Immunol. Immunother.*, 38:99–106, 1994.

Julien et al., "Differences in the Transbilayer and Lateral Motions of Fluorescent Analogs of Phosphatidylcholine and Phosphatidylethanolamine in the Apical Plasma Membrane of Bovine Aortic Endothelial Cells," *Experimental Cell Research*, 208:387–397, 1993.

Julien et al., "Basic Fibroblast Growth Factor Modulates the Aminophospholipid Translocase Activity Present in the Plasma Membrane of Bovine Aortic Endothelial Cells," *Eur. J. Biochem.*, 230:287–297, 1995.

Maneta–Peyret et al., "Demonstration of High Specificity Antibodies Against Phosphatidylserine," *J. Immunol. Methods*, 108:123–127, 1988.

Martin et al., "Early Redistribution of Plasma Membrane Phosphatidylserine is a General Feature of Apoptosis Regardless of the Initiating Stimulus: Inhibition by Overexpression of Bcl–2 and Abl," *J. Exp. Med.*, 182:1545–1556, 1995.

Moldavan et al., "Binding of Vascular Anticoagulant Alpha (Annexin V) to the Aortic Intima of the Hypercholesterolemic Rabbit. An Autoradiographic Study," *Blood Coagulation and Fibrinolysis*, 5:921–928, 1994.

Ohizumi et al., "Antibody–Based Therapy Targeting Tumor Vascular Endothelial Cells Suppresses Solid Tumor Growth in Rats," *Biochem. Biophys. Res. Comm.*, 236:493–496, 1997.

Qu et al., "Phosphatidylserine–Mediated Adhesion of T–Cells to Endothelial Cells," *Biochem. J.*, 317:343–346, 1996.

Ran et al., "Infarction of Solid Hodgkin's Tumors in Mice by Antibody–Directed Targeting of Tissue Factor to Tumor Vasculature," *Cancer Res.*, 58:4646–4653, 1998.

Rauch and Janoff, "Phospholipid in the Hexagonal II Phase is Immunogenic: Evidence for Immunorecognition of Nonbilayer Lipid Phases in vivo," *Proc. Natl. Acad. Sci. USA*, 87:4112–4114, 1990.

Rote et al., "Immunologic Detection of Phosphatidylserine Externalization During Thrombin–Induced Platelet Activation," *Clinical Immunology and Immunopathology*, 66:193–200, 1993.

Rote, "Antiphospholipid Antibodies and Recurrent Pregnancy Loss," *AJRI*, 35:394–401, 1996.

Ruf and Edgington, "Structural Biology of Tissue Factor, the Initiator of Thrombogenesis in vivo," *FASEB J.*, 8:385–390, 1994.

Sugi and McIntyre, "Phosphatidylethanolamine Induces Specific Conformational Changes in the Kininogens Recognizable by Antiophosphatidylethanolamine Antibodies," *Thromosis and Haemostasis*, 76:354–360, 1996.

Takagaki et al., "Cloning and Sequence Analysis of cDNAs for Human High Molecular Weight and Low Molecular Weight Prekininogens," *J. Biol. Chem.*, 260:8601–8609, 1985.

Umeda et al., "Effective Production of Monoclonal Antibodies Against Phosphatidylserine: Stereo–Specific Recognition of Phosphatidylserine by Monoclonal Antibody," *J. Immunol.*, 143:2273–2279, 1989.

Utsugi et al., "Elevated Expression of Phosphatidylserine in the Outer Membrane Leaflet of Human Tumor Cells and Recognition by Activated Human Blood Monocytes," *Cancer Research*, 51:3062–3066, 1991.

Williamson and Schlegel, "Back and Forth: the Regulation and Function of Transbilayer Phospholipid Movement in Eukaryotic Cells (Review)," *Molecular Membrane Biology*, 11:199–216, 1994.

Zhao et al., "Level of Expression of Phospholipid Scramblase Regulates Induced Movement of Phosphatidylserine to the Cell Surface," *J. Biol. Chem.*, 273:6603–6606, 1998.

Zhou et al., "Molecular Cloning of Human Plasma Membrane Phospholipid Scramblase," *J. Biol. Chem.*, 272:18240–18244, 1997.

Co–pending Application Ser. No. 09/351,862; Entitled: "Cancer Treatment Kits Using Antibodies to Aminophospholipids"; filed Jul. 12, 1999 (Attorney Docket Nos. 4001.002282, UTSD:549–1).

Co–pending Application Ser. No. 09/351,457; Entitled: "Cancer Treatment Methods Using Therapeutic Conjugates that Bind to Aminophospholipids"; filed Jul. 12, 1999 (Attorney Docket Nos. 4001.002300, USTD:556).

Co–pending Application Ser. No. 09/351,598; Entitled: "Cancer Treatment Compositions Comprising Therapeutic Conjugates that Bind to Aminophospholipids"; filed Jul. 12, 1999 (Attorney Docket Nos. 4001.002382, USTD:556–1).

Co–pending Application Ser. No. 09/351,149; Entitled: "Cancer Treatment Kits Comprising Therapeutic Conjugates that Bind to Aminophospholipids"; filed Jul. 12, 1999 (Attorney Docket Nos. 4001.002383, UTSD:556–2).

SEQUENCE LISTING

<160> NUMBER OF SEQ ID NOS: 5

<210> SEQ ID NO 1
<211> LENGTH: 2149
<212> TYPE: DNA
<213> ORGANISM: Homo sapiens

<400> SEQUENCE: 1

```
cagctgactc aggcaggctc catgctgaac ggtcacacag agaggaaaca ataaatctca      60
gctactatgc aataaatatc tcaagtttta acgaagaaaa acatcattgc agtgaaataa     120
aaaattttaa aattttagaa caaagctaac aaatggctag ttttctatga ttcttcttca     180
aacgctttct ttgaggggga aagagtcaaa caaacaagca gttttacctg aaataaagaa     240
ctagttttag aggtcagaag aaaggagcaa gttttgcgag aggcacggaa ggagtgtgct     300
ggcagtacaa tgacagtttt cctttccttt gctttcctcg ctgccattct gactcacata     360
gggtgcagca atcagcgccg aagtccagaa aacagtggga gaagatataa ccggattcaa     420
catgggcaat gtgcctacac tttcattctt ccagaacacg atggcaactg tcgtgagagt     480
acgacagacc agtacaacac aaacgctctg cagagagatg ctccacacgt ggaaccggat     540
ttctcttccc agaaacttca acatctggaa catgtgatgg aaaattatac tcagtggctg     600
caaaaacttg agaattacat tgtggaaaac atgaagtcgg agatggccca gatacagcag     660
aatgcagttc agaaccacac ggctaccatg ctggagatag aaccagcct cctctctcag     720 actgcagagc agaccagaaa gctgacagat gttgagaccc aggtactaaa tcaaacttct     780
cgacttgaga tacagctgct ggagaattca ttatccacct acaagctaga gaagcaactt     840
cttcaacaga caaatgaaat cttgaagatc catgaaaaaa acagtttatt agaacataaa     900
atcttagaaa tggaaggaaa acacaaggaa gagttggaca ccttaaagga agagaaagag     960
aaccttcaag gcttggttac tcgtcaaaca tatataatcc aggagctgga aaagcaatta    1020
aacagagcta ccaccaacaa cagtgtcctt cagaagcagc aactggagct gatggacaca    1080
gtccacaacc ttgtcaatct ttgcactaaa gaaggtgttt tactaaaggg aggaaaaaga    1140
gaggaagaga aaccatttag agactgtgca gatgtatatc aagctggttt taataaaagt    1200
ggaatctaca ctatttatat taataatatg ccagaaccca aaaaggtgtt ttgcaatatg    1260
gatgtcaatg ggggaggttg gactgtaata caacatcgtg aagatggaag tctagatttc    1320
caaagaggct ggaaggaata taaaatgggt tttggaaatc cctccggtga atattggctg    1380
gggaatgagt ttatttttgc cattaccagt cagaggcagt acatgctaag aattgagtta    1440
atggactggg aagggaaccg agcctattca cagtatgaca gattccacat aggaaatgaa    1500
aagcaaaact ataggttgta tttaaaaggt cacactggga cagcaggaaa acagagcagc    1560
```

-continued

```
ctgatcttac acggtgctga tttcagcact aaagatgctg ataatgacaa ctgtatgtgc    1620
aaatgtgccc tcatgttaac aggaggatgg tggtttgatg cttgtggccc ctccaatcta    1680
aatggaatgt tctatactgc gggacaaaac catggaaaac tgaatgggat aaagtggcac    1740
tacttcaaag ggcccagtta ctccttacgt tccacaacta tgatgattcg accctttagat   1800 ttttgaaagc gcaatgtcag aagcgattat gaaagcaaca aagaaatccg agaagctgc     1860 caggtgagaa actgtttgaa aacttcagaa gcaaacaata ttgtctccct tccagcaata    1920
agtggtagtt atgtgaagtc accaaggttc ttgaccgtga atctggagcc gtttgagttc    1980
acaagagtct ctacttgggg tgacagtgct cacgtggctc gactatagaa aactccactg    2040
actgtcgggc tttaaaaagg gaagaaactg ctgagcttgc tgtgcttcaa actactactg    2100
gaccttattt tggaactatg gtagccagat gataaatatg gttaatttc                2149
```

<210> SEQ ID NO 2
<211> LENGTH: 498
<212> TYPE: PRT
<213> ORGANISM: Homo sapiens

<400> SEQUENCE: 2

```
Met Thr Val Phe Leu Ser Phe Ala Phe Leu Ala Ala Ile Leu Thr His
  1               5                  10                  15

Ile Gly Cys Ser Asn Gln Arg Arg Ser Pro Glu Asn Ser Gly Arg Arg
             20                  25                  30

Tyr Asn Arg Ile Gln His Gly Gln Cys Ala Tyr Thr Phe Ile Leu Pro
         35                  40                  45

Glu His Asp Gly Asn Cys Arg Glu Ser Thr Thr Asp Gln Tyr Asn Thr
     50                  55                  60

Asn Ala Leu Gln Arg Asp Ala Pro His Val Glu Pro Asp Phe Ser Ser
 65                  70                  75                  80

Gln Lys Leu Gln His Leu Glu His Val Met Glu Asn Tyr Thr Gln Trp
                 85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
        195                 200                 205

Leu Asp Thr Leu Lys Glu Glu Lys Glu Asn Leu Gln Gly Leu Val Thr
    210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Gly Val Leu Leu
            260                 265                 270
```

```
Lys Gly Gly Lys Arg Glu Glu Lys Pro Phe Arg Asp Cys Ala Asp
            275                 280                 285

Val Tyr Gln Ala Gly Phe Asn Lys Ser Gly Ile Tyr Thr Ile Tyr Ile
        290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
                325                 330                 335

Phe Gln Arg Gly Trp Lys Glu Tyr Lys Met Gly Phe Gly Asn Pro Ser
            340                 345                 350

Gly Glu Tyr Trp Leu Gly Asn Glu Phe Ile Phe Ala Ile Thr Ser Gln
        355                 360                 365

Arg Gln Tyr Met Leu Arg Ile Glu Leu Met Asp Trp Glu Gly Asn Arg
    370                 375                 380

Ala Tyr Ser Gln Tyr Asp Arg Phe His Ile Gly Asn Glu Lys Gln Asn
385                 390                 395                 400

Tyr Arg Leu Tyr Leu Lys Gly His Thr Gly Thr Ala Gly Lys Gln Ser
                405                 410                 415

Ser Leu Ile Leu His Gly Ala Asp Phe Ser Thr Lys Asp Ala Asp Asn
            420                 425                 430

Asp Asn Cys Met Cys Lys Cys Ala Leu Met Leu Thr Gly Gly Trp Trp
        435                 440                 445

Phe Asp Ala Cys Gly Pro Ser Asn Leu Asn Gly Met Phe Tyr Thr Ala
    450                 455                 460

Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495

Asp Phe

<210> SEQ ID NO 3
<211> LENGTH: 2269
<212> TYPE: DNA
<213> ORGANISM: Homo sapiens

<400> SEQUENCE: 3
tgggttggtg tttatctcct cccagccttg agggagggaa caacactgta ggatctgggg      60
agagaggaac aaaggaccgt gaaagctgct ctgtaaaagc tgacacagcc ctcccaagtg     120
agcaggactg ttcttcccac tgcaatctga cagtttactg catgcctgga gagaacacag     180
cagtaaaaac caggtttgct actggaaaaa gaggaaagaa aagactttca ttgacggacc     240
cagccatggc agcgtagcag ccctgcgttt cagacggcag cagctcggga ctctggacgt     300
gtgtttgccc tcaagtttgc taagctgctg gtttattact gaagaaagaa tgtggcagat     360
tgttttcttt actctgagct gtgatcttgt cttggccgca gcctataaca actttcggaa     420
gagcatggac agcataggaa agaagcaata tcaggtccag catgggtcct gcagctacac     480
tttcctcctg ccagagatgg acaactgccg ctcttcctcc agcccctacg tgtccaatgc     540
tgtgcagagg gacgcgccgc tcgaatacga tgactcggtg cagaggctgc aagtgctgga     600
gaacatcatg gaaacaacaa ctcagtggct aatgaagctt gagaattata tccaggacaa     660
catgaagaaa gaaatggtag agatacagca gaatgcagta cagaaccaga cggctgtgat     720
gatagaaata gggacaaacc tgttgaacca aacagctgag caaacgcgga gttaactga      780 tgtggaagcc caagtattaa atcagaccac gagacttgaa cttcagctct tggaacactc     840
```

-continued

```
cctctcgaca aacaaattgg aaaaacagat tttggaccag accagtgaaa taaacaaatt   900
gcaagataag aacagtttcc tagaaaagaa ggtgctagct atggaagaca agcacatcat   960
ccaactacag tcaataaaag aagagaaaga tcagctacag tgttagtat ccaagcaaaa   1020 ttccatcatt gaagaactag aaaaaaaaat agtgactgcc acggtgaata attcagttct   1080
tcaaaagcag caacatgatc tcatggagac agttaataac ttactgacta tgatgtccac   1140
atcaaactca gctaaggacc ccactgttgc taaagaagaa caaatcagct tcagagactg   1200
tgctgaagta ttcaaatcag gacacaccac aaatggcatc tacacgttaa cattccctaa   1260
ttctacagaa gagatcaagg cctactgtga catggaagct ggaggaggcg ggtggacaat   1320
tattcagcga cgtgaggatg gcagcgttga ttttcagagg acttggaaag aatataaagt   1380
gggatttggt aacccttcag gagaatattg gctgggaaat gagtttgttt cgcaactgac   1440
taatcagcaa cgctatgtgc ttaaaataca ccttaaagac tgggaaggga atgaggctta   1500
ctcattgtat gaacatttct atctctcaag tgaagaactc aattatagga ttcaccttaa   1560
aggacttaca gggacagccg gcaaaataag cagcatcagc caaccaggaa atgattttag   1620
cacaaaggat ggagacaacg acaaatgtat ttgcaaatgt tcacaaatgc taacaggagg   1680
ctggtggttt gatgcatgtg gtccttccaa cttgaacgga atgtactatc cacagaggca   1740
gaacacaaat aagttcaacg gcattaaatg gtactactgg aaaggctcag gctattcgct   1800
caaggccaca accatgatga tccgaccagc agatttctaa acatcccagt ccacctgagg   1860
aactgtctcg aactattttc aaagacttaa gcccagtgca ctgaaagtca cggctgcgca   1920
ctgtgtcctc ttccaccaca gagggcgtgt gctcggtgct gacgggaccc acatgctcca   1980
gattagagcc tgtaaacttt atcacttaaa cttgcatcac ttaacggacc aaagcaagac   2040
cctaaacatc cataattgtg attagacaga acacctatgc aaagatgaac ccgaggctga   2100
gaatcagact gacagtttac agacgctgct gtcacaacca agaatgttat gtgcaagttt   2160
atcagtaaat aactggaaaa cagaacactt atgttataca atacagatca tcttggaact   2220
gcattcttct gagcactgtt tatacactgt gtaaatacc atatgtcct   2269
```

<210> SEQ ID NO 4
<211> LENGTH: 496
<212> TYPE: PRT
<213> ORGANISM: Homo sapiens

<400> SEQUENCE: 4

```
Met Trp Gln Ile Val Phe Phe Thr Leu Ser Cys Asp Leu Val Leu Ala
  1               5                  10                  15

Ala Ala Tyr Asn Asn Phe Arg Lys Ser Met Asp Ser Ile Gly Lys Lys
             20                  25                  30

Gln Tyr Gln Val Gln His Gly Ser Cys Ser Tyr Thr Phe Leu Leu Pro
         35                  40                  45

Glu Met Asp Asn Cys Arg Ser Ser Ser Pro Tyr Val Ser Asn Ala
     50                  55                  60

Val Gln Arg Asp Ala Pro Leu Glu Tyr Asp Ser Val Gln Arg Leu
 65                  70                  75                  80

Gln Val Leu Glu Asn Ile Met Glu Asn Thr Gln Trp Leu Met Lys
                 85                  90                  95

Leu Glu Asn Tyr Ile Gln Asp Asn Met Lys Lys Glu Val Glu Ile
                100                 105                 110

Gln Gln Asn Ala Val Gln Asn Gln Thr Ala Val Met Ile Glu Ile Gly
            115                 120                 125
```

```
Thr Asn Leu Leu Asn Gln Thr Ala Glu Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
    210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
        275                 280                 285

Lys Ser Gly His Thr Thr Asn Gly Ile Tyr Thr Leu Thr Phe Pro Asn
    290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
        355                 360                 365

Tyr Val Leu Lys Ile His Leu Lys Asp Trp Glu Gly Asn Glu Ala Tyr
    370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
        435                 440                 445

Ala Cys Gly Pro Ser Asn Leu Asn Gly Met Tyr Tyr Pro Gln Arg Gln
    450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495

<210> SEQ ID NO 5
<211> LENGTH: 495
<212> TYPE: PRT
<213> ORGANISM: Homo sapiens

<400> SEQUENCE: 5

Met Trp Gln Ile Val Phe Phe Thr Leu Ser Cys Asp Leu Val Leu Ala
  1               5                  10                  15
```

-continued

```
Ala Ala Tyr Asn Asn Phe Arg Lys Ser Met Asp Ser Ile Gly Lys Lys
             20                  25                  30

Gln Tyr Gln Val Gln His Gly Ser Cys Ser Tyr Thr Phe Leu Leu Pro
         35                  40                  45

Glu Met Asp Asn Cys Arg Ser Ser Ser Pro Tyr Val Ser Asn Ala
     50                  55                  60

Val Gln Arg Asp Ala Pro Leu Glu Tyr Asp Phe Ser Ser Gln Lys Leu
 65                  70                  75                  80

Gln His Leu Glu His Val Met Glu Asn Tyr Thr Gln Trp Leu Gln Lys
                 85                  90                  95

Leu Glu Asn Tyr Ile Val Glu Asn Met Lys Ser Glu Met Ala Gln Ile
             100                 105                 110

Gln Gln Asn Ala Val Gln Asn His Thr Ala Thr Met Leu Glu Ile Gly
         115                 120                 125

Thr Ser Leu Leu Ser Gln Thr Ala Glu Gln Thr Arg Lys Leu Thr Asp
         130                 135                 140

Val Glu Thr Gln Val Leu Asn Gln Thr Ser Arg Leu Glu Ile Gln Leu
145                 150                 155                 160

Leu Glu Asn Ser Leu Ser Thr Tyr Lys Leu Glu Lys Gln Leu Leu Gln
                 165                 170                 175

Gln Thr Asn Glu Ile Leu Lys Ile His Glu Lys Asn Ser Leu Leu Glu
             180                 185                 190

His Lys Ile Leu Glu Met Glu Gly Lys His Lys Glu Glu Leu Asp Thr
         195                 200                 205

Leu Lys Glu Glu Lys Glu Asn Leu Gln Gly Leu Val Thr Arg Gln Thr
     210                 215                 220

Tyr Ile Ile Gln Glu Leu Glu Lys Gln Leu Asn Arg Ala Thr Thr Asn
225                 230                 235                 240

Asn Ser Val Leu Gln Lys Gln Leu Glu Leu Met Asp Thr Val His
                 245                 250                 255

Asn Leu Val Asn Leu Ser Thr Lys Glu Gly Val Leu Leu Lys Gly Gly
             260                 265                 270

Lys Arg Glu Glu Lys Pro Phe Arg Asp Cys Ala Asp Val Tyr Gln
         275                 280                 285

Ala Gly Phe Asn Lys Ser Gly Ile Tyr Thr Ile Tyr Ile Asn Asn Met
     290                 295                 300

Pro Glu Pro Lys Lys Val Phe Cys Asn Met Asp Val Asn Gly Gly Gly
305                 310                 315                 320

Trp Thr Val Ile Gln His Arg Glu Asp Gly Ser Leu Asp Phe Gln Arg
                 325                 330                 335

Gly Trp Lys Glu Tyr Lys Met Gly Phe Gly Asn Pro Ser Gly Glu Tyr
             340                 345                 350

Trp Leu Gly Asn Glu Phe Ile Phe Ala Ile Thr Ser Gln Arg Gln Tyr
         355                 360                 365

Met Leu Arg Ile Glu Leu Met Asp Trp Glu Gly Asn Arg Ala Tyr Ser
     370                 375                 380

Gln Tyr Asp Arg Phe His Ile Gly Asn Glu Lys Gln Asn Tyr Arg Leu
385                 390                 395                 400

Tyr Leu Lys Gly His Thr Gly Thr Ala Gly Lys Gln Ser Ser Leu Ile
                 405                 410                 415

Leu His Gly Ala Asp Phe Ser Thr Lys Asp Ala Asp Asn Asp Asn Cys
             420                 425                 430
```

-continued

```
Met Cys Lys Cys Ala Leu Met Leu Thr Gly Gly Trp Trp Phe Asp Ala
        435                 440                 445

Cys Gly Pro Ser Asn Leu Asn Gly Met Phe Tyr Thr Ala Gly Gln Asn
        450                 455                 460

His Gly Lys Leu Asn Gly Ile Lys Trp His Tyr Phe Lys Gly Pro Ser
465                 470                 475                 480

Tyr Ser Leu Arg Ser Thr Thr Met Met Ile Arg Pro Leu Asp Phe
                485                 490                 495
```

CANCER TREATMENT METHODS USING ANTIBODIES TO AMINOPHOSPHOLIPIDS

The present application claims priority to first provisional application Ser. No. 60/092,672, filed Jul. 13, 1998, and second provisional application Ser. No. 60/110,608, filed Dec. 2, 1998, the entire text and figures of which applications are incorporated herein by reference without disclaimer.

The U.S. Government owns rights in the present invention pursuant to grant numbers 1RO1CA74951-01 and 5RO1CA54168-05 from the National Institutes of Health.

BACKGROUND OF THE INVENTION

1. Field of the Invention

The present invention relates generally to the fields of blood vessels and tumor biology. More particularly, it embodies the surprising findings that aminophospholipids, such as phosphatidylserine and phosphatidylethanolamine, are specific and stable markers of tumor blood vessels and that administration of anti-aminophospholipid antibodies alone is sufficient to induce thrombosis and tumor regression. The invention thus provides safe and effective methods and compositions for the specific targeting and destruction of tumor blood vessels and for the treatment of solid tumors. The use of unconjugated anti-phosphatidylserine antibodies is a particular advantage, although the invention provides various effective compositions and combinations thereof.

2. Description of the Related Art

Tumor cell resistance to chemotherapeutic agents represents a significant problem in clinical oncology. In fact, this is one of the main reasons why many of the most prevalent forms of human cancer still resist effective chemotherapeutic intervention, despite certain advances in the field of chemotherapy.

A significant problem to address in tumor treatment regimens is the desire for a "total cell kill". This means that the more effective treatment regimens come closer to a total cell kill of all so-called "clonogenic" malignant cells, i.e., cells that have the ability to grow uncontrolled and replace any tumor mass that might be removed by the therapy. Due to the goal of developing treatments that approach a total cell kill, certain types of tumors have been more amenable to therapy than others. For example, the soft tissue tumors, e.g., lymphomas, and tumors of the blood and blood-forming organs, e.g., leukemias, have generally been more responsive to chemotherapeutic therapy than have solid tumors, such as carcinomas.

One reason for the susceptibility of soft and blood-based tumors to chemotherapy is the greater accessibility of lymphoma and leukemic cells to chemotherapeutic intervention. Simply put, it is much more difficult for most chemotherapeutic agents to reach all of the cells of a solid tumor mass than it is the soft tumors and blood-based tumors, and therefore much more difficult to achieve a total cell kill. Increasing the dose of chemotherapeutic agents most often results in toxic side effects, which generally limits the effectiveness of conventional anti-tumor agents.

Another tumor treatment strategy is the use of an "immunotoxin", in which an anti-tumor cell antibody is used to deliver a toxin to the tumor cells. However, in common with the chemotherapeutic approaches described above, immunotoxin therapy also suffers from significant drawbacks. For example, antigen-negative or antigen-deficient cells can survive and repopulate the tumor or lead to further metastases. Also, in the treatment of solid tumors, the tumor mass is generally impermeable to molecules of the size of antibodies and immunotoxins. Both the physical diffusion distances and the interstitial pressure within the tumor are significant limitations to this type of therapy.

A more recent strategy has been to target the vasculature of solid tumors. Targeting the blood vessels of the tumors, rather than the tumor cells themselves, has certain advantages in that it is not likely to lead to the development of resistant tumor cells, and that the targeted cells are readily accessible. Moreover, destruction of the blood vessels leads to an amplification of the anti-tumor effect, as many tumor cells rely on a single vessel for their oxygen and nutrients (Denekamp, 1990). Effective vascular targeting strategies are described in U.S. Pat. Nos. 5,855,866 and 5,965,132 which particularly describe the targeted delivery of anti-cellular agents and toxins to tumor vasculature.

Another effective version of the vascular targeting approach is to target a coagulation factor to tumor vasculature (Huang et al., 1997; U.S. Pat. Nos. 5,877,289, 6,004,555, 6,093,399. The use of antibodies and other targeting agents to deliver coagulants to tumor vasculature has the further advantages of reduced immunogenicity and even lower risk of toxic side effects. As disclosed in U.S. Pat. No. 5,877,289, a preferred coagulation factor for use in such tumor-specific thrombogens, or "coaguligands", is a truncated version of the human coagulation-inducing protein, Tissue Factor (TF). TF is the major initiator of blood coagulation (Ruf et al., 1991; Edgington et al., 1991; Ruf and Edgington, 1994). Treatment of tumor-bearing mice with such coaguligands results in significant tumor necrosis and even complete tumor regression in many animals (Huang et al., 1997; U.S. Pat. Nos. 5,877,289, 6,004,555 and 6,093,399).

Although the specific delivery of therapeutic agents, such as anti-cellular agents, toxins and coagulation factors, to tumor vessels represents a significant advance in tumor treatment protocols, there is still room for additional or even alternative vascular targeting therapies. The identification of additional targets to allow specific tumor vessel destruction in vivo would naturally be of benefit in expanding the number of targeting options. More particularly, as the previously described vascular targeting constructs and coaguligands are two-component systems, involving the targeting agent and the effector portion, the development of a one component agent for tumor vasculature destruction would represent a major advance. Should the preparation of this type of agent prove possible, this would also likely speed the progress of anti-vascular therapy to the clinic, given the simplicity of the new therapeutic agent.

SUMMARY OF THE INVENTION

The present invention addresses the needs of the prior art by providing new, simplified therapeutic methods for specific tumor destruction. The invention is based, in part, on the finding that aminophospholipids, such as phosphatidylserine and phosphatidylethanolamine, are accessible and stably targetable markers of tumor vasculature. More particularly, the invention embodies the unexpected discovery that naked antibodies against aminophospholipid components are capable of specifically inducing tumor blood vessel destruction and tumor necrosis in vivo.

Certain preferred aspects of the invention were developed from the surprising discovery that antibodies against the aminophospholipid, phosphatidylserine (PS), specifically localize to the vasculature of solid tumors and, even more surprisingly, exert a tumor destructive effect in the absence of conjugation to effector molecules, such as toxins or coagulants. Single component therapeutics directed against aminophospholipids thus represent a breakthrough in vascular targeting and provide safe and effective methods for the treatment of solid tumors.

An underlying surprising feature of the invention is that translocation of aminophospholipids, such as PS, to the surface of tumor vascular endothelial cells occurs, at least in a significant part, independently of cell damage and apoptopic or other cell-death mechanisms. PS surface expression in the tumor environment is therefore not a consequence of, or a trigger for, cell death and destruction, but occurs on morphologically intact vascular endothelial cells. This means that PS expression is not transient, but rather is stable enough to provide a target for therapeutic intervention.

The methods of the invention thus provide for killing, or specifically killing, tumor vascular endothelial cells, and comprise administering to an animal or patient having a vascularized tumor at least one dose of a biologically effective amount of at least a first pharmaceutical composition comprising a naked or unconjugated antibody, or antigen-binding region thereof, that binds to at least a first aminophospholipid expressed on the luminal surface of tumor vascular endothelial cells. The "biologically effective amount" is an amount of the naked or unconjugated antibody effective to specifically kill at least a portion, and preferably a significant portion, of the tumor vascular endothelial cells, as opposed to endothelial cells in normal vessels, upon binding to an aminophospholipid expressed on the luminal surface of the tumor vascular endothelial cells. As such, it is an "endothelial cell killing amount" or a "tumor vascular endothelial cell killing amount" of a naked or unconjugated anti-aminophospholipid antibody or antigen-binding region thereof.

As used throughout the entire application, the terms "a" and "an" are used in the sense that they mean "at least one", "at least a first", "one or more" or "a plurality" of the referenced components, except in instances wherein an upper limit is thereafter specifically stated. Therefore "an anti-aminophospholipid antibody" means "at least a first anti-aminophospholipid antibody". The operable limits and parameters of combinations, as with the amounts of any single agent, will be known to those of ordinary skill in the art in light of the present disclosure.

The "a" and "an" terms are also used to mean "at least one", "at least a first", "one or more" or "a plurality" of steps in the recited methods, except where specifically stated. This is particularly relevant to the administration steps in the treatment methods. Thus, not only may different doses be employed with the present invention, but different numbers of doses, e.g., injections, may be used, up to and including multiple injections.

An "aminophospholipid", as used herein, means a phospholipid that includes within its structure at least a first primary amino group. Preferably, the term "aminophospholipid" is used to refer to a primary amino group-containing phospholipid that occurs naturally in mammalian cell membranes. However, this is not a limitation on the meaning of the term "aminophospholipid", as this term also extends to non-naturally occurring or synthetic aminophospholipids that nonetheless have uses in the invention, e.g., as an immunogen in the generation of anti-aminophospholipid antibodies ("cross-reactive antibodies") that do bind to aminophospholipids of mammalian plasma membranes. The aminophospholipids of U.S. Pat. No. 5,767,298, incorporated herein by reference, are appropriate examples.

The prominent aminophospholipids found in mammalian biological systems are the negatively-charged phosphatidylserine ("PS") and the neutral or zwitterionic phosphatidylethanolamine ("PE"), which are therefore preferred aminophospholipids for targeting by the present invention. However, the invention is by no means limited to the targeting of phosphatidylserines and phosphatidylethanolamines, and any other aminophospholipid target may be employed (White et al., 1978; incorporated herein by reference) so long as it is expressed, accessible or complexed on the luminal surface of tumor vascular endothelial cells.

All aminophospholipid-, phosphatidylserine- and phosphatidylethanolamine-based components are encompassed as targets of the invention irrespective of the type of fatty acid chains involved, including those with short, intermediate or long chain fatty acids, and those with saturated, unsaturated and polyunsaturated fatty acids. Preferred compositions for raising antibodies for use in the present invention may be aminophospholipids with fatty acids of C18, with C18:1 being more preferred (Levy et al., 1990; incorporated herein by reference). To the extent that they are accessible on tumor vascular endothelial cells, aminophospholipid degradation products having only one fatty acid (lyso derivatives), rather than two, may also be targeted (Qamar et al., 1990; incorporated herein by reference).

Another group of potential aminophospholipid targets include, for example, phosphatidal derivatives (plasmalogens), such as phosphatidalserine and phosphatidalethanolamine (having an ether linkage giving an alkenyl group, rather than an ester linkage giving an acyl group). Indeed, the targets for therapeutic intervention by the present invention include any substantially lipid-based component that comprises a nitrogenous base and that is present, expressed, translocated, presented or otherwise complexed in a targetable form on the luminal surface of tumor vascular endothelial cells, not excluding phosphatidylcholine ("PC"). Lipids not containing glycerol may also form appropriate targets, such as the sphingolipids based upon sphingosine and derivatives.

The biological basis for including a range of lipids in the group of targetable components lies, in part, with the observed biological phenomena of lipids and proteins combining in membranous environments to form unique lipid-protein complexes. Such lipid-protein complexes extend to antigenic and immunogenic forms of lipids such as phosphatidylserine, phosphatidylethanolamine and phosphatidylcholine with, e.g., proteins such as $\beta_2$-glycoprotein I, prothrombin, kininogens and prekallikrein. Therefore, as proteins and polypeptides can have one or more free primary amino groups, it is contemplated that a range of effective "aminophospholipid targets" may be formed in vivo from lipid components that are not aminophospholipids in the strictest sense. Nonetheless, all such targetable complexes that comprise lipids and primary amino groups constitute an "aminophospholipid" within the scope of the present invention.

The inventive methods also act to arrest blood flow, or specifically arrest blood flow, in tumor vasculature. This is achieved by administering to an animal or patient having a vascularized tumor at least one dose of at least a first pharmaceutical composition comprising a coagulation-inducing amount, or a vessel-occluding amount, of at least a first naked or unconjugated antibody, or antigen-binding region thereof, that binds to an aminophospholipid, preferably phosphatidylserine or phosphatidylethanolamine, translocated to the luminal surface of tumor vasculature.

A "coagulation-inducing amount" or "vessel-occluding amount" is an amount of the naked or unconjugated antibody effective to specifically induce or promote coagulation in, and hence occlude, at least a portion, and preferably a significant portion, of tumor or intratumoral blood vessels, as opposed to normal blood vessels, upon binding to an aminophospholipid, preferably phosphatidylserine or phosphatidylethanolamine, translocated to the luminal surface of tumor blood vessels. The "vessel-occluding amount" is therefore a functionally effective amount, and is not a physical mass of antibody sufficient to span the breadth of a vessel.

Methods for destroying, or specifically destroying, tumor vasculature are provided that comprise administering to an animal or patient having a vascularized tumor one or more doses of at least a first pharmaceutical composition comprising a tumor-destructive amount of at least a first naked or unconjugated antibody, or antigen-binding region thereof, that binds to an aminophospholipid, preferably phosphatidylserine or phosphatidylethanolarnine, presented on the luminal surface of tumor vasculature. The "tumor-destructive amount" is an amount of the naked or unconjugated antibody effective to specifically destroy or occlude at least a portion, and preferably a significant portion, of tumor blood vessels, as opposed to normal blood vessels, upon binding to an aminophospholipid, preferably phosphatidylserine or phosphatidylethanolamine, presented on the luminal surface of the vascular endothelial cells of the tumor blood vessels.

The invention further encompasses methods for treating cancer and solid tumors, comprising administering to an animal or patient having a vascularized tumor a tumor necrosis-inducing amount or amounts of at least a first pharmaceutical composition comprising at least a first naked or unconjugated antibody, or antigen-binding fragment thereof, that binds to an aminophospholipid, preferably phosphatidylserine or phosphatidylethanolamine, on the luminal surface of blood vessels of the vascularized tumor. The "tumor necrosis-inducing amount" is an amount of the naked or unconjugated antibody effective to specifically induce hemorrhagic necrosis in at least a portion, and preferably a significant portion, of the tumor upon binding to an aminophospholipid, preferably phosphatidylserine or phosphatidylethanolamine, complexed at the luminal surface of the vascular endothelial cells of the tumor blood vessels, while exerting little adverse side effects on normal, healthy tissues.

The methods of the invention may thus be summarized as methods for treating an animal or patient having a vascularized tumor, comprising administering to the animal or patient at least a first dose of a therapeutically effective amount of at least a first pharmaceutical composition comprising at least a first naked or unconjugated antibody, or antigen-binding fragment thereof, that binds to an aminophospholipid (preferably phosphatidylserine or phosphatidylethanolamine) present, expressed, translocated, presented or complexed at the luminal surface of blood transporting vessels of the vascularized tumor.

The essence of the invention may also be defined as a composition comprising at least a first naked or unconjugated anti-aminophospholipid antibody, preferably an anti-phosphatidylserine or anti-phosphatidylethanolamine antibody, or antigen-binding fragment thereof, for use in the preparation of a medicament for use in tumor vasculature destruction and for human tumor treatment. This can also be defined as a composition comprising at least a first naked or unconjugated anti-aminophospholipid antibody, preferably an anti-PS or anti-PE antibody, or antigen-binding fragment thereof, for use in the preparation of a medicament for use in binding to an aminophospholipid, preferably phosphatidylserine or phosphatidylethanolamine, present, expressed, translocated, presented or complexed at the luminal surface of blood transporting vessels of a vascularized tumor and for use in inducing tumor vasculature destruction and for human tumor treatment.

In the methods, medicaments and uses of the present invention, one of the advantages lies in the fact that the provision of a simple naked or unconjugated anti-aminophospholipid antibody composition, preferably anti-phosphatidylserine or anti-phosphatidylethanolamine, into the systemic circulation of an animal or patient results in the preferential or specific destruction of the tumor vasculature and the induction of tumor necrosis. The invention therefore solves the problem of the complex preparative methods of the multicomponent anti-vasculara gents of the prior art.

The terms "naked" and "unconjugated" antibody, as used herein, are intended to refer to an antibody that is not conjugated, operatively linked or otherwise physically or functionally associated with an effector moiety, such as a cytotoxic or coagulative agent. It will be understood that the terms "naked" and "unconjugated" antibody do not exclude antibody constructs that have been stabilized, multimerized, humanized or in any other way manipulated, other than by the attachment of an effector moiety.

Accordingly, all post-translationally modified naked and unconjugated antibodies are included herewith, including where the modifications are made in the natural antibody-producing cell environment, by a recombinant antibody-producing cell, and are introduced by the hand of man after initial antibody preparation. Of course, the term "naked" antibody does not exclude the ability of the antibody to form functional associations with effector cells and/or molecules after administration to the body, as some such interactions are necessary in order to exert a biological effect. The lack of associated effector group is therefore applied in definition to the naked antibody in vitro, not in vivo.

In the context of the present invention, the term "a vascularized tumor" most preferably means a vascularized, malignant tumor, solid tumor or "cancer". The invention is particularly advantageous in treating vascularized tumors of at least about intermediate size, and in treating large vascularized tumors—although this is by no means a limitation on the invention. The invention may therefore be used in the treatment of any tumor that exhibits aminophospholipid-positive blood vessels, preferably phosphatidylserine- and/or phosphatidylethanolamine-positive blood vessels.

In preferred embodiments, the tumors to be treated by the present invention will exhibit a killing effective number of aminophospholipid-positive blood vessels. "A killing effective number of aminophospholipid-positive blood vessels", as used herein, means that at least about 3% of the total number of blood vessels within the tumor will be positive for aminophospholipid expression, preferably phosphatidylserine and/or phosphatidylethanolamine expression. Preferably, at least about 5%, at least about 8%, or at least about 10% or so, of the total number of blood vessels within the tumor will be positive for aminophospholipid expression. Given the aminophospholipid-negative, particularly PS-negative, nature of the blood vessels within normal tissues, the tumor vessels will act as sink for the administered antibodies. Furthermore, as destruction of only a minimum number of tumor vessels can cause widespread thrombosis, necrosis and an avalanche of tumor cell death, antibody localization to all, or even a majority, of the tumor vessels is not necessary for effective therapeutic intervention.

Nonetheless, in more preferred embodiments, tumors to be treated by this invention will exhibit a significant number of aminophospholipid-positive blood vessels. "A significant number of aminophospholipid-positive blood vessels", as used herein, means that at least about 10–12% of the total number of blood vessels within the tumor will be positive for aminophospholipid expression, preferably phosphatidylserine and/or phosphatidylethanolamine expression. Even more preferably, the % of aminophospholipid-expressing tumor vessels will be at least about 15%, at least about 20%, at least about 30%, at least about 40%, at least about 50%, at least about 60%, at least about 70%, or at least about 80% or so of the total number of blood vessels within the tumor, up to and including even at least about 90% or 95% of the vessels.

The "therapeutically effective amounts" for use in the invention are amounts of naked or unconjugated anti-amninophospholipid antibodies, preferably anti-PS or anti-PE antibodies, effective to specifically kill at least a portion of tumor vascular endothelial cells; to specifically promote coagulation in at least a portion of tumor blood vessels; to specifically occlude or destroy at least a portion of blood transporting vessels of the tumor; to specifically induce necrosis in at least a portion of a tumor; and/or to induce tumor regression or remission upon administration to selected animals or patients. Such effects are achieved while exhibiting little or no binding to, or little or no killing of, vascular endothelial cells in normal, healthy tissues; little or no coagulation in, occlusion or destruction of blood vessels in healthy, normal tissues; and exerting negligible or manageable adverse side effects on normal, healthy tissues of the animal or patient.

The terms "preferentially" and "specifically", as used herein in the context of promoting coagulation in, or destroying, tumor vasculature, and/or in the context of causing tumor necrosis, thus mean that anti-aminophospholipid antibodies function to achieve coagulation, destruction and/or tumor necrosis that is substantially confined to the tumor vasculature and tumor site, and does not substantially extend to causing coagulation, destruction and/or tissue necrosis in normal, healthy tissues of the animal or subject. The structure and function of healthy cells and tissues is therefore maintained substantially unimpaired by the practice of the invention.

Therapeutic benefits may be realized by the administration of at least two, three or more naked or unconjugated anti-aminophospholipid antibodies; bispecific antibodies; chimeric antibodies; and/or dimeric, trimeric or multimeric antibodies. The anti-aminophospholipid antibodies may also be combined with other therapies to provide combined therapeutically effective amounts, as disclosed herein.

Although understanding the mechanism of action is not necessary to the practice of the present anti-aminophospholipid antibody treatment invention, the methods may operate to induce cell-mediated cytotoxicity, complement-mediated lysis and/or apoptosis. The cytotoxic methods may also be based upon antibody-induced cell signaling (direct signaling), or mimicking or altering signal transduction pathways (indirect signaling). The ability of the anti-aminophospholipid antibodies to localize and bind to a component of the membrane itself may also be relevant, as opposed to previous therapies that are generally directed to binding to a protein component or complex, which may be sterically distinct or distant from the membrane surface itself.

The treatment methods thus include administering to an animal or patient having a vascularized tumor at least a first pharmaceutical composition comprising an amount of at least a first antibody construct effective to induce, or specifically induce, cell-mediated cytotoxicity of at least a portion of the tumor vascular endothelial cells. Herein, the first antibody construct is a naked or unconjugated antibody, or effective fragment thereof, that binds to an aminophospholipid, preferably phosphatidylserine or phosphatidylethanolamine, present, expressed, translocated, presented or complexed at the luminal surface of tumor vascular endothelial cells and that induces cell-mediated cytotoxicity of at least a portion of the tumor vascular endothelial cells, as opposed to endothelial cells in normal vessels. As used herein, "cell-mediated cytotoxicity or destruction" includes ADCC (antibody-dependent, cell-mediated cytotoxicity) and NK (natural killer) cell killing.

The methods further include administering to an animal or patient having a vascularized tumor at least a first pharmaceutical composition comprising an amount of at least a first antibody construct effective to induce, or specifically induce, complement-mediated lysis of at least a portion of the tumor vascular endothelial cells. Herein, the first antibody construct is a naked or unconjugated antibody, or effective fragment thereof, that binds to an aminophospholipid, preferably phosphatidylserine or phosphatidylethanolamine, present, expressed, translocated, presented or complexed at the luminal surface of tumor vascular endothelial cells and that induces complement-mediated lysis of at least a portion of the tumor vascular endothelial cells, as opposed to endothelial cells in normal vessels. As used herein, "complement-mediated or complement-dependent lysis or cytotoxicity" means the process by which the complement-dependent coagulation cascade is activated, multi-component complexes are assembled, ultimately generating a lytic complex that has direct lytic action, causing cell permeabilization. Anti-aminophospholipid antibodies for use in inducing complement-mediated lysis will generally include the Fc portion of the antibody.

The complement-based mechanisms by which the present invention may operate further include "complement-activated ADCC". In such aspects, the administered naked or unconjugated antibodies, or fragments thereof, bind to an aminophospholipid, preferably phosphatidylserine or phosphatidylethanolamine, present, expressed, translocated, presented or complexed at the luminal surface of tumor vascular endothelial cells and induce complement-activated ADCC of at least a portion of the tumor vascular endothelial cells, as opposed to endothelial cells in normal vessels. "Complement-activated ADCC" is used to refer to the process by which complement, not an antibody Fc portion per se, holds a multi-component complex together and in which cells such as neutrophils lyse the target cell.

In other embodiments, the methods include administering to an animal or patient having a vascularized tumor at least a first pharmaceutical composition comprising an amount of at least a first antibody construct effective to induce, or specifically induce, apoptosis in at least a portion of the tumor vascular endothelial cells. Herein, the first antibody construct is a naked or unconjugated antibody, or antigen-binding fragment thereof, that binds to an aminophospholipid, preferably phosphatidylserine or phosphatidylethanolamine, present, expressed, translocated, presented or complexed at the luminal surface of tumor vascular endothelial cells and that induces apoptosis in least a portion of the tumor vascular endothelial cells, as opposed to endothelial cells in normal vessels. As used herein, "induces apoptosis" means induces the process of programmed cell death that, during the initial stages, maintains the integrity of the cell membrane, yet transmits the death-inducing signals into the cell. This is opposed to the mechanisms of cell necrosis, during which the cell membrane loses its integrity and becomes leaky at the onset of the process.

The anti-aminophospholipid antibody treatment methods will generally involve the administration of at least one dose of the pharmaceutically effective composition to the animal systemically, such as via intravenous injection. However, any route of administration that allows the antibody localize to the tumor vascular endothelial cells and to induce cell-mediated cytotoxicity, complement-mediated lysis and/or apoptosis thereof will be acceptable.

"Administration", as used herein, therefore means provision or delivery of anti-aminophospholipid antibodies in an amount(s) and for a period of time(s) effective to allow binding to an aminophospholipid, preferably phosphatidylserine or phosphatidylethanolamine, present, expressed, translocated, presented or complexed at the luminal surface of blood transporting vessels of the vascularized tumor, and to exert a tumor vasculature destructive and tumor-regressive effect. The passive administration of proteinaceous antibodies is generally preferred, in part, for its simplicity and reproducibility.

However, the term "administration" is herein used to refer to any and all means by which anti-aminophospholipid antibodies are delivered or otherwise provided to the tumor vasculature. "Administration" therefore includes the provision of cells, such as hybridomas, that produce the anti-aminophospholipid antibodies in a manner effective to result in the delivery of the anti-aminophospholipid antibodies to the tumor vasculature, and/or their localization to such vasculature. In such embodiments, it may be desirable to formulate or package the antibody-producing cells in a selectively permeable membrane, structure or implantable device, generally one that can be removed to cease therapy.

"Antibody administration", as used herein, also extends to all methods by which anti-aminophospholipid antibodies are generated in a patient ("endogenous antibodies"), allowing them to circulate and localize to the tumor vasculature. Therefore, "administration" also includes the active immunization of a patient with an immunogenically effective amount of an aminophospholipid sample, antigen or immunogen. All methods of human immunization are appropriate for use in such embodiments, as exemplified by those described below in the context of generating an anti-aminophospholipid antibody response in an animal in order to obtain the antibody therefrom. Exogenous antibody administration will still generally be preferred over cell- and immunization-based delivery, as this represents a less invasive method that allows the dose to be closely monitored and controlled.

The "antibody administration methods" of the invention also extend to the provision of nucleic acids that encode anti-aminophospholipid antibodies in a manner effective to result in the expression of the anti-aminophospholipid antibodies in the vicinity of the tumor vasculature, and/or in the expression of anti-aminophospholipid antibodies that can localize to the tumor vasculature. Any gene therapy technique may be employed, such as naked DNA delivery, recombinant genes and vectors, cell-based delivery, including ex vivo manipulation of patients' cells, and the like.

One of the benefits of the present invention is that aminophospholipids, particularly phosphatidylserine and phosphatidylethanolamine, are generally expressed or available throughout the tumor vessels. Aminophospholipid expression on established, intratumoral blood vessels is advantageous as targeting and destroying such vessels will rapidly lead to anti-tumor effects. However, so long as the administered anti-aminophospholipid antibodies bind to at least a portion of the blood transporting vessels, significant anti-tumor effects will ensue. This will not be problematical as aminophospholipids, such as phosphatidylserine and phosphatidylethanolamine, are expressed on the large, central vessels, and also on veins, venules, arteries, arterioles and blood transporting capillaries in all regions of the tumor.

In any event, the ability of the anti-aminophospholipid antibodies to destroy the tumor vasculature means that tumor regression can be achieved, rather than only tumor stasis. Tumor stasis is most often the result of anti-angiogenic therapies that target only the budding vessels at the periphery of a solid tumor and stop the vessels proliferating. Even if the present invention targeted more of the peripheral regions of the tumor in certain tumor types, which is not currently believed to be the case, destruction of the blood transporting vessels in such areas would still lead to widespread thrombosis and tumor necrosis.

In any of the foregoing methods, the terms anti-aminophospholipid "antibody, naked antibody and unconjugated antibody", as used herein, refer broadly to any immunologic binding agent, such as polyclonal and monoclonal IgG, IgM, IgA, IgD and IgE antibodies. Generally, IgG and/or IgM are preferred because they are the most common antibodies in the physiological situation and because they are most easily made in a laboratory setting.

Polyclonal anti-aminophospholipid antibodies, obtained from antisera, may be employed in the invention. However, the use of monoclonal anti-aminophospholipid antibodies (MAbs) will generally be preferred. MAbs are recognized to have certain advantages, e.g., reproducibility and large-scale production, that makes them suitable for clinical treatment. The invention thus provides monoclonal antibodies of the murine, human, monkey, rat, hamster, rabbit and even frog or chicken origin. Due to the ease of preparation and ready availability of reagents, murine monoclonal antibodies will be used in certain embodiments.

As will be understood by those in the art, the immunologic binding reagents encompassed by the term "anti-aminophospholipid antibody" extend to all naked and unconjugated anti-aminophospholipid antibodies from all species, and antigen binding fragments thereof, including dimeric, trimeric and multimeric antibodies; bispecific antibodies; chimeric antibodies; human and humanized antibodies; recombinant and engineered antibodies, and fragments thereof.

The term "anti-aninophospholipid antibody" is thus used to refer to any anti-aminophospholipid antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art.

In certain embodiments, the antibodies employed will be "humanized" or human antibodies. "Humanized" antibodies are generally chimeric monoclonal antibodies from mouse, rat, or other non-human species, bearing human constant and/or variable region domains ("part-human chimeric antibodies"). Mostly, humanized monoclonal antibodies for use in the present invention will be chimeric antibodies wherein at least a first antigen binding region, or complementarity determining region (CDR), of a mouse, rat or other non-human anti-aminophospholipid monoclonal antibody is operatively attached to, or "grafted" onto, a human antibody constant region or "framework".

"Humanized" monoclonal antibodies for use herein may also be anti-aminophospholipid monoclonal antibodies from non-human species wherein one or more selected amino acids have been exchanged for amino acids more commonly observed in human antibodies. This can be readily achieved through the use of routine recombinant technology, particularly site-specific mutagenesis.

Entirely human, rather than "humanized", anti-aminophospholipid antibodies may also be prepared and used in the present invention. Such human antibodies may be polyclonal antibodies, as obtained from human patients that have any one or more of a variety of diseases, disorders or clinical conditions associated with the production of anti-aminophospholipid antibodies. Such antibodies may be concentrated, partially purified or substantially purified for use herein.

A range of techniques are also available for preparing human monoclonal antibodies. As human patients with anti-aminophospholipid antibody-producing diseases exist, the anti-aminophospholipid antibody-producing cells from such patients may be obtained and manipulated in vitro to provide a human monoclonal antibody. The in vitro manipulations or techniques include fusing to prepare a monoclonal antibody-producing hybridoma, and/or cloning the gene(s) encoding the anti-aminophospholipid antibody from the cells ("recombinant human antibodies").

Human anti-aminophospholipid antibody-producing cells may also be obtained from human subjects without an anti-aminophospholipid antibody-associated disease, i.e. "healthy subjects" in the context of the present invention. To achieve this, one would simply obtain a population of mixed peripheral blood lymphocytes from a human subject, including antigen-presenting and antibody-producing cells, and stimulate the cell population in vitro by admixing with an immunogenically effective amount of an aminophospholipid sample. Again, the human anti-aminophospholipid antibody-producing cells, once obtained, could be used in hybridoma and/or recombinant antibody production.

Further techniques for human monoclonal antibody production include immunizing a transgenic animal, preferably a transgenic mouse, that comprises a human antibody library with an immunogenically effective amount of an aminophospholipid sample. This also generates human anti-aminophospholipid antibody-producing cells for further manipulation in hybridoma and/or recombinant antibody production, with the advantage that spleen cells, rather than peripheral blood cells, can be readily obtained from the transgenic animal or mouse.

As used herein, the term "anti-aminophospholipid antibody" is used co-extensively with "naked and unconjugated" to mean anti-aminophospholipid antibodies, and antigen binding fragments thereof, that are not conjugated to, or operatively associated with, an effector molecule, such as a cytotoxic agent or coagulant. In addition to non-effector modifications of the antibody, and in vivo interactions, the term "naked" in no way excludes combinations of the antibody with other therapeutic agents, as disclosed in detail herein.

In contrast, anti-aminophospholipid antibodies, bispecific antibodies, and antigen binding fragments thereof, that are conjugated to, or operatively associated with, cytotoxic or anticellular agents are referred to herein as "anti-aminophospholipid immunotoxins". Likewise, anti-aminophospholipid antibodies, bispecific antibodies, and antigen binding fragments thereof, that are conjugated to, or operatively associated with, coagulation factors are herein referred to as "anti-aminophospholipid coaguligands". The use of anti-aminophospholipid immunotoxins and anti-aminophospholipid coaguligands in tumor treatment is also contemplated by the present inventors and is disclosed and claimed in first and second provisional applications Ser. No. 60/092,589 (filed Jul. 13, 1998) and Ser. No. 60/110,600 (filed Dec. 2, 1998) and in co-filed U.S. and PCT patent application Ser. No. 09/351,457, now U.S. Pat. No. 6,132,694; Ser. No. 09/351,598, Ser. No. 09/351,149 and WO 00/02584, each specifically incorporated herein by reference.

Preferred anti-aminophospholipid antibodies for use in the present invention are anti-phosphatidylserine (anti-PS) and anti-phosphatidylethanolamine (anti-PE) antibodies. Anti-PS antibodies will generally recognize, bind to or have immunospecificity for the PS molecule present, expressed, translocated, presented or complexed at the luminal surface of tumor vascular endothelial cells. Suitable antibodies will thus bind to phosphatidyl-L-serine (Umeda et al., 1989; incorporated herein by reference). Anti-PE antibodies will generally recognize, bind to or have immunospecificity for the PE molecule present, expressed, translocated, presented or complexed at the luminal surface of tumor vascular endothelial cells.

Administering anti-aminophospholipid antibodies to an animal with a tumor will result in specific binding of the antibody to the aminophospholipid molecules present, expressed or translocated to the luminal surface of the tumor blood vessels, i.e., the antibodies will bind to the aminophospholipid molecules in a natural, biological environment. Therefore, no particular manipulation will be necessary to ensure antibody binding.

However, it is of scientific interest to note that aminophospholipids may be most frequently recognized, or bound, by anti-aminophospholipid antibodies when the aminophospholipid molecules are associated with one or more proteins or other non-lipid biological components. For example, anti-PS antibodies that occur as a sub-set of anti-phospholipid (anti-PL) antibodies in patients with certain diseases and disorders are now believed to bind to PS in combination with proteins such as $\beta_2$-glycoprotein I ($\beta_2$-GPI or apolipoprotein H, apoH) and prothrombin (U.S. Pat. No. 5,344,758; Rote, 1996; each incorporated herein by reference). Similarly, anti-PE antibodies that occur in disease states are now believed to bind to PE in combination with proteins such as low and high molecular weight kininogen (HK), prekallikrein and even factor XI (Sugi and McIntyre, 1995; 1996a; 1996b; each incorporated herein by reference).

This is the meaning of the terms "presented" and "complexed at" the luminal surface of tumor blood vessels, as used herein, which mean that the aminophospholipid molecules are present at the surface of tumor blood vessels in an antibody-binding competent state, irrespective of the molecular definition of that particular state. PS may even be targeted as a complex with factor II/Ia, VII/VIIa, IX/IXa and X/Xa. Moreover, the nature of the aminophospholipid target may change during practice of the invention, as the initial aminophospholipid antibody binding, anti-endothelial cell and anti-tumor effects may result in biological changes that alter the number, conformation and/or type of the aminophospholipid target epitope(s).

The term "anti-aminophospholipid antibody", as used in the context of the present invention, therefore means any naked or unconjugated anti-aminophospholipid antibody, immunological binding agent or antisera; monoclonal, human, humanized, dimeric, trimeric, multimeric, chimeric, bispecific, recombinant or engineered antibody; or Fab', Fab, F(ab')$_2$, DABs, Fv or scFv antigen binding fragment thereof; that at least binds to a lipid and amino group-containing complex or aminophospholipid target, preferably a phosphatidylserine- or phosphatidylethanolamine-based target.

The requirement that the antibody "at least bind to an aminophospholipid target" is met by the antibody binding to any and/or all physiologically relevant forms of aminophospholipids, as including so-called "hexagonal" and "hexagonal phase II" PS and PE (HexII PS and HexII PE) (Rauch et al., 1986; Rauch and Janoff, 1990; Berard et al., 1993; each incorporated herein by reference) and PS and PE in combination with any other protein, lipid, membrane component, plasma or serum component, or any combination thereof. Thus, an "anti-aminophospholipid antibody" is an antibody that binds to an aminophospholipid in the tumor blood vessels, notwithstanding the fact that bilayer or micelle aminophospholipids may be considered to be immunogenically neutral.

The anti-aminophospholipid antibodies may recognize, bind to or have immunospecificity for aminophospholipid molecules, or an immunogenic complex thereof (including hexagonal aminophospholipids and protein combinations), to the exclusion of other phospholipids or lipids. Such antibodies may be termed "aminophospholipid-specific or aminophospholipid-restricted antibodies", and their use in the invention will often be preferred. "Aminophospholipid-specific or aminophospholipid-restricted antibodies" will generally exhibit significant binding to aminophospholipids, while exhibiting little or no significant binding to other lipid components, such as phosphatidylinositol (PI), phosphatidylglycerol (PG) and even phosphatidylcholine (PC) in certain embodiments.

"PS-specific or PS-restricted antibodies" will generally exhibit significant binding to PS, while exhibiting little or no significant binding to lipid components such as phosphatidylethanolamine and cardiolipin (CL), as well as PC, PI and PG. "PE-specific or PE-restricted antibodies" will generally exhibit significant binding to PE, while exhibiting little or no significant binding to lipid components such as phosphatidylserine and cardiolipin, as well as PC, PI and PG. The preparation of specific anti-aminophospholipid antibodies is readily achieved, e.g., as disclosed by Rauch et al. (1986); Umeda et al. (1989); Rauch and Janoff (1990); and Rote et al. (1993); each incorporated herein by reference.

"Cross-reactive anti-aminophospholipid antibodies" that recognize, bind to or have immunospecificity for an aminophospholipid molecule, or an immunogenic complex thereof (including hexagonal aminophospholipids and protein combinations), in addition to exhibiting lesser but detectable binding to other phospholipid or lipid components are by no means excluded from use in the invention. Such "cross-reactive anti-aminophospholipid antibodies" may be employed so long as they bind to an aminophospholipid present, expressed, translocated, presented or complexed at the luminal surface of tumor vascular endothelial cells and exert an anti-tumor effect upon administration in vivo.

Further suitable aminophospholipid-specific or aminophospholipid-restricted antibodies are those anti-aminophospholipid antibodies that bind to both PS and PE. While clearly being specific or restricted to aminophospholipids, as opposed to other lipid components, antibodies exist that bind to each of the preferred targets of the present invention. Examples of such antibodies for use in the invention include, but are not limited to, PS3A, PSF6, PSF7, PSB4, PS3H1 and PS3E10 (Igarashi et al., 1991; incorporated herein by reference)

Further exemplary anti-PS antibodies for use in the invention include, but are not limited to BA3B5C4, PS4A7, PS1G3 and 3SB9b; with PS4A7, PS1G3 and 3SB9b generally being preferred. Monoclonal antibodies, humanized antibodies and/or antigen-binding fragments based upon the 3SB9b antibody (Rote et al., 1993; incorporated herein by reference) are currently most preferred.

Although aminophospholipids, such as PS and PE, in bilayer or micelle form have been reported to be non- or weakly antigenic, or non- or weakly-immunogenic, the scientific literature has reported no difficulties in generating anti-aminophospholipid antibodies, such as anti-PS and anti-PE antibodies. Anti-aminophospholipid antibodies or monoclonal antibodies may therefore be readily prepared by preparative processes and methods that comprise:

(a) preparing an anti-aminophospholipidantibody-producing cell; and (b) obtaining an anti-aminophospholipid antibody or monoclonal antibody from the antibody-producing cell.

The processes of preparing anti-aminophospholipidantibody-producing cells and obtaining anti-aminophospholipidantibodies therefrom may be conduced in situ in a given patient. That is, simply providing an immunogenically effective amount of an immunogenic aminophospholipid sample to a patient will result in anti-aminophospholipid antibody generation. Thus, the anti-aminophospholipid antibody is still "obtained" from the antibody-producing cell, but it does not have to be isolated away from a host and subsequently provided to a patient, being able to spontaneously localize to the tumor vasculature and exert its biological anti-tumor effects.

As disclosed herein, anti-aminophospholipid antibody-producing cells may be obtained, and antibodies subsequently isolated and/or purified, from human patients with anti-aminophospholipid antibody-producing diseases, from stimulating peripheral blood lymphocytes with aminophospholipidsin vitro, and also by immunization processes and methods. The latter of which generally comprise:

(a) immunizing an animal by administering to the animal at least one dose, and optionally more than one dose, of an immunogenically effective amount of an immunogenic aminophospholipid sample (such as a hexagonal, or hexagonal phase II form of an aminophospholipid), preferably an immunogenic PS or PE sample; and (b) obtaining an anti-aminophospholipid antibody-producing cell from the immunized animal.

The immunogenically effective amount of the aminophospholipid sample or samples may be a Salmonella-coated aminophospholipid sample (Umeda et al., 1989; incorporated herein by reference); an aminophospholipid micelle, liposome, lipid complex or lipid formulation sample; or an aminophospholipid sample fabricated with SDS. Any such aminophospholipid sample may be administered in combination with any suitable adjuvant, such as Freund's complete adjuvant (Rote et al., 1993; incorporated herein by reference). Any empirical technique or variation may be employed to increase immunogenicity, and/or hexagonal or hexagonal phase II forms of the aminophospholipids may be administered.

The immunization may be based upon one or more intrasplenic injections of an immunogenically effective amount of an aminophospholipid sample (Umeda et al., 1989; incorporated herein by reference).

Irrespective of the nature of the immunization process, or the type of immunized animal, anti-aminophospholipid antibody-producing cells are obtained from the immunized animal and, preferably, further manipulated by the hand of man. "An immunized animal", as used herein, is a non-human animal, unless otherwise expressly stated. Although any antibody-producing cell may be used, most preferably, spleen cells are obtained as the source of the antibody-producing cells. The anti-aminophospholipid antibody-producing cells may be used in a preparative process that comprises:

(a) fusing an anti-aminophospholipidantibody-producing cell with an immortal cell to prepare a hybridoma that produces an anti-aminophospholipidmonoclonal antibody and (b) obtaining an anti-aminophospholipidmonoclonal antibody from the hybridoma.

Hybridoma-based monoclonal antibody preparative methods thus include those that comprise:

(a) immunizing an animal by administering to the animal at least one dose, and optionally more than one dose, of an immunogenically effective amount of an immunogenic aminophospholipid sample (such as a hexagonal, or hexagonal phase II form of an aminophospholipid), preferably an immunogenic PS or PE sample;

(b) preparing a collection of monoclonal antibody-producing hybridomas from the immunized animal;

(c) selecting from the collection at least a first hybridoma that produces at least a first anti-aminophospholipid monoclonal antibody, and preferably, at least a first aminophospholipid-specific monoclonal antibody; and (d) culturing the at least a first anti-aminophospholipid-producing or aminophospholipid-specific hybridoma to provide the at least a first anti-aminophospholipid monoclonal antibody or aminophospholipid-specific monoclonal antibody; and preferably (e) obtaining the at least a first anti-aminophospholipid monoclonal antibody or aminophospholipid-specific monoclonal antibody from the cultured at least a first hybridoma.

As non-human animals are used for immunization, the anti-aminophospholipid monoclonal antibodies obtained from such a hybridoma will often have a non-human make up. Such antibodies may be optionally subjected to a humanization process, grafting or mutation, as known to those of skill in the art and further disclosed herein. Alternatively, transgenic animals, such as mice, may be used that comprise a human antibody gene library. Immunization of such animals will therefore directly result in the generation of human anti-aminophospholipid antibodies.

After the production of a suitable antibody-producing cell, most preferably a hybridoma, whether producing human or non-human antibodies, the monoclonal antibody-encoding nucleic acids may be cloned to prepare a "recombinant" monoclonal antibody. Any recombinant cloning technique may be utilized, including the use of PCR to prime the synthesis of the antibody-encoding nucleic acid sequences. Therefore, yet further appropriate monoclonal antibody preparative methods include those that comprise using the anti-aminophospholipid antibody-producing cells as follows:

(a) obtaining at least a first anti-aminophospholipid antibody-encoding nucleic acid molecule or segment from an anti-aminophospholipid antibody-producing cell, preferably a hybridoma; and (b) expressing the nucleic acid molecule or segment in a recombinant host cell to obtain a recombinant anti-aminophospholipidmonoclonal antibody.

However, other powerful recombinant techniques are available that are ideally suited to the preparation of recombinant monoclonal antibodies. Such recombinant techniques include the phagemid library-based monoclonal antibody preparative methods comprising:

(a) immunizing an animal by administering to the animal at least one dose, and optionally more than one dose, of an immunogenically effective amount of an immunogenic aminophospholipid sample (such as a hexagonal, or hexagonal phase II form of an aminophospholipid), preferably an immunogenic PS or PE sample;

(b) preparing a combinatorial immunoglobulin phagemid library expressing RNA isolated from the antibody-producing cells, preferably from the spleen, of the immunized animal;

(c) selecting from the phagemid library at least a first clone that expresses at least a first anti-aminophospholipid antibody, and preferably, at least a first aminophospholipid-specific antibody;

(d) obtaining anti-aminophospholipidantibody-encodingnucleic acids from the at least a first selected clone and expressing the nucleic acids in a recombinant host cell to provide the at least a first anti-aminophospholipid antibody or aminophospholipid-specific antibody; and preferably (e) obtaining the at least a first anti-aminophospholipid antibody or aminophospholipid-specific antibody expressed by the nucleic acids obtained from the at least a first selected clone.

Again, in such phagemid library-based techniques, transgenic animals bearing human antibody gene libraries may be employed, thus yielding recombinant human monoclonal antibodies.

Irrespective of the manner of preparation of a first anti-aminophospholipid antibody nucleic acid segment, further suitable anti-aminophospholipid antibody nucleic acid segments may be readily prepared by standard molecular biological techniques. In order to confirm that any variant, mutant or second generation anti-aminophospholipid antibody nucleic acid segment is suitable for use in the present invention, the nucleic acid segment will be tested to confirm expression of an antibody that binds to an aminophospholipid. Preferably, the variant, mutant or second generation anti-aminophospholipid antibody nucleic acid segment will also be tested to confirm hybridization to an anti-aminophospholipid antibody nucleic acid segment under standard, more preferably, standard stringent hybridization conditions. Exemplary suitable hybridization conditions include hybridization in about 7% sodium dodecyl sulfate (SDS), about 0.5 M $NaPO_4$, about 1 mM EDTA at about 50° C.; and washing with about 1% SDS at about 42° C.

As a variety of recombinant monoclonal antibodies, whether human or non-human in origin, may be readily prepared, the treatment methods of the invention may be executed by providing to the animal or patient at least a first nucleic acid segment that expresses a biologically effective amount of at least a first anti-aminophospholipid antibody in the patient. The "nucleic acid segment that expresses an anti-aminophospholipid antibody" will generally be in the form of at least an expression construct, and may be in the form of an expression construct comprised within a virus or within a recombinant host cell. Preferred gene therapy vectors of the present invention will generally be viral vectors, such as comprised within a recombinant retrovirus, herpes simplex virus (HSV), adenovirus, adeno-associated virus (AAV), cytomegalovirus (CMV), and the like.

In certain embodiments, the vasculature of the vascularized tumor of the animal or patient to be treated may be first imaged. Generally this is achieved by first administering to the animal or patient a diagnostically effective amount of at least a first pharmaceutical composition comprising at least a first detectably-labeled aminophospholipid binding construct, such as an anti-aminophospholipid antibody-detectable agent construct, that binds to and identifies an aminophospholipid, preferably phosphatidylserine or phosphatidylethanolamine, present, expressed, translocated, presented or complexed at the luminal surface of blood vessels of the vascularized tumor. The invention thus further provides compositions for use in, and methods of, distinguishing between tumor and/or intratumoral blood vessels and normal blood vessels. The "distinguishing" is achieved by administering one or more of the detectably-labeled aminophospholipid binding constructs described.

The detectably-labeled aminophospholipid binding construct or anti-aminophospholipid antibody-detectable agent construct may comprise an X-ray detectable compound, such as bismuth (III), gold (III), lanthanum (III) or lead (II); a radioactive ion, such as $copper^{67}$, $gallium^{67}$, $gallium^{68}$, $indium^{111}$, $indium^{113}$, $iodine^{123}$, $iodine^{125}$, $iodine^{131}$, $mercury^{197}$, $mercury^{203}$, $rhenium^{186}$, $rhenium^{188}$, $rubidium^{97}$, $rubidium^{103}$, $technetium^{99m}$ or $yttrium^{90}$; a nuclear magnetic spin-resonance isotope, such as cobalt (II), copper (II), chromium (III), dysprosium (III), erbium (III), gadolinium (III), holmium (III), iron (II), iron (III), manganese (II), neodymium (III), nickel (II), samarium (III), terbium (III), vanadium (II) or ytterbium (III); or rhodamine or fluorescein.

Pre-imaging before tumor treatment may thus be carried out by:

(a) administering to the animal or patient a diagnostically effective amount of a pharmaceutical composition comprising at least a first detectably-labeled aminophospholipid binding construct that comprises a diagnostic agent operatively attached to an antibody, binding protein or ligand, or aminophospholipid binding fragment thereof, that binds to an aminophospholipid, preferably phosphatidylserine or phosphatidylethanolamine, present, expressed, translocated, presented or complexed at the luminal surface of blood vessels or intratumoral blood vessels of the vascularized tumor; and (b) subsequently detecting the detectably-labeled aminophospholipid binding construct bound to an aminophospholipid, preferably phosphatidylserine or phosphatidylethanolamine, on the luminal surface of tumor or intratumoral blood vessels, thereby obtaining an image of the tumor vasculature.

Cancer treatment may also be carried out by:

(a) forming an image of a vascularized tumor by administering to an animal or patient having a vascularized tumor a diagnostically minimal amount of at least a first detectably-labeled aminophospholipid binding construct comprising a diagnostic agent operatively attached to an antibody, binding protein or ligand, or aminophospholipid binding fragment thereof, that binds to an aminophospholipid, preferably phosphatidylserine or phosphatidylethanolamine, on the luminal surface of tumor or intratumoral blood vessels of the vascularized tumor, thereby forming a detectable image of the tumor vasculature; and (b) subsequently administering to the same animal or patient a therapeutically optimized amount of at least a first naked antibody, or antigen-binding fragment thereof, that binds to an aminophospholipid, preferably phosphatidylserine or phosphatidylethanolamine, on the tumor blood vessel luminal surface and thereby destroys the tumor vasculature.

Imaging and treatment formulations or medicaments are thus provided, which generally comprise:

(a) a first pharmaceutical composition comprising a diagnostically effective amount of a detectably-labeled aminophospholipid binding construct that comprises a detectable agent operatively attached to an antibody, binding protein or ligand, or aminophospholipid binding fragment thereof, that binds to an aminophospholipid, preferably phosphatidylserine or phosphatidylethanolamine, on the luminal surface of tumor or intratumoral blood vessels of the vascularized tumor; and (b) at least a second pharmaceutical composition comprising a therapeutically effective amount of at least a second, unconjugated anti-aminophospholipid antibody, preferably anti-phosphatidylserine or anti-phosphatidylethanolamine, or antigen binding fragment thereof.

In such methods and medicaments, advantages will be realized wherein the first and second pharmaceutical compositions comprise the same targeting agents, e.g., anti-aminophospholipid antibodies, or fragments thereof, from the same antibody preparation, or preferably, from the same antibody-producing hybridoma.

In the vasculature imaging aspects of the invention, it is recognized that the administered detectably-labeled aminophospholipid binding construct, or anti-aminophospholipid antibody-detectable agent, may itself have a therapeutic effect. Whilst this would not be excluded from the invention, the amounts of the detectably-labeledconstructs to be administered would generally be chosen as "diagnostically effective amounts", which are typically lower than the amounts required for therapeutic benefit.

In the imaging embodiments, the targeting agent may be either antibody-based or binding ligand- or binding protein-based. Although not previously connected with tumors or tumor vasculature, detectably labeled aminophospholipid binding ligand compositions are known in the art and can now, in light of this motivation and the present disclosure, be used in the combined imaging and treatment aspects of the present invention. The detectably-labeled annexins of U.S. Pat. No. 5,627,036; WO 95/19791; WO 95/27903; WO 95/34315; WO 96/17618; and WO 98/04294; each incorporated herein by reference; may thus be employed.

The foregoing imaging and treatment formulations or medicaments may also further comprise one or more anti-cancer agents. That is, the present invention encompasses imaging and combination treatment formulations and medicaments that generally comprise (a) diagnostically effective amounts of detectably-labeled aminophospholipid binding constructs; (b) therapeutically effective amounts of unconjugated anti-aminophospholipid antibodies, preferably anti-phosphatidylserine or anti-phosphatidylethanolamine, or antigen binding fragments thereof; and (c) therapeutically effective amounts of at least other anti-cancer agent(s).

In still further embodiments, the animals or patients to be treated by the present invention are further subjected to surgery or radiotherapy, or are provided with a therapeutically effective amount of at least a first anti-cancer agent. The "at least a first anti-cancer agent" in this context means "at least a first anti-cancer agent in addition to the naked anti-aminophospholipid antibody" (preferably anti-phosphatidylserine or anti-phosphatidylethanolamine). The "at least a first anti-cancer agent" may thus be considered to be "at least a second anti-cancer agent", where the naked anti-aminophospholipid antibody is a first anti-cancer agent. However, this is purely a matter of semantics, and the practical meaning will be clear to those of ordinary skill in the art.

The at least a first anti-cancer agent may be administered to the animal or patient substantially simultaneously with the anti-aminophospholipid antibody, or antigen-binding fragment thereof; such as from a single pharmaceutical composition or from two pharmaceutical compositions administered closely together.

Alternatively, the at least a first anti-cancer agent may be administered to the animal or patient at a time sequential to the administration of the at least a first anti-aminophospholipid antibody, or antigen-binding fragment thereof. "At a time sequential", as used herein, means "staggered", such that the at least a first anti-cancer agent is administered to the animal or patient at a time distinct to the administration of the at least a first anti-aminophospholipid antibody. Generally, the two agents are administered at times effectively spaced apart to allow the two agents to exert their respective therapeutic effects, i.e., they are administered at "biologically effective time intervals".

The at least a first anti-cancer agent may be administered to the animal or patient at a biologically effective time prior to the anti-aminophospholipid antibody or fragment thereof, or at a biologically effective time subsequent to the anti-aminophospholipid antibody fragment. Administration of one or more non-aminophospholipid targeted anti-cancer agents at a therapeutically effective time subsequent to an anti-aminophospholipid antibody may be particularly desired wherein the anti-cancer agent is an anti-tumor cell immunotoxin designed to kill tumor cells at the outermost rim of the tumor, and/or wherein the anti-cancer agent is an anti-angiogenic agent designed to prevent micrometastasis of any remaining tumor cells. Such considerations will be known to those of skill in the art.

Administration of one or more non-aminophospholipid targeted anti-cancer agents at a therapeutically effective time prior to an anti-aminophospholipid antibody may be particularly employed where the anti-cancer agent is designed to increase aminophospholipid expression. This may be achieved by using anti-cancer agents that injure, or induce apoptosis in, the tumor endothelium. Exemplary anti-cancer agent include, e.g., taxol, vincristine, vinblastine, neomycin, combretastatin(s), podophyllotoxin(s), TNF-α, angiostatin, endostatin, vasculostatin, $\alpha_v\beta_3$ antagonists, calcium ionophores, calcium-flux inducing agents, any derivative or prodrug thereof.

The one or more additional anti-cancer agents may be chemotherapeutic agents, radiotherapeutic agents, cytokines, anti-angiogenic agents, apoptosis-inducing agents or anti-cancer immunotoxins or coaguligands. "Chemotherapeutic agents", as used herein, refer to classical chemotherapeutic agents or drugs used in the treatment of malignancies. This term is used for simplicity notwithstanding the fact that other compounds may be technically described as chemotherapeutic agents in that they exert an anti-cancer effect. However, "chemotherapeutic" has come to have a distinct meaning in the art and is being used according to this standard meaning.

A number of exemplary chemotherapeutic agents are described herein. Those of ordinary skill in the art will readily understand the uses and appropriate doses of chemotherapeutic agents, although the doses may well be reduced when used in combination with the present invention. A new class of drugs that may also be termed "chemotherapeutic agents" are agents that induce apoptosis. Any one or more of such drugs, including genes, vectors and antisense constructs, as appropriate, may also be used in conjunction with the present invention.

Anti-cancer immunotoxins or coaguligands are further appropriate anti-cancer agents. "Anti-cancer immunotoxins or coaguligands", or targeting-agent/therapeutic agent constructs, are based upon targeting agents, including antibodies or antigen binding fragments thereof, that bind to a targetable component of a tumor cell, tumor vasculature or tumor stroma, and that are operatively attached to a therapeutic agent, generally a cytotoxic agent (immunotoxin) or coagulation factor (coaguligand). A "targetable component" of a tumor cell, tumor vasculature or tumor stroma, is preferably a surface-expressed, surface-accessible or surface-localized component, although components released from necrotic or otherwise damaged tumor cells or vascular endothelial cells may also be targeted, including cytosolic and/or nuclear tumor cell antigens.

Both antibody and non-antibody targeting agents may be used, including growth factors, such as VEGF and FGF; peptides containing the tripeptide R-G-D, that bind specifically to the tumor vasculature; and other targeting components such as annexins and related ligands.

Anti-tumor cell immunotoxins or coaguligands may comprise antibodies exemplified by the group consisting of B3 (ATCC HB 10573), 260F9 (ATCC HB 8488), D612 (ATCC HB 9796) and KS1/4, said KS1/4 antibody obtained from a cell comprising the vector pGKC2310 (NRRL B-18356) or the vector pG2A52 (NRRL B-18357).

Anti-tumor stroma immunotoxins or coaguligands will generally comprise antibodies that bind to a connective tissue component, a basement membrane component or an activated platelet component; as exemplified by binding to fibrin, RIBS or LIBS.

Anti-tumor vasculature immunotoxins or coaguligands may comprise ligands, antibodies, or fragments thereof, that bind to a surface-expressed, surface-accessible or surface-localized component of the blood transporting vessels, preferably the intratumoral blood vessels, of a vascularized tumor. Such antibodies include those that bind to surface-expressed components of intratumoral blood vessels of a vascularized tumor, including aminophospholipids themselves, and intratumoral vasculature cell surface receptors, such as endoglin (TEC-4 and TEC-11 antibodies), a TGFβ receptor, E-selectin, P-selectin, VCAM-1, ICAM-1, PSMA, a VEGF/VPF receptor, an FGF receptor, a TIE, $\alpha_v\beta_3$ integrin, pleiotropin, endosialin and MHC Class II proteins. The antibodies may also bind to cytokine-inducible or coagulant-inducible components of intratumoral blood vessels.

Other anti-tumor vasculature immunotoxins or coaguligands may comprise antibodies, or fragments thereof, that bind to a ligand or growth factor that binds to an intratumoral vasculature cell surface receptor. Such antibodies include those that bind to VEGF/VPF (GV39 and GV97 antibodies), FGF, TGFβ, a ligand that binds to a TIE, a tumor-associated fibronectin isoform, scatter factor/hepatocyte growth factor (HGF), platelet factor 4 (PF4), PDGF and TIMP. The antibodies, or fragments thereof, may also bind to a ligand:receptor complex or a growth factor:receptor complex, but not to the ligand or growth factor, or to the receptor, when the ligand or growth factor or the receptor is not in the ligand:receptor or growth factor:receptor complex.

Anti-tumor cell, anti-tumor stroma or anti-tumor vasculature antibody-therapeutic agent constructs may comprise anticellular, cytostatic or cytotoxic agents such as plant-, fungus- or bacteria-derived toxins (immunotoxins). Ricin A chain and deglycosylated ricin A chain will often be preferred, and gelonin and angiopoietins are also contemplated. Anti-tumor cell, anti-tumor stroma or anti-tumor vasculature antibody-therapeutic agent constructs may comprise coagulation factors or second antibody binding regions that bind to coagulation factors (coaguligands). The operative association with Tissue Factor or Tissue Factor derivatives, such as truncated Tissue Factor, will often be preferred.

The present invention yet further provides a series of novel therapeutic kits, medicaments and/or cocktails for use in conjunction with the methods of the invention. The kits, medicaments and/or cocktails generally comprise a combined effective amount of an anti-cancer agent and an antibody, or an antigen-binding fragment thereof, that binds to an aminophospholipid, preferably phosphatidylserine or phosphatidylethanolamine.

Where the primary purpose of a kit of the invention is in combination therapy, the kit may nonetheless still further comprise an imaging component, generally a diagnostically effective amount of a detectably-labeled aminophospholipid binding construct, such as a labeled anti-aminophospholipid antibody or antigen binding fragment thereof.

The kits and medicaments will comprise, preferably in suitable container means, a biologically effective amount of at least a first antibody, or an antigen-binding fragment thereof, that binds to an aminophospholipid, preferably phosphatidylserine or phosphatidylethanolamine; in combination with a biologically effective amount of at least a first anti-cancer agent. The components of the kits and medicaments may be comprised within a single container or container means, or comprised within distinct containers or container means. The cocktails will generally be admixed together for combined use.

The entire range of anti-aminophospholipid antibodies, as described above, may be employed in the kits, medicaments and/or cocktails, with anti-PS, anti-PE, human, humanized and monoclonal antibodies, or fragments thereof, being preferred. The anti-cancer agents are also those as described above, including chemotherapeutic agents, radiotherapeutic agents, anti-angiogenic agents, apoptopic agents, immunotoxins and coaguligands. Agents formulated for intravenous administration will often be preferred.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. Binding of anti-VCAM-1.tTF coaguligand to unstimulated (control) and IL-1α-activated bEnd.3 cells. FIG. 1B. Generation of factor Xa by cell-bound anti-VCAM-1.tTF coaguligand.

DESCRIPTION OF ILLUSTRATIVE EMBODIMENTS

A. Tumor Destruction using VCAM-1 Coaguligand

Figure 1A:
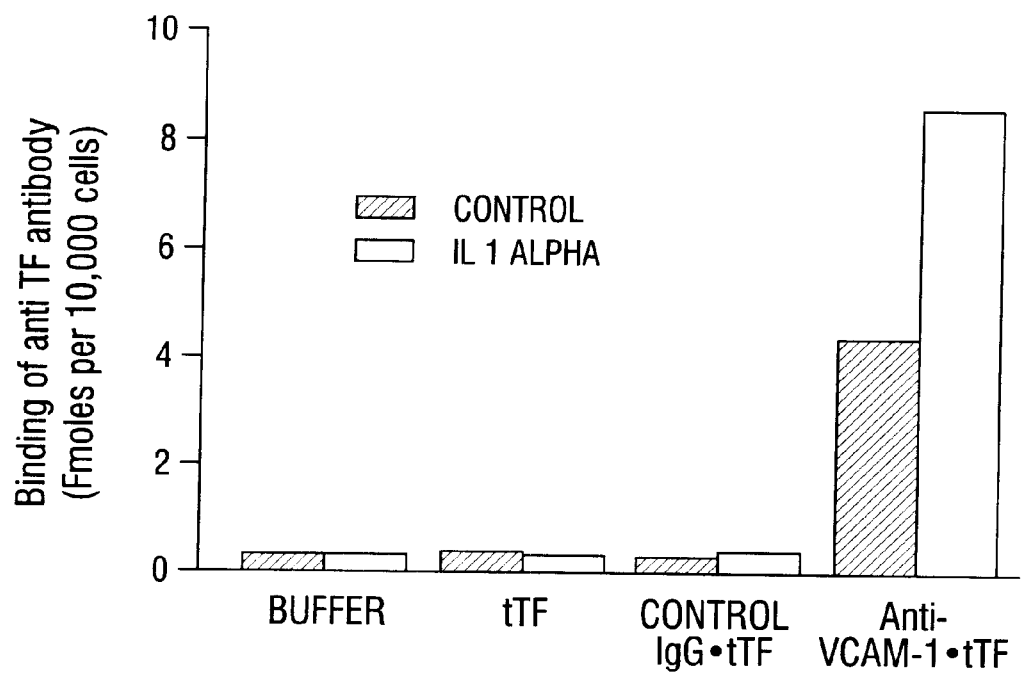
FIG. 1A and FIG. 1B. Activity of cell-bound anti-VCAM-1.tTF in vitro.

Solid tumors and carcinomas account for more than 90% of all cancers in man. Although the use of monoclonal antibodies and immunotoxins has been investigated in the therapy of lymphomas and leukemias (Vitetta et al., 1991), these agents have been disappointingly ineffective in clinical trials against carcinomas and other solid tumors (Abrams and Oldham, 1985). A principal reason for the ineffectiveness of antibody-based treatments is that macromolecules are not readily transported into solid tumors. Even once within a tumor mass, these molecules fail to distribute evenly due to the presence of tight junctions between tumor cells, fibrous stroma, interstitial pressure gradients and binding site barriers (Dvorak et al., 1991).

In developing new strategies for treating solid tumors, the methods that involve targeting the vasculature of the tumor, rather than the tumor cells, offer distinct advantages. An effective destruction or blockade of the tumor vessels arrests blood flow through the tumor and results in an avalanche of tumor cell death. Antibody-toxin and antibody-coagulant constructs have already been used to great effect in the specific targeting and destruction of tumor vessels, resulting in tumor necrosis (Burrows et al., 1992; Burrows and Thorpe, 1993; WO 93/17715; WO 96/01653; Huang et al., 1997; each incorporated herein by reference).

Tumor vasculature-targeted cytotoxic agents are described in the following patents and patent applications: U.S. Pat. Nos. 5,855,866; 5,776,427; 5,863,538; 5,660,827; 6,004,554; 5,965,132 and 6,051,230; and U.S. application Ser. No. 07/846,349; each incorporated herein by reference. Tumor targeted coagulants are the following patents and patent applications: U.S. Pat. Nos. 5,855,866; 5,877,289; 5,965,132; 6,004,555; 6,036,955; and 6,093,399; and U.S. application Ser. No. 07/846,349); each incorporated herein by reference.

Where antibodies, growth factors or other binding ligands are used to specifically deliver a coagulant to the tumor vasculature, such agents are termed "coaguligands". A currently preferred coagulant for use in coaguligands is truncated Tissue Factor (tTF) (Huang et al., 1997; WO 96/01653; U.S. Pat. No. 5,877,289. TF is the major initiator of blood coagulation (Ruf et al., 1991). At sites of injury, Factor VII/VIIa in the blood comes into contact with, and binds to, TF on cells in the perivascular tissues. The TF:VIIa complex, in the presence of the phospholipid surface, activates factors IX and X. This, in turn, leads to the formation of thrombin and fibrin and, ultimately, a blood clot (Ruf and Edgington, 1994).

The recombinant, truncated form of tissue factor (tTF), lacking the cytosolic and transmembrane domains, is a soluble protein that has about five orders of magnitude lower coagulation inducing ability than native TF (Stone et al., 1995; Huang et al., 1997). This is because TF needs to be associated with phospholipids for the complex with VIIa to activate IXa or Xa efficiently. However, when tTF is delivered to tumor vascular endothelium by means of a targeting antibody or agent, it is brought back into proximity to a lipid surface and regains thrombogenic activity (Huang et al., 1997; U.S. Pat. Nos. 5,877,289, 6,004,555 and 6,093,399. A coaguligand is thus created that selectively thromboses tumor vasculature.

Truncated TF has several advantages that commend its use in vascular targeted coaguligands: human tTF is readily available, and the human protein will have negligible or low immunogenicity in man; human tTF is fully functional in experimental animals, including mice; and targeted tTF is highly potent because it triggers the activation of a cascade of coagulation proteins, giving a greatly amplified effect (U.S. Pat. Nos. 5,877,289, 6,044,555 and 6,093,399.

A range of suitable target molecules that are available on tumor endothelium, but largely absent from normal endothelium, have been described. For example, expressed targets may be utilized, such as endoglin, E-selectin, P-selectin, VCAM-1, ICAM-1, PSMA, a TIE, a ligand reactive with LAM-1, a VEGF/VPF receptor, an FGF receptor, $\alpha_v\beta_3$ integrin, pleiotropin or endosialin (U.S. Pat. Nos. 5,855,866 5,877,289; Burrows et al., 1992; Burrows and Thorpe, 1993; Huang et al., 1997; Liu et al., 1997; Ohizuni et al., 1997; each incorporated herein by reference).

Adsorbed targets are another suitable group, such as VEGF, FGF, TGFβ, HGF, PF4, PDGF, TIMP, a ligand that binds to a TIE or a tumor-associated fibronectin isoform (U.S. Pat. Nos. 5,877,289, 5,965,132 and 6,044,555; each incorporated herein by reference). Fibronectin isoforms are ligands that bind to the integrin family of receptors. Tumor-associated fibronectin isoforms are targetable components of both tumor vasculature and tumor stroma. The monoclonal antibody BC-1 (Carnemolla et al., 1989) specifically binds to tumor-associated fibronectin isoforms.

Other targets inducible by the natural tumor environment or following intervention by man are also targetable entities, as described in U.S. Pat. Nos. 5,776,427, 5,863,538 and 6,036,955 (each incorporated herein by reference). When used in conjunction with prior suppression in normal tissues and tumor vascular induction, MHC Class II antigens may also be employed as targets (U.S. Pat. Nos. 5,776,427; 5,863,538; 6,044,554 and 6,036,955 each incorporated herein by reference).

One currently preferred target for clinical applications is vascular endothelial adhesion molecule-1 (VCAM-1) (U.S. Pat. Nos. 5,855,866, 5,877,289, 6,004,555 and 6,093,399 each incorporated herein by reference). VCAM-1 is a cell adhesion molecule that is induced by inflammatory cytokines IL-1α, IL-4 (Thornhill et al., 1990) and TNFα (Munro, 1993) and whose role in vivo is to recruit leukocytes to sites of acute inflammation (Bevilacqua, 1993).

VCAM-1 is present on vascular endothelial cells in a number of human malignant tumors including neuroblastoma (Patey et al., 1996), renal carcinoma (Droz et al., 1994), non-small lung carcinoma (Staal-van den Brekel et al., 1996), Hodgkin's disease (Patey et al., 1996), and angiosarcoma (Kuzu et al., 1993), as well as in benign tumors, such as angioma (Patey et al., 1996) and hemangioma (Kuzu et al., 1993). Constitutive expression of VCAM-1 in man is confined to a few vessels in the thyroid, thymus and kidney (Kuzu et al., 1993; Bruijn and Dinklo, 1993), and in the mouse to vessels in the heart and lung (Fries et al., 1993).

Certain of the data presented herein even further supplement those provided in U.S. Pat. Nos. 5,855,855 and 5,877,289 and 6,004,555 each incorporated herein by reference) and show the selective induction of thrombosis and tumor infarction resulting from administration of an anti-VCAM-1.tTF coaguligand. The results presented were generated using mice bearing L540 human Hodgkin lymphoma. When grown as a xenograft in SCID mice, this tumor shows close similarity to the human disease with respect to expression of inflammatory cytokines (Diehl et al., 1985) and the presence of VCAM-1 and other endothelial cell activation molecules on its vasculature.

Using a covalently-linked anti-VCAM-1.tTF coaguligand, in which tTF was directly linked to the anti-VCAM-1 antibody, it is shown herein that the coaguligand localizes selectively to tumor vessels, induces thrombosis of those vessels, causes necrosis to develop throughout the tumor and retards tumor growth in mice bearing solid L540 Hodgkin tumors. Tumors generally needed to be at least about 0.3 cm in diameter to respond to the coaguligand, because VCAM-1 was absent from smaller tumors. Presumably, in small tumors, the levels of cytokines secreted by tumor cells or host cells that infiltrate the tumor are too low for VCAM-1 induction. This is in accordance with the studies in U.S. Pat. Nos. 5,855,866, 5,877,289, 5,776,427, 6,004,555 and 6,036,955, where the inventions were shown to be most useful in larger solid tumors.

Although VCAM-1 staining was initially observed more in the periphery of the tumor, the coaguligand evidently bound to and occluded blood transporting vessels—as it was capable of curtailing blood flow in all tumor regions. Furthermore, one of the inventors contemplates that the thrombin generation caused by the initial administration of the coaguligand likely leads to further VCAM-1 induction on central vessels (Sluiter et al., 1993), resulting in an amplified signal and evident destruction of the intratumoral region. This type of coagulant-induced expression of further targetable markers, and hence signal amplification, is also disclosed in U.S. Ser. No. 08/481,904 and U.S. Pat. No. 6,036,955.

B. Mechanism of VCAM-1-Targeted Tumor Destruction

As shown herein, although localization to VCAM-1-expressing vessels in the heart and lungs of mice was observed upon administration of an anti-VCAM-1 coaguligand, this construct did not induce thrombosis in such non-tumor sites. Furthermore, the anti-VCAM-1 coaguligand was no more toxic to mice than was a control coaguligand of irrelevant specificity, again indicating that the constitutive expression of VCAM-1 on heart and lung vessels did not lead to toxicity. This data is important to the immediate clinical progress of coaguligand therapy, given that VCAM-1 is a naturally occurring marker of tumor vascular endothelium in humans. However, this phenomenon also provided the inventors with a unique insight, leading to a totally different approach to tumor vasculature destruction.

The inventors sought to understand the mechanism behind the ability of the anti-VCAM-1 coaguligand to bind to the VCAM-1 constitutively expressed on blood vessels in the heart and lungs, and yet not to cause thrombosis in those vessels. There are numerous scientific possibilities for this empirical observation, generally connected with the prothrombotic nature of the tumor environment any fibrinolytic predisposition in the heart and lungs.

Generally, there is a biological equilibrium between the coagulation system (fibrin deposition) and the fibrinolytic system (degradation of fibrin by enzymes). However, in malignant disease, particularly carcinomas, this equilibrium is disrupted, resulting in the abnormal activation of coagulation (hypercoagulability or the "prothrombotic state"). Evidence also indicates that various components of these pathways may contribute to the disorderly characteristics of malignancy, such as proliferation, invasion, and metastasis (Zacharski et al., 1993).

Donati (1995) reviewed the complex interplay between the original clinical observations of thrombotic complications of malignant diseases, and the subsequent progress in the cell biology and biochemistry of tumor cell activities. However, despite extensive research, a clear molecular explanation for the prothrombotic nature of the tumor environment could not be provided (Donati, 1995). Donati did emphasize, though, the role of tumor cells in this process. It was explained that tumor cells express procoagulant activities, such as tissue thromboplastin and cancer procoagulant (CP) (Donati, 1995). WO 91/07187 also reported a procoagulant activity of tumor cells.

Numerous other studies have also identified the tumor cells themselves as being responsible for the prothrombotic state within a tumor. For example, Nawroth et al. (1988) reported that factor(s) elaborated by sarcoma cells enhance the procoagulant response of nearby endothelium to TNF. These authors reported that fibrin formation occurred throughout the tumor vascular bed 30 minutes after TNF infusion, but that fibrin deposition and platelet aggregates were not observed in normal vasculature (Nawroth et al., 1988). TNF was later shown to enhance the expression of tissue factor on the surface of endothelial cells (Murray et al., 1991). This was proposed to explain earlier studies showing that cultured endothelial cells incubated with recombinant TNF have enhanced procoagulant activity, tissue factor, and concomitant suppression of the protein C pathway, an anti-thrombotic mechanism that functions on the surface of quiescent endothelial cells (Nawroth et al., 1985; Nawroth and Stem, 1986).

Data from Sugimura et al. (1994) also implicated tumor cells as the key components of the procoagulant activity of the tumor. It was reported that four tumor cell lines were able to support different stages of the extrinsic pathway of coagulation (Sugimura et al., 1994). Another study reported that a human ovarian carcinoma cell line, OC-2008, constitutively expressed surface membrane Tissue Factor activity and exhibited cell surface-dependent prothrombinase complex activity (Rao et al., 1992). Connor et al. (1989) further suggested that it is the pathologic cells that control coagulation. Their results indicated that tumorigenic, undifferentiated murine erythroleukemic cells exhibit a 7- to 8-fold increase in the potency of their procoagulant activity (Connor et al., 1989).

Zacharski et al. (1993) also focused on tumor cells and sought to define the mode of interaction of ovarian carcinoma cells with the coagulation (procoagulant-initiated) and fibrinolysis (urokinase-type plasminogen activator-initiated, u-PA) pathways. They reported that tumor cells expressed Tissue Factor and coagulation pathway intermediates that resulted in local thrombin generation—as evidenced by the conversion of fibrinogen, present in tumor connective tissue, to fibrin that was found to hug the surfaces of tumor nodules and individual tumor cells. Detected fibrin could not be accounted for on the basis of necrosis or a local inflammatory cell infiltrate (Zacharski et al., 1993). These authors concluded that there exists a dominant tumor cell-associated procoagulant pathway that leads to thrombin generation and hypercoagulability.

Other hypotheses have proposed that it is changes in the tumor blood vessels that render these vessels better able to support the formation of thrombi and/or less able to dissolve fibrin. For example, tumor vessels have been reported to exhibit upregulation of Tissue Factor, down-regulation of plasminogen activators and/or upregulation of the inhibitor of plasminogen activators, PAI-1 (Nawroth and Stem, 1986; Nawroth et al., 1988). Such effects are believed to be magnified by tumor derived factors (Murray et al., 1991; Ogawa et al., 1990), possibly VEGF.

For example, Ogawa et al. (1990) reported that hypoxia caused endothelial cell surface coagulant properties to be shifted to promote activation of coagulation. This was accompanied by suppression of the anticoagulant cofactor, thrombomodulin, and induction of an activator of factor X, distinct from the classical extrinsic and intrinsic systems (Ogawa et al., 1990). Also, there could be an increase in the local concentration of Factors VIIa, IXa, Xa, or other molecules that interact with TF, within the tumor vessels, thus encouraging thrombosis.

Additionally, platelets are a major component of any procoagulant state. Recently, the procoagulant potential of platelets has been linked to their ability to shed procoagulant microparticles from the plasma membrane (Zwaal et al., 1989; 1992; Dachary-Prigent et al., 1996). It has been proposed that an increased proportion of circulating microparticles, vesicles or membrane fragments from platelets contributes to 'prethrombotic' (prothrombotic) states in various pathological conditions (Zwaal et al., 1989; 1992; Dachary-Prigent et al., 1996, pp. 159 and references cited therein). McNeil et al. (1990) also reported that $\beta_2$-GPI exerts multiple inhibitory effects on coagulation and platelet aggregation. Tumor platelet biology could thus explain the effectiveness of the anti-VCAM-1 coaguligand.

Further tenable explanations included the simple possibility that VCAM-1 is expressed at higher levels in tumor vessels than on blood vessels in the heart and lungs, probably due to induction by tumor-derived cytokines, and that binding to the healthy vessels cannot tip the balance into sustained thrombosis. Also the fibrinolytic mechanisms could be upregulated in the heart, as exemplified by increased Tissue Factor pathway inhibitor (TFPI), increased plasminogen activators, and/or decreased plasminogen activator inhibitors. Should the fibrinolytic physiology of the heart and lung vessels prove to be the major reason underlying the tumor-specific effects of the anti-VCAM-1 coaguligand, this would generally preclude the development of additional anti-tumor therapies targeted to unique aspects of tumor biology.

Despite all the possible options, the inventors reasoned that the failure of the anti-VCAM-1 coaguligand to cause thrombosis in vessels of normal tissues was due to the absence of the aminophospholipid, phosphatidylserine (PS), from the luminal surface of such vessels. To complete the theory, therefore, not only would phosphatidylserine have to be shown to be absent from these normal vessels, but its presence on the luminal side of tumor-associated vessels would have to be conclusively demonstrated.

The inventors therefore used immunohistochemical staining to evaluate the distribution of a monoclonal anti-phosphatidylserine (anti-PS) antibody injected intravenously into tumor-bearing mice. These studies revealed that the VCAM-1 expressing vessels in the heart and lungs lacked PS, whereas the VCAM-1 expressing vessels in the tumor expressed PS. The need for surface PS expression in coaguligand action is further indicated by the inventors' finding that annexin V, which binds to PS, blocks anti-VCAM-1.tTF coaguligand action, both in vitro and in vivo.

The lack of thrombotic effect of the anti-VCAM-1 coaguligand on normal heart and lung vessels can thus be explained, at least in part: the absence of the aminophospholipid, phosphatidylserine, means that the normal vessels lack a procoagulant surface upon which coagulation complexes can assemble. In the absence of surface PS, anti-VCAM-1.tTF binds to VCAM-1 expressing heart and lung vessels, but cannot induce thrombosis. In contrast, VCAM-1 expressing vessels in the tumor show coincident expression of surface PS. The coaguligand thus binds to tumor vessels and activates coagulation factors locally to form an occlusive thrombus.

In addition to delineating the tumor-specific thrombotic effects of anti-VCAM-1 coaguligands, the specific expression of the aminophospholipid, phosphatidylserine, on the luminal surface of tumor blood vessels also allowed the inventors to explain the prothrombotic phenotype observed, but not understood, in earlier studies (Zacharski et al., 1993; Donati, 1995). Rather than being predominantly due to tumor cells or elaborated factors; platelets, procoagulant microparticles or membrane fragments; or due to imbalances in thromboplastin, thrombomodulin, cancer procoagulant, Tissue Factor, protein C pathway, plasminogen activators or plasminogen activator inhibitors (e.g., PAI-1), the inventors' studies indicate that it is PS expression that plays a significant role in the prothrombotic state of tumor vasculature.

C. Aminophospholipids as Markers of Tumor Vasculature

Following their discovery that the representative aminophospholipid, phosphatidylserine, was specifically expressed on the luminal surface of tumor blood vessels, but not in normal blood vessels, the inventors reasoned that aminophospholipids had potential as targets for therapeutic intervention. The present invention therefore encompasses targeting the aminophospholipid constituents, particularly phosphatidylserine (PS) and phosphatidylethanolamine (PE), in tumor treatment. Although anti-tumor effects from aminophospholipid targeting are demonstrated herein, using art-accepted animal models, the ability of aminophospholipids to act as safe and effective targetable markers of tumor vasculature could not have been predicted from previous studies.

For example, although tumor vessels are generally prothrombotic in nature, as opposed to other blood vessels, it is an inherent property of the tumor to maintain a network of blood vessels in order to deliver oxygen and nutrients to the tumor cells. Evidently, tumor-associated blood vessels cannot be so predisposed towards thrombosis that they spontaneously and readily support coagulation, as such coagulation would necessarily cause the tumor to self-destruct. It is thus unexpected that any thrombosis-associated tumor vessel marker, such as the presently identified phosphatidylserine, could be discovered that is expressed in quantities sufficient to allow effective therapeutic intervention by targeting, and yet is expressed at levels low enough to ordinarily maintain blood flow through the tumor.

The present identification of aminophospholipids as safe and effective tumor vasculature targets is even more surprising given (1) the previous speculations regarding the role of other cell types and/or various factors, activators and inhibitors underlying the complex, prothrombotic state of the tumor (as discussed above); and (2) the confusing and contradictory state of the art concerning aminophospholipid biology, in terms of both expression and function in various cell types.

Phosphatidylserine and phosphatidylethanolamine are normally segregated to the inner surface of the plasma membrane bilayer in different cells (Gaffet et al., 1995; Julien et al., 1995). In contrast, the outer leaflet of the bilayer membrane is rich in phosphatidylcholine analogs (Zwaal et al., 1989; Gaffet et al., 1995). This lipid segregation creates an asymmetric transbilayer. Although the existence of membrane asymmetry has been discussed for some time, the reason for its existence and the mechanisms for its generation and control are poorly understood (Williamson and Schlegel, 1994), particularly in cells other than platelets.

There are even numerous conflicting reports regarding the presence or absence of PS and PE in different cells and tissues, let alone concerning the likely role that these aminophospholipids may play. For example, the many PS studies conducted with platelets, key components in blood coagulation (Dachary-Prigent et al., 1996), have yielded highly variable results. Bevers et al. (1982) measured the platelet prothrombin-converting activity of non-activated platelets after treatment with various phospholipases or proteolytic enzymes. They concluded that negatively charged phosphatidylserine, and possibly phosphatidylinositol, were involved in the prothrombin-converting activity of non-activated platelets (Bevers et al., 1982).

Bevers et al. (1983) then reported an increased exposure of phosphatidylserine, and a decreased exposure of sphingomyelinase, in activated platelets. However, these alterations were much less apparent in platelets activated either by thrombin or by collagen alone, in contrast to collagen plus thrombin, diamide, or a calcium ionophore (Bevers et al., 1983). The surface expression of PS in response to diamide was contradicted by studies in erythrocytes, which showed no diamide-stimulated PS exposure (de Jong e tal., 1997). While echoing their earlier results, Bevers and colleagues then later reported that changes in the plasma membrane-cytoskeleton interaction, particularly increased degradation of cytoskeletal actin-binding protein, was important to platelet surface changes (Bevers et al., 1985; pages 368–369).

Maneta-Peyret et al. (1989) also reported the detection of PS on human platelets. These authors noted that the platelet procoagulant surface could be formed by negatively charged phospholipids, such as phosphatidylserine and phosphatidylethanolamine (generally neutral or zwitterionic), or both. The role of phosphatidylserine in the process of coagulation has been questioned in favor of phosphatidylethanolamine (Maneta-Peyret et al., 1989; Schick et al., 1976; 1978). For example, studies have reported that 18% of phosphatidylethanolamine becomes surface-accessible after 2 hours, in contrast to zero phosphatidylserine (Schick et al., 1976).

Ongoing studies with platelets were also reported as showing a further 16% increase in phosphatidylethanolamine exposure after thrombin treatment, with no increase in the phosphatidylserine levels (Schick et al., 1976). Therefore, PS was said not to be a component of the functional surface of the platelet plasma membrane (Schick et al., 1976; 1978). Nonetheless, current evidence does seem to indicate that both PS and PE are involved in the phospholipid asymmetry observed in the outer membrane of platelets and erythrocytes, and that PS is involved in the procoagulant activity of platelets (Gaffet et al., 1995; de Jong et al., 1997; U.S. Pat. No. 5,627,036).

The mechanisms for achieving and maintaining differential aminophospholipid distribution, let alone the functional significance of doing so, have long been the subject of controversial speculations. In reviewing the regulation of transbilayer phospholipid movement, Williamson and Schlegel (1994) indicated that elevating intracellular $Ca^{2+}$ allows the major classes of phospholipids to move freely across the bilayer, scrambling lipids and dissipating asymmetry. de Jong et al. (1997) also reported that an increase of intracellular calcium leads to a rapid scrambling of the lipid bilayer and the exposure of PS, which could be partially inhibited by cellular oxidation. The interaction of aminophospholipids with cytoskeletal proteins has also been proposed as a mechanism for regulating membrane phospholipid asymmetry (Zwaal et al., 1989).

Gaffet et al. (1995) stated that the transverse redistribution of phospholipids during human platelet activation is achieved by a vectorial outflux of aminophospholipids, not counterbalanced by a rapid reciprocal influx of choline head phospholipids, i.e. not scrambling. They suggested that the specific vectorial outflux of aminophospholipids could be catalyzed by a "reverse aminophospholipid translocase" activity (Gaffet et al., 1995). An alternative hypothesis would be that the activity of an inward translocase was inhibited. Zwaal et al. (1989) proposed the involvement of a phospholipid-translocase that catalyzed both the outward and inward movement of aminophospholipids.

The presence of an energy- and protein-dependent aminophospholipid translocase activity that transports phosphatidylethanolamine from the outer to the inner leaflet of the lipid bilayer was reported by Julien et al. (1993). They then showed that the aminophospholipid translocase activity could also transfer phosphatidylserine, and that the activity could be maintained, suppressed and restored depending on the conditions of cell incubation (Julien et al., 1993), and inhibited by the tumor promoter, 12-O-tetradecanoylphorbol-13-acetate (TPA) (Julien et al., 1997).

A 35 kD phospholipid scramblase that promotes the $Ca^{2+}$-dependent bidirectional movement of phosphatidylserine and other phospholipids was recently cloned from a cDNA library (Zhou et al., 1997). This "PL scramblase" protein is a proline-rich, type II plasma membrane protein with a single transmembrane segment near the C terminus. Subsequent studies confirmed that this protein was responsible for the rapid movement of phospholipids from the inner to the outer plasma membrane leaflets in cells exposed to elevated cytosolic calcium concentrations (Zhao et al., 1998).

The aminophospholipid translocase activity reported by Julien et al. (1993; 1997), which transports PS and PE from the outer to the inner leaflet, is different to the bidirectional $Ca^{2+}$-dependent scramblase (Zhou et al., 1997; Zhao et al., 1998). The scramblase is activated by $Ca^{2+}$, and mostly functions to move PS from the inner to the outer leaflet in response to increased $Ca^{2+}$ levels. It is now generally believed that the aminophospholipid translocase maintains membrane asymmetry during normal conditions, but that the scramblase is activated by $Ca^{2+}$ influx, over-riding the translocase and randomizing aminophospholipid distribution.

The normal segregation of PS and PE to the inner surface of the plasma membrane is thus now generally accepted, and certain membrane components involved in the asymmetric processes have even been identified. However, doubts remain about the conditions, mechanisms and cell types that are capable of re-locating aminophospholipids to the outer leaflet of the membrane, and the biological implications of such events.

Contradictory reports concerning aminophospholipid expression are not limited to studies of platelets. Phosphatidylserine and phosphatidylethanolamine are generally about 7% and about 10%, respectively, of the phospholipid composition of cultured human endothelial cells from human artery, saphenous and umbilical vein (7.1% and 10.2%, respectively; Murphy et al., 1992). However, an important example of the contradictions in the literature concerns the ability of anti-PS antibodies to bind to endothelial cells (Lin et al., 1995).

The anti-PS antibodies present in recurrent pregnancy loss (Rote et al., 1995; Rote, 1996; Vogt et al., 1996; Vogt et al., 1997) were believed to modulate endothelial cell function, without evidence of binding to endothelial cells. In an attempt to explain this discrepancy, Lin et al. (1995) tried but failed to demonstrate anti-PS antibody binding to resting endothelial cells. They concluded that PS antigenic determinants are not expressed on the surface of resting endothelial cells, although a PS-dependent antigenic determinant was associated with cytoskeletal-like components in acetone-fixed cells (Lin et al., 1995).

Van Heerde et al. (1994) reported that vascular endothelial cells in vitro can catalyze the formation of thrombin by the expression of binding sites at which procoagulant complexes can assemble. In contrast to other studies with activated platelets (Bevers et al., 1982; 1983; 1985; Maneta-Peyret et al., 1989; Schick et al., 1976; 1978), stimulated HUVEC endothelial cells did not exhibit an increase in PS binding sites as compared to quiescent cells (Van Heerde et al., 1994). Phosphatidylserine was reported to be necessary for Factor Xa formation via the extrinsic as well as the intrinsic route (Van Heerde et al., 1994). Nonetheless, Brinkman et al. (1994) published contradictory results, indicating that other membrane constituents besides negatively charged phospholipids are involved in endothelial cell mediated, intrinsic activation of factor X.

Ravanat et al. (1992) also studied the catalytic potential of phospholipids in pro- and anti-coagulant reactions in purified systems and at the surface of endothelial cells in culture after stimulation. Their seemingly contradictory results were proposed to confirm a role for phospholipid-dependent mechanisms in both procoagulant Tissue-Factor activity and anticoagulant activities (activation of protein C by the thrombin-thrombomodulin complex and by Factor Xa) (Ravanat et al., 1992). The Ravanat et al. (1992) results were also said to provide evidence of phospholipid exposure during activation of human endothelial cells, which was not observed by Van Heerde et al. (1994) or Brinkman et al. (1994). However, they did note that anionic phospholipids are of restricted accessibility in the vicinity of cellular Tissue Factor. The situation is further complicated as, even after Tissue Factor induction, other events are likely necessary for coagulation, as the Tissue Factor remains inaccessible, being under the cell.

Ravanat et al. (1992) went on to suggest that the different extent of inhibition of Tissue Factor and thrombomodulin activities on stimulated endothelial cells means that the cofactor environments differ for the optimal expression of these opposite cellular activities. However, the acknowledged difficulties in trying to reproduce exact cellular phospholipid environments (Ravanat et al., 1992), raise the possibility of artifactual data from these in vitro studies. Indeed, irrespective of the Ravanat et al. (1992) data, it is generally acknowledged that meaningful information regarding tumor biology, and particularly therapeutic intervention, can only be gleaned from in vivo studies in tumor-bearing animals, such as those conducted by the present inventors.

In addition to the disagreements regarding aminophospholipid expression, as discussed above, there are also conflicting reports concerning the function of aminophospholipids in various cell types. Although it is now generally accepted that PS expression on activated platelets is connected with the procoagulant surface, in discussing the physiological significance of membrane phospholipid asymmetry in platelets and red blood cells, Zwaal et al. (1989) highlighted other important functions. Moreover, Toti et al. (1996) stated that the physiological implications of a loss of asymmetric phospholipid distribution remain poorly understood in cell types other than blood cells.

Zwaal et al. (1989) stated that the membrane phospholipid asymmetry of platelets and red cells is undone when the cells are activated in various ways, presumably mediated by the increased transbilayer movement of phospholipids. These changes, coupled with the release of shed microparticles, were explained to play a role in local blood clotting reactions. A similar phenomenon was described to occur in sickled red cells: phospholipid vesicles breaking off from reversibly sickled cells contribute to intravascular clotting in the crisis phase of sickle cell disease (Zwaal et al., 1989).

Both Zwaal et al. (1989) and Williamson and Schlegel (1994) have indicated that the physiological significance of surface phospholipid changes is not restricted to hemostasis. In fact, the surface exposure of PS by blood cells was said to significantly alter their recognition by the reticuloendothelial system, and was to likely represent at least part of the homeostatic mechanism for the clearance of blood cells from the circulation (Zwaal et al., 1989). Thus, PS acts as a signal for the elimination of activated platelets after bleeding has stopped. Recognition of PS exposed on sickle cells and malarially infected cells by phagocytes and macrophages explains their counter-pathophysiological effects (Zwaal et al., 1989). Furthermore, PS-dependent phagocytosis marks virally infected cells for phagocytic uptake (WO 97/17084). The surface expression of aminophospholipids could also confer "fusion competence" to a cell (Williamson and Schlegel, 1994).

Williamson and Schlegel (1994) also speculated that there is a more general raison d'être for lipid asymmetry. For example, although the different head groups have received most attention, it could well be that fatty acid asymmetry is the important factor (Williamson and Schlegel, 1994). A further hypothesis is that the asymmetric distribution of transbilayer phospholipids has no function in itself, but that it is the dynamic process of lipid movement that is important to biological systems (Williamson and Schlegel, 1994).

Many groups have reported that tumor cells are responsible for the prothrombinase activity of the tumor (Connor et al., 1989; Rao et al., 1992; Zacharski et al., 1993; Sugimura et al., 1994; Donati, 1995). This could have been reasoned to be due to PS (WO 91/07187). However, the results of Sugimura et al. (1994) argue against this: they reported that although both the prothrombinase activity and total procoagulant activity of the tumorigenic cells, HepG2 and MKN-28, fell on reaching confluency, the PS levels remained constant.

Rather than supporting a role for tumor cell PS in prothrombinase activity, Connor et al. (1989) suggested that the increased expression of PS in tumorigenic cells is relevant to their ability to be recognized and bound by macrophages. Utsugi et al. (1991) similarly proposed that the presence of PS in the outer membrane of human tumor cells explains their recognition by monocytes.

Jamasbi et al. (1994) suggested a totally different role for lipid components in tumorigenic cells, proposing that the lipids interfere with tumor antigen accessibility. Thus, tumor cell lipids would act to modify the tumor cell surface antigen(s), thus protecting the tumor cells from host immune destruction (Jamasbi et al., 1994). This hypothesis is not unlike that proposed by Qu et al. (1996), in terms of endothelial cells. These authors showed that T cells adhered to thrombin-treated human umbilical endothelial cells by virtue of binding to PS (Qu et al., 1996).

It has thus been proposed that PS-mediated T cell adhesion to endothelial cells in vivo is important to both immune surveillance, and also to the disease processes of atherosclerosis (Qu et al., 1996; Moldovan et al., 1994). Bombeli et al. (1997) and Flynn et al. (1997) also suggested that cells within atherosclerotic plaques may contribute to disease progression by exposing PS, although this was based solely on in vitro studies. Qu et al. (1996) and Moldovan et al. (1994) even hinted at an approach opposite to that of the present invention, i.e., the manipulation of phosphatidylserine interactions as an anticoagulant approach. U.S. Pat. Nos. 5,658,877 and 5,296,467 have proposed annexin (or "annexine") for use as anti-endotoxins and anti-coagulants. U.S. Pat. No. 5,632,986 (incorporated herein by reference) suggests the use of the phosphatidylserine-binding ligand, annexin V, as a conjugate with a component, such as urokinase, that lyses thrombi.

Toti et al. (1996) suggested that Scott syndrome, an inherited bleeding disorder, may reflect the deletion or mutation of a putative outward phosphatidylserine translocase or "scramblase". Although an interesting notion, Stout et al. (1997) later isolated a membrane protein from Scott erythrocytes that exhibited normal PL scramblase activity when reconstituted in vesicles with exogenous PLs. It was suggested that the defect in Scott syndrome is related to an altered interaction of $Ca^{2+}$ with PL scramblase on the endofacial surface of the cell membrane, due either to an intrinsic constraint upon the protein, preventing interaction with $Ca^{2+}$ in situ, or due to an unidentified inhibitor or cofactor in the Scott cell that is dissociated by detergent (Stout et al., 1997).

More variable results have been reported in connection with the possible role of PS in apoptosis. Williamson and Schlegel (1994) discussed the theme of PS as a marker of programmed cell death (PCD or apoptosis). It is generally accepted that programmed cell death, at least in the hematopoietic system, requires the phagocytic sequestration of the apoptopic cells before the loss of membrane integrity or "rupture". The loss of membrane asymmetry in apoptopic cells, and particularly the appearance of PS in the external leaflet, was proposed to be the trigger for their recognition by phagocytic macrophages (Williamson and Schlegel, 1994).

Martin et al. (1995) further reported PS externalization to be an early and widespread event during apoptosis of a variety of murine and human cell types, regardless of the initiating stimulus. They also indicated that, under conditions in which the morphological features of apoptosis were prevented (macromolecular synthesis inhibition, overexpression of Bcl-2 or Abl), the appearance of PS on the external leaflet of the plasma membrane was similarly prevented (Martin et al., 1995).

However, other analyses argue against the Williamson and Schlegel (1994) and Martin et al. (1995) proposals to some extent (Vermes et al., 1995). Although these authors indicate that the translocation of PS to the outer membrane surface is a marker of apoptosis, they reason that this is not unique to apoptosis, but also occurs during cell necrosis. The difference between these two forms of cell death is that during the initial stages of apoptosis the cell membrane remains intact, while at the very moment that necrosis occurs the cell membrane loses its integrity and becomes leaky. Therefore, according to this reasoning, PS expression at the cell surface does not indicate apoptosis unless a dye exclusion assay has been conducted to establish cell membrane integrity (Vermes et al., 1995).

Nonetheless, the body of literature prior to the present invention does seem to indicate that the appearance of PS on the outer surface of a cell identifies an apoptotic cell and signals that cell's ingestion (Hampton et al., 1996; WO 95/27903). Hampton et al. (1996) concluded that while an elevation of intracellular $Ca^{2+}$ was an ineffective trigger of apoptosis in the cells investigated, extracellular $Ca^{2+}$ was required for efficient PS exposure during apoptosis. In contrast, the proposal of Martin et al. (1995) that activation of an inside-outside PS translocase is an early widespread event during apoptosis would seem to require at least some intracellular $Ca^{2+}$ (Zhou et al., 1997; Zhao et al., 1998).

Blankenberg et al. (1998) very recently reported that annexin V, an endogenous human protein with a high affinity for PS, can be used to concentrate at sites of apoptotic cell death in vivo. Radiolabeled annexin V localized to sites of apoptosis in three models, including acute cardiac allograft rejection (Blankenberg et al., 1998). Staining of cardiac allografts for exogenously administered annexin V revealed myocytes at the periphery of mononuclear infiltrates, of which only a few demonstrated positive apoptotic nuclei.

Finally, the transbilayer movement of phospholipids in the plasma membrane has even been analyzed in ram sperm cells, where the existence of a transverse segregation of phospholipids has been implicated in the fertilization process (Müller et al., 1994). Phospholipid asymmetry has thus been receiving increasing attention, although a clear understanding of this phenomenon, or its relationship to health or disease, has not been realized.

Irrespective of the confusing state of the art regarding aminophospholipid biology, the present inventors discovered, in controlled in vivo studies, that aminophospholipids, such as PS and PE, were specific markers of tumor blood vessels. This is surprising in light of the earlier studies of aminophospholipid function, particularly those indicating that the cell surface expression of PS is accompanied by binding of circulating cells, such as T cells (Qu et al., 1996), macrophages (Connor et al., 1989), monocytes (Utsugi et al., 1991) or phagocytes (Zwaal et al., 1989; Williamson and Schlegel, 1994) and is a marker of apoptopic cells (Hampton et al., 1996; Martin et al., 1995; Zhou et al., 1997; Zhao et al., 1998).

Thus, prior to this invention, the possibility of using aminophospholipids as targetable markers of any disease, let alone of tumor vasculature, would be unlikely to be contemplated, due to the perceived masking of these molecules by the binding of one or more cell types, or their transient expression before apoptopic death. In fact, speculative suggestions have concerned the disruption of PS-cellular interactions, such as in preventing leukocyte binding, an initial event in atherosclerosis (Qu et al., 1996).

Other surprising aspects of this discovery are evident in a comparison to earlier work concerning the shedding of procoagulant microparticles from plasma membranes and the demarcation of cells for phagocytosis (WO 97/17084). Zwaal et al. (1989; 1992) and Dachary-Prigent et al. (1996) explained that PS translocation to the plasma membrane is followed by release of microparticles, microvesicles or microspheres from the cells. Zwaal et al. (1989) and Williamson and Schlegel (1994) indicated that PS surface expression prompts clearance by the reticuloendothelial system. In light of these fates of PS-expressing cells, and the various documented bilayer translocase activities (Julien et al., 1995; Zhou et al., 1997; Zhao et al., 1998), it is surprising that cell surface aminophospholipids such as PS and PE can form static and stable enough markers to allow antibody localization and binding.

Prior to the present invention, there was mounting evidence that surface PS appears as part of the apoptopic process, marking cells for rapid destruction (Hampton et al., 1996; Martin et al., 1995). Therefore, although reasonable for use as a diagnostic marker for certain disease states, such as graft rejection (Blankenberg et al., 1998), the apparently limited life time of surface PS would also advise against its use as a viable marker for targeting in therapeutic intervention.

Nonetheless, the present study did indeed discover aminophospholipids to be markers of tumor vascular endothelial cells suitable for targeting. After postulating that PS expression was necessary for VCAM coaguligand action, the presence of PS on tumor blood vessels, but normal vessels, was demonstrated in vivo. The in vivo observations allowed the inventors to explain the safety and effectiveness of the anti-VCAM coaguligands. This is due to the requirement for coincident expression of a targeted marker (e.g., VCAM) and PS on tumor endothelium. Even if the target molecule is present on endothelium in normal or pathological conditions, thrombosis will not result if surface PS expression is lacking.

The value of the present invention is not limited to explaining coaguligand action, nor to the surprising development of naked antibody therapies. These discoveries have allowed the inventors to show, for the first time, that PS translocation in endothelial cells can occur without significant cell damage or cell death (Example XIV). In the inventors' new model of tumor biology, the translocation of PS to the surface of tumor blood vessel endothelial cells occurs, at least in a significant part, independently of apoptopic or other cell-death mechanisms. Thus, PS surface expression in the tumor environment is not a consequence of cell death, nor does it trigger immediate cell destruction. This is of fundamental importance and represents a breakthrough in the scientific understanding of PS biology, membrane translocation, cell signaling and apoptosis pathways.

The separation of endothelial cell PS translocation from apoptosis (Example XIV) is also integral to methods of therapeutic intervention based upon PS surface expression. Should PS translocation to the outer membrane in tumor vascular endothelial cells occur only in dying cells, or should it inevitably trigger cell death, then the PS marker would not likely be sufficiently available to serve as a targetable entity for successful therapy (using either naked antibodies or therapeutic conjugates). That is not to say that PS expression on certain tumor vascular endothelial cells is not transient, and that turnover and cell death do not occur in this endothelial cell population, but the finding that significant stable PS expression can be achieved without cell death is a landmark discovery important to various fields of biology and to new therapies.

D. Naked Antibodies Against Aminophospholipids for Tumor Treatment

The present aminophospholipid tumor vasculature expression studies further support the use of coaguligands directed against known tumor vasculature markers as selective thrombotic agents for the treatment of solid tumors. The present observations also led the inventors to develop further tumor treatment methods. For example, the use of anti-aminophospholipid immunotoxins and anti-aminophospholipid coaguligands in tumor treatment is disclosed and claimed in first and second provisional applications Ser. No. 60/092,589 (filed Jul. 13, 1998) and Ser. No. 60/110,600 (filed Dec. 02, 1998) and in co-filed U.S. and PCT patent application Ser. No. 09/351,457, now U.S. Pat. No. 6,132,694; Ser. No. 09/351,598, Ser. No. 09/351,149 and WO 00/02584, each specifically incorporated herein by reference. The surprising discovery of stable PS expression on intact tumor-associated endothelial cells, which are not undergoing cell death, renders such methods both practicable and surprising (given that PS expression was thought to be associated only with cell destruction).

However, yet even more unexpected methods of tumor treatment were then discovered. In investigating the potential use of aminophospholipid targeting, in the context of later delivering a toxin or coagulant to the tumor vasculature, the inventors serendipitously discovered that naked anti-PS antibodies have a destructive effect on tumor vasculature in vivo—in the complete absence of any additional effector moiety.

One of the present inventors has been developing anti-tumor vasculature immunotoxins and coaguligands for therapeutic use for some time (for example, see U.S. Pat. Nos. 5,5855,866 and 5,877,289; and U.S. application Ser. Nos. 08/350,212, 08/487,427 and 08/482,369; Issue Fees paid; each incorporated herein by reference). In the normal course of these studies, various antibodies, including anti-Class II, anti-endoglin, anti-VCAM-1 and anti-VEGF, have been administered to tumor-bearing animals and shown to specifically localize to the intratumoral vasculature. Following such confirmation, the antibodies are linked to the toxic or coagulative effector portion to form an immunotoxin or coaguligand, which is then administered to exert an anti-tumor effect.

During such studies, no naked antibodies have been found to exert an anti-tumor effect in themselves. The ability of anti-aminophospholipid antibodies to both specifically localize to tumor vasculature and to exert a concomitant destructive effect, leading to tumor necrosis, is therefore most unexpected.

Although a precise molecular understanding of exactly how the naked antibodies function is not necessary in order to practice the present invention, the inventors have contemplated several mechanisms that may account for the observed endothelial cell killing. The favored mechanisms include cell-mediated cytotoxicity, complement-mediated lysis and/or apoptosis, although antibody-induced cell signaling and/or disturbances to the cytoskeleton may also be involved.

As the naked or unconjugated anti-aminophospholipid antibodies or antibody fragments bind to aminophospholipids at the surface of the tumor vascular endothelial cells, they will form an antibody coating on the luminal surface. This may function to attract immune effector cells, such as cytotoxic T cells and/or NK cells, which will then exert a cell-mediated cytotoxic effect on the vascular endothelial cells.

Binding of intact anti-aminophospholipid antibodies to the vascular endothelial cell surface will also mean that the Fc portions of the antibodies will protrude into the vessel lumen. As antibody Fc fragments activate the complement pathway, the observed cellular destruction may be a result of complement-directed lysis. Antibody binding thus activates the complement-dependent coagulation cascade, causing multi-component complexes to assemble and, ultimately, to generate a lytic complex that permeabilizes the target cell. "Complement-activated ADCC" may also be operating in the destruction, in which complement binds to the antibody-coated target cell, and in which cells, such as neutrophils, having receptors for complement, lyse the target cell.

Anti-aminophospholipid antibody binding may also induce apoptosis in the tumor vascular endothelial cells. Other groups have identified PS as a possible marker of apoptosis (Williamson and Schlegel, 1994). However, these previous studies were connected with the appearance of externalized PS after other stimuli had initiated the apoptopic event (Martin et al., 1995), the inverse of the present apoptosis induction proposal. There are no known reports of antibody binding to PS actually inducing apoptosis. Still, the inventors consider this to be about as likely a mechanism as the cell-mediated cytotoxicity or complement-mediated lysis, despite the fact that tangential evidence to the contrary has very recently been published by others (Nakamura et al., 1998).

Nakamura et al. (1998) analyzed antibody fractions from patients with lupus anticoagulant (LAC), a disorder associated with arterial and venous thrombosis, thrombocytopenia, and recurrent fetal loss. Plasma with LAC activity was initially reported to induce apoptosis in endothelial cells (Nakamura et al., 1994). The apoptotic activities of LAC antisera were then reported to be localized in an annexin V-binding antibody fraction in 10/10 patients studied (Nakamura et al., 1998). As annexin binds to PS, the apparent ability of anti-annexin antibodies to induce apoptosis would be the opposite of one of the destructive mechanisms proposed by the present inventors, i.e., the ability of anti-PS antibodies to induce apoptosis.

The ability of LAC antibody fractions to induce apoptosis was further reported to be inhibited by preincubation with annexin V (Nakamura et al., 1998). In contrast, removal of anti-phospholipid antibodies from the patients' IgG fractions with phospholipid liposomes did not abolish the apoptosis-inducing activities or annexin V binding (Nakamura et al., 1998). These results reasonably implied that patients with LAC often have antibodies that do not bind phospholipids and yet are responsible for the induction of apoptosis in endothelial cells (Nakamura et al., 1998).

Without needing to equate the Nakamura et al. (1998) LAC data with the present observations from in vivo studies of tumors and tumor vasculature, due to the evidently disparate nature of these clinical conditions, the present inventors nonetheless have certain unifying theories. Nakamura et al. (1998) attempted to remove anti-phospholipid antibodies from patients' antisera using phospholipid liposomes, and observed that this did not abolish the apoptosis-inducing activity. These results led Nakamura et al. (1998) to conclude that the anti-phospholipids antibodies cannot be responsible for apoptopic activity. However, the present inventors now have the insight to suggest that the incubation with phospholipid liposomes may not have removed the anti-phospholipids antibodies from the antisera, as phospholipids are antigenically neutral in bilayer and liposomal form, and largely only bind antibodies in hexagonal form (Rauch et al., 1986; Rauch and Janoff, 1990; Berard et al., 1993; each incorporated herein by reference) or in association with membrane proteins. Thus, anti-phospholipids antibodies may remain in the LAC antisera and may cause, or contribute to, the observed apoptopic activity.

It is also conceivable that anti-aminophospholipid binding to the surface of tumor vascular endothelial cells may cause disturbances in the cytoskeletalal organization of the cell. As the cytoskeleton plays a role in the organization of surface membranes, and as anti-aminophospholipid binding may disturb (or further disturb) the membrane, antibody binding may transmit changes to cytoskeletal proteins that interact with the bilayer. It is already known that the spatial organization of cytoskeletal proteins controls membrane stability and cell shape, and it is possible that perturbation of some cytoskeletal equilibrium may have far-reaching consequences on cell integrity.

A further mechanism of operation of the invention may be that anti-aminophospholipid antibody binding to the endothelial cell surface may initiate signal transduction by, as yet, undefined pathways. Anti-aminophospholipid antibody binding may also disturb known signal transduction pathways, e.g., by altering the conformation and/or interactions of membrane receptors, signal transduction proteins, membrane channels, and the like. Signals for cell destruction (apoptosis) may be initiated or mimicked, and/or preservation/homeostatic signals may be inhibited.

Although of scientific interest, determining the exact nature of the vascular destruction achieved by the naked anti-aminophospholipid antibodies is not necessary to the practice of the present invention. Given that the administration of anti-aminophospholipid antibodies is herein shown to advantageously result in specific anti-tumor effects in vivo, the invention can be utilized irrespective of the molecular mechanism that underlies this phenomenon.

The naked antibody use of the present invention thus represent a significant advance in tumor therapy. Although coaguligands are advantageous for tumor therapy, the targeting antibody or ligand still needs to be conjugated to, or functionally associated with, the effector coagulant, such as Tissue Factor. Therefore, the practice of the coaguligand targeting and tumor destruction methodology is somewhat laborious in that it requires the preparation of suitable conjugates, or co-ordinated molecular complexes (including bispecific antibodies). For example, one must prepare a targeting antibody or ligand that binds to the desired target antigen; choose an appropriate coagulant; link the coagulant to the targeting antibody or ligand, or otherwise form a functional association of the two components, to form the "coaguligand"; separate the coaguligand from the unconjugated, or uncomplexed, targeting agent and coagulant; and then conduct the treatment protocols.

Although coaguligand-based methods can be readily and successfully practiced, one can see the advantages that result from the present development of methodology that includes less preparative steps and can therefore be performed in a more cost-effective manner. Furthermore, the present invention provides a one-component system that will be more quickly progressed through the regulatory approval process, allowing improved treatment methods to be translated to the clinic, where they are urgently needed.

E. Anti-Aminophospholipid Antibodies

E1. Polyclonal Anti-Aminophospholipid Antibodies

Means for preparing and characterizing antibodies are well known in the art (see, e.g., Antibodies: A Laboratory Manual, Cold Spring Harbor Laboratory, 1988; incorporated herein by reference). To prepare polyclonal antisera an animal is immunized with an immunogenic aminophospholipid composition, and antisera collected from that immunized animal. A wide range of animal species can be used for the production of antisera. Typically the animal used for production of anti-antisera is a rabbit, mouse, rat, hamster, guinea pig or goat. Because of the relatively large blood volume of rabbits, a rabbit is a preferred choice for production of polyclonal antibodies.

The amount of immunogen composition used in the production of polyclonal antibodies varies upon the nature of the immunogen as well as the animal used for immunization. A variety of routes can be used to administer the present aminophospholipid immunogen; subcutaneous, intramuscular, intradermal, intravenous, intraperitoneal and intrasplenic. The production of polyclonal antibodies may be monitored by sampling blood of the immunized animal at various points following immunization. A second, booster injection, may also be given. The process of boosting and titering is repeated until a suitable titer is achieved. When a desired titer level is obtained, the immunized animal can be bled and the serum isolated and stored. The animal can also be used to generate monoclonal antibodies.

As is well known in the art, the immunogenicity of a particular composition can be enhanced by the use of non-specific stimulators of the immune response, known as adjuvants. Exemplary adjuvants include complete Freund's adjuvant, a non-specific stimulator of the immune response containing killed *Mycobacterium tuberculosis;* incomplete Freund's adjuvant; and aluminum hydroxide adjuvant.

It may also be desired to boost the host immune system, as may be achieved by associating aminophospholipids with, or coupling aminophospholipids to, a carrier. Exemplary carriers are keyhole limpet hemocyanin (KLH) and bovine serum albumin (BSA). Other albumins such as ovalbumin, mouse serum albumin or rabbit serum albumin can also be used as carriers.

As is also known in the art, a given composition may vary in its immunogenicity. However, the generation of antibodies against aminophospholipids is not particularly difficult. For example, highly specific anti-phosphatidylserine antibodies were raised in rabbits immunized by intramuscular injections of phosphatidylserine-containing polyacrylamide gels and with phosphatidylserine-cytochrome c vesicles (Maneta-Peyret et al., 1988; 1989; each incorporated herein by reference). The use of acrylamide implants enhanced the production of antibodies (Maneta-Peyret et al., 1988; 1989). The anti-phosphatidylserine antibodies raised in this manner are able to detect phosphatidylserine in situ on human platelets (Maneta-Peyret et al., 1988). The groups of Inoue, Rote and Rauch have also developed anti-PS and anti-PE antibodies (see below).

E2. Monoclonal Anti-Aminophospholipid Antibodies

Various methods for generating monoclonal antibodies (MAbs) are also now very well known in the art. The most standard monoclonal antibody generation techniques generally begin along the same lines as those for preparing polyclonal antibodies (Antibodies: A Laboratory Manual, Cold Spring Harbor Laboratory, 1988; incorporated herein by reference). A polyclonal antibody response is initiated by immunizing an animal with an immunogenic aminophospholipid composition and, when a desired titer level is obtained, the immunized animal can be used to generate MAbs.

MAbs may be readily prepared through use of well-known techniques, such as those exemplified in U.S. Pat. No. 4,196,265, incorporated herein by reference. Typically, this technique involves immunizing a suitable animal with the selected aminophospholipid immunogen composition. The immunizing composition is administered in a manner effective to stimulate antibody producing cells. Rodents such as mice and rats are preferred animals, however, the use of rabbit, sheep and frog cells is also possible. The use of rats may provide certain advantages (Goding, 1986, pp. 60–61; incorporated herein by reference), but mice are preferred, with the BALB/c mouse being most preferred as this is most routinely used and generally gives a higher percentage of stable fusions.

Following immunization, somatic cells with the potential for producing aminophospholipid antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The anti-aminophospholipid antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984; each incorporated herein by reference). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XXO Bul; for rats, one may use R210.RCY3, Y3-Ag 1.2.3, IR983F, 4B210 or one of the above listed mouse cell lines; and U-266, GM1500-GRG2, LICR-LON-HMy2 and UC729-6, are all useful in connection with human cell fusions.

Methods for generating hybrids of antibody-producing spleen or lymph node cells and myeloma cells usually comprise mixing somatic cells with myeloma cells in a 4:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976; each incorporated herein by reference), and those using polyethylene glycol (PEG), such as 37% (v/v) PEG, by Gefter et al. (1977; incorporated herein by reference). The use of electrically induced fusion methods is also appropriate (Goding pp. 71–74, 1986; incorporated herein by reference).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired anti-aminophospholipid reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual anti-aminophospholipid antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations.

MAbs produced by either means will generally be further purified, e.g., using filtration, centrifugation and various chromatographic methods, such as HPLC or affinity chromatography, all of which purification techniques are well known to those of skill in the art. These purification techniques each involve fractionation to separate the desired antibody from other components of a mixture. Analytical methods particularly suited to the preparation of antibodies include, for example, protein A-Sepharose and/or protein G-Sepharose chromatography.

Umeda et al. (1989; incorporated herein by reference) reported the effective production of monoclonal antibodies recognizing stereo-specific epitopes of phosphatidylserine. The Umeda system is based on the direct immunization of phosphatidylserine into mouse spleen using a Salmonella-coated aminophospholipid sample (Umeda et al., 1989; incorporated herein by reference). The Umeda protocol gives a high frequency of anti-PS MAbs, which exhibit three distinct reactivity profiles ranging from highly specific to broadly cross-reactive. Umeda is therefore also incorporated herein by reference for purposes of further describing screening assays to identify MAbs that bind specifically to PS, e.g., and do not bind to phosphatidylcholine.

Any of the 61 hybridomas generated by Umeda could potentially be employed in the present invention. Examples are PSC8, PSF11, PSG3, PSD11, PSF10, PS1B, PS3D12, PS2C11; PS3A, PSF6, PSF7, PSB4, PS3H1; PS4A7 and PS1G3. More preferred are PS3A, PSF6, PSF7, PSB4 and PS3H1 as they bind only to phosphatidylserine and phosphatidylethanolamine. Preferred anti-PS antibodies are PS4A7 (IgM) and PS1G3 (IgG$_3$), as they are highly specific for PS and exhibit no cross-reaction with other phospholipids. PS4A7 recognizes the stereo-specific configuration of the serine residue in PS (FIG. 1 Umeda et al., 1989; incorporated herein by reference).

Igarashi et al. (1991; incorporated herein by reference) also reported the effective induction of anti-PS antibodies of the IgG isotype by intrasplenic immunization. Only a slight increase of the titer was observed when the antigen was again injected intravenously. A high frequency of anti-PS MAbs of the IgG isotype was also observed even when MAbs were produced 10 days after the intrasplenic injection of the antigen. These antibodies were also employed by Schuurmans Stekhoven et al. (1994).

The other significant anti-PS antibody production has been by Rote and colleagues. Rote et al. (1993; incorporated herein by reference) particularly employed PS micelles in combination with Freund's complete adjuvant to generate specific anti-PS antibodies. Rote et al. (1993) also generated monoclonal antibodies that differentiate between cardiolipin (CL) and PS. Rote et al. (1993) is therefore also incorporated herein by reference for purposes of further describing screening assays to identify MAbs that bind specifically to PS by testing against resting and thrombin-activated platelets using flow cytometry.

The 3SB9b antibody produced by Rote et al. (1993) reacted with only with PS, and is a preferred antibody for use in the present invention. BA3B5C4 may also be used as it reacts with both PS and CL. These antibodies are also described in Lin et al. (1995), Obringer et al. (1995) and Katsuragawa et al. (1997).

E3. Anti-Aminophospholipid Antibodies from Phagemid Libraries

Recombinant technology now allows the preparation of antibodies having the desired specificity from recombinant genes encoding a range of antibodies (Van Dijk et al., 1989; incorporated herein by reference). Certain recombinant techniques involve the isolation of the antibody genes by immunological screening of combinatorial immunoglobulin phage expression libraries prepared from RNA isolated from the spleen of an immunized animal (Morrison et al., 1986; Winter and Milstein, 1991; each incorporated herein by reference).

For such methods, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination, which further increases the percentage of appropriate antibodies generated.

One method for the generation of a large repertoire of diverse antibody molecules in bacteria utilizes the bacteriophage lambda as the vector (Huse et al., 1989; incorporated herein by reference). Production of antibodies using the lambda vector involves the cloning of heavy and light chain populations of DNA sequences into separate starting vectors. The vectors are subsequently combined randomly to form a single vector that directs the co-expression of heavy and light chains to form antibody fragments. The heavy and light chain DNA sequences are obtained by amplification, preferably by PCR™ or a related amplification technique, of mRNA isolated from spleen cells (or hybridomas thereof) from an animal that has been immunized with a selected antigen. The heavy and light chain sequences are typically amplified using primers that incorporate restriction sites into the ends of the amplified DNA segment to facilitate cloning of the heavy and light chain segments into the starting vectors.

Another method for the generation and screening of large libraries of wholly or partially synthetic antibody combining sites, or paratopes, utilizes display vectors derived from filamentous phage such as M13, fl or fd. These filamentous phage display vectors, referred to as "phagemids", yield large libraries of monoclonal antibodies having diverse and novel immunospecificities. The technology uses a filamentous phage coat protein membrane anchor domain as a means for linking gene-product and gene during the assembly stage of filamentous phage replication, and has been used for the cloning and expression of antibodies from combinatorial libraries (Kang et al., 1991; Barbas et al., 1991; each incorporated herein by reference).

This general technique for filamentous phage display is described in U.S. Pat. No. 5,658,727, incorporated herein by reference. In a most general sense, the method provides a system for the simultaneous cloning and screening of pre-selected ligand-binding specificities from antibody gene repertoires using a single vector system. Screening of isolated members of the library for a pre-selected ligand-binding capacity allows the correlation of the binding capacity of an expressed antibody molecule with a convenient means to isolate the gene that encodes the member from the library.

Linkage of expression and screening is accomplished by the combination of targeting of a fusion polypeptide into the periplasm of a bacterial cell to allow assembly of a functional antibody, and the targeting of a fusion polypeptide onto the coat of a filamentous phage particle during phage assembly to allow for convenient screening of the library member of interest. Periplasmic targeting is provided by the presence of a secretion signal domain in a fusion polypeptide. Targeting to a phage particle is provided by the presence of a filamentous phage coat protein membrane anchor domain (i.e., a cpIII- or cpVIII-derived membrane anchor domain) in a fusion polypeptide.

The diversity of a filamentous phage-based combinatorial antibody library can be increased by shuffling of the heavy and light chain genes, by altering one or more of the complementarity determining regions of the cloned heavy chain genes of the library, or by introducing random mutations into the library by error-prone polymerase chain reactions. Additional methods for screening phagemid libraries are described in U.S. Pat. Nos. 5,580,717; 5,427,908; 5,403,484; and 5,223,409, each incorporated herein by reference.

Another method for the screening of large combinatorial antibody libraries has been developed, utilizing expression of populations of diverse heavy and light chain sequences on the surface of a filamentous bacteriophage, such as M13, fl or fd (U.S. Pat. No. 5,698,426; incorporated herein by reference). Two populations of diverse heavy (Hc) and light (Lc) chain sequences are synthesized by polymerase chain reaction (PCR™). These populations are cloned into separate M13-based vector containing elements necessary for expression. The heavy chain vector contains a gene VIII (gVIII) coat protein sequence so that translation of the heavy chain sequences produces gVIII-Hc fusion proteins. The populations of two vectors are randomly combined such that only the vector portions containing the Hc and Lc sequences are joined into a single circular vector.

The combined vector directs the co-expression of both Hc and Lc sequences for assembly of the two polypeptides and surface expression on M13 (U.S. Pat. No. 5,698,426; incorporated herein by reference). The combining step randomly brings together different Hc and Lc encoding sequences within two diverse populations into a single vector. The vector sequences donated from each independent vector are necessary for production of viable phage. Also, since the pseudo gVIII sequences are contained in only one of the two starting vectors, co-expression of functional antibody fragments as Lc associated gVIII-Hc fusion proteins cannot be accomplished on the phage surface until the vector sequences are linked in the single vector.

Surface expression of the antibody library is performed in an amber suppressor strain. An amber stop codon between the Hc sequence and the gVIII sequence unlinks the two components in a non-suppressor strain. Isolating the phage produced from the non-suppressor strain and infecting a suppressor strain will link the Hc sequences to the gVIII sequence during expression. Culturing the suppressor strain after infection allows the coexpression on the surface of M13 of all antibody species within the library as gVIII fusion proteins (gVIII-Fab fusion proteins). Alternatively, the DNA can be isolated from the non-suppressor strain and then introduced into a suppressor strain to accomplish the same effect.

The surface expression library is screened for specific Fab fragments that bind preselected molecules by standard affinity isolation procedures. Such methods include, for example, panning (Parmley and Smith, 1988; incorporated herein by reference), affinity chromatography and solid phase blotting procedures. Panning is preferred, because high titers of phage can be screened easily, quickly and in small volumes. Furthermore, this procedure can select minor Fab fragments species within the population, which otherwise would have been undetectable, and amplified to substantially homogenous populations. The selected Fab fragments can be characterized by sequencing the nucleic acids encoding the polypeptides after amplification of the phage population.

Another method for producing diverse libraries of antibodies and screening for desirable binding specificities is described in U.S. Pat. Nos. 5,667,988 and 5,759,817, each incorporated herein by reference. The method involves the preparation of libraries of heterodimeric immunoglobulin molecules in the form of phagemid libraries using degenerate oligonucleotides and primer extension reactions to incorporate the degeneracies into the CDR regions of the immunoglobulin variable heavy and light chain variable domains, and display of the mutagenized polypeptides on the surface of the phagemid. Thereafter, the display protein is screened for the ability to bind to a preselected antigen.

The method for producing a heterodimeric immunoglobulin molecule generally involves (1) introducing a heavy or light chain V region-coding gene of interest into the phagemid display vector; (2) introducing a randomized binding site into the phagemid display protein vector by primer extension with an oligonucleotide containing regions of homology to a CDR of the antibody V region gene and containing regions of degeneracy for producing randomized coding sequences to form a large population of display vectors each capable of expressing different putative binding sites displayed on a phagemid surface display protein; (3) expressing the display protein and binding site on the surface of a filamentous phage particle; and (4) isolating (screening) the surface-expressed phage particle using affinity techniques such as panning of phage particles against a preselected antigen, thereby isolating one or more species of phagemid containing a display protein containing a binding site that binds a preselected antigen.

A further variation of this method for producing diverse libraries of antibodies and screening for desirable binding specificities is described in U.S. Pat. No. 5,702,892, incorporated herein by reference. In this method, only heavy chain sequences are employed, the heavy chain sequences are randomized at all nucleotide positions which encode either the CDRI or CDRIII hypervariable region, and the genetic variability in the CDRs is generated independent of any biological process.

In the method, two libraries are engineered to genetically shuffle oligonucleotide motifs within the framework of the heavy chain gene structure. Through random mutation of either CDRI or CDRIII, the hypervariable regions of the heavy chain gene were reconstructed to result in a collection of highly diverse sequences. The heavy chain proteins encoded by the collection of mutated gene sequences possessed the potential to have all of the binding characteristics of an immunoglobulin while requiring only one of the two immunoglobulin chains.

Specifically, the method is practiced in the absence of the immunoglobulin light chain protein. A library of phage displaying modified heavy chain proteins is incubated with an immobilized ligand to select clones encoding recombinant proteins that specifically bind the immobilized ligand. The bound phage are then dissociated from the immobilized ligand and amplified by growth in bacterial host cells. Individual viral plaques, each expressing a different recombinant protein, are expanded, and individual clones can then be assayed for binding activity.

E4. Anti-Aminophospholipid Antibodies from Human Patients

Antibodies against aminophospholipids, particularly phosphatidylserine and phosphatidylethanolamine, occur in the human population, where they are correlated with certain disease states. Anti-aminophospholipid antibodies are part of the heterogeneous anti-phospholipid antibodies (aPL), observed to have families of different specificities and classes. Primary anti-phospholipid syndrome (APS) has even been separated from other forms of autoimmune disease associated with anti-phospholipid antibody production.

Anti-PS antibodies are particularly associated with recurrent pregnancy loss (Rote et al., 1995; Rote, 1996; Vogt et al., 1996; Vogt et al., 1997; incorporated herein by reference) and with the autoimmune disease, systemic lupus erythematosus (SLE or "lupus") (Branch et al., 1987; incorporated herein by reference). Anti-PE antibodies have also been reported in human patients, particularly those with autoimmune diseases (Staub et al., 1989). Branch et al. (1987) reported that 80% of patients with lupus anticoagulant (LA or LAC) had autoantibodies that recognized PE; with Drouvalakis and Buchanan (1998) increasing this number to 95% PE-positives from autoimmune LAC sera.

Anti-phospholipid antibodies are not to be confused with anti-endothelial cell antibodies (AECA), although they can be found in the same patient. The existence of AECA has been documented in a variety of clinical settings associated with vasculitis, such as systemic sclerosis (SS). To study AECA, antibodies are obtained from patients that do not have anti-phospholipid antibodies (aPL-negative sera).

The pathogenic role of AECA remains unclear, although Bordron et al. (1998) very recently suggested that AECA may initiate apoptosis in endothelial cells, which would be followed by PS transfer to the outer face of the membrane. They proposed that this would account for the subsequent generation of the anti-phospholipid antibodies that are some-times seen in conjunction with AECA in patients with skin lesions or connective tissue disease (Bordron et al., 1998). However, although AECA binding to an apoptosis-inducing antigen was postulated, these studies did not lead to the further characterization of AECA, still said to represent an extremely heterogeneous family of antibodies reacting with different (non-lipid) structures on endothelial cells (Bordron et al., 1998).

Anti-phosphatidylserine antibodies are closely associated with pregnancy loss, pregnancy-induced hypertension and intrauterine growth retardation. A phosphatidylserine-dependent antigen has been shown to be expressed on the surface of a choriocarcinoma model (BeWo) of differentiating cytotrophoblastic cells, indicating that it should be accessible in vivo to circulating anti-phosphatidylserine antibodies (Rote et al., 1995). Indeed, Vogt et al. (1996) showed that the monoclonal antibody 3SB9b, which reacts with phosphatidylserine but not cardiolipin, induced a significant reduction in both fetal and placental weights in a mouse model for the anti-phospholipid antibody syndrome.

These authors developed a model for explaining miscarriages associated with anti-phospholipid antibodies: anti-phosphatidylserine antibody reveals sites for prothrombin binding on the surface of the trophoblast, most likely by removing Annexin V (Vogt et al., 1997). Trophoblast differentiation is associated with externalization of phosphatidylserine from the inner to the outer surface of the plasma membrane. Normally, externalization of phosphatidylserine is concurrent with binding of Annexin V, which prevents the phosphatidylserine-rich surface from acting as a site for activation of coagulation. Thus, when anti-phospholipid antibodies are present, they prevent Annexin V binding and lead to a procoagulant state (Vogt et al., 1997).

Anti-PE antibodies are frequently associated with lupus anticoagulants (LAC sera). The role of PE and anti-PE in LAC is extremely complex, see, e.g., Smirnov et al. (1995; incorporated herein by reference), where various hypotheses are set forth. Smirnov et al. (1995) report that, in the presence of activated protein C and PE, LAC plasma clots faster than normal plasma. Rauch et al. (1986) characterize LAC anti-phospholipid antibodies as prolonging the clotting time in in vitro coagulation assays.

Vlachoyiannopoulos et al. (1993; incorporated herein by reference) tested SLE and APS sera by ELISA for antibodies to phosphatidylethanolamine and cardiolipin, as compared to healthy blood donors. Both SLE and APS patients were reported to present a higher titer of IgM anti-PE antibodies than normal subjects, while the IgG and IgA anti-PE reactivity reportedly did not differ. It was suggested that IgA and IgG anti-PE antibodies may occur in low titers as natural autoantibodies in normal subjects (Vlachoyiannopoulos et al., 1993; incorporated herein by reference).

Rauch et al. (1986; incorporated herein by reference) produced hybridomas by fusing lymphocytes from 13 systemic lupus erythematosus patients with a lymphoblastoid line. They demonstrated that the autoantibodies that prolonged clotting time bound to hexagonal phase phospholipids, including natural and synthetic forms of phosphatidylethanolamine (Rauch et al., 1986; incorporated herein by reference). In contrast, lamellar phospholipids, such as phosphatidylcholine and synthetic lamellar forms of phosphatidylethanolamine, had no effect on the anticoagulant activity (Rauch et al., 1986).

Rauch and Janoff (1990; incorporated herein by reference) went on to show that immunization of mice with phosphatidylethanolamine in the hexagonal II phase, but not in the bilayer phase, resulted in the induction of anti-phospholipid antibodies. These antibodies were strongly reactive with phosphatidylethanolamine and had functional lupus anticoagulant activity characteristic of autoantibodies from patients with autoimmune disease (Rauch and Janoff, 1990).

The hexagonal II phase form of aminophospholipids should thus be advantageously used to generate antibodies for use in the present invention. Indeed, Trudell reported that antibodies raised against TFA-(trifluoroacetyl-) protein adducts bind to TFA-phosphatidylethanolamine in hexagonal phase phospholipid micelles, but not in lamellar liposomes (Trudell et al., 1991a; incorporated herein by reference). The authors suggested that TFA-phosphatidylethanolamine adducts that reside in non-lamellar domains on the hepatocyte surface could be recognition sites for anti-TFA-adduct antibodies and potentially participate in immune-mediated halothane hepatotoxicity (Trudell et al., 1991a). It was later shown that these same antibodies cross-react with TFA-dioleoylphosphatidylethanolamine when this adduct is incorporated into the surface of hepatocytes (Trudell et al., 1991b; incorporated herein by reference), thus supporting this hypothesis.

Berard further explained the hexagonal II phase form of aminophospholipids, such as PE (Berard et al., 1993; incorporated herein by reference). In bilayers, phospholipids generally adopt a gel structure, crystalline lattice or lamellar phase (Berard et al., 1993). However, depending on the cholesterol content, protein and ionic environments, phospholipids can easily change phases, adopting a hexagonal II phase (Berard et al., 1993; incorporated herein by reference). It is this hexagonal II phase of aminophospholipids that is believed to be immunogenic, as initial proposed for autoantibody generation in disease situations (Berard et al., 1993; incorporated herein by reference).

Qamar et al. (1990; incorporated herein by reference) have developed a variation on the hexagonal aminophospholipid recognition theme. Using phosphatidylethanolamine as a model, these authors reported that anti-PE antibodies from aPL-positive SLE sera do not bind to PE, but in fact are directed to lysophosphatidylethanolamine (lPE), a natural PE degradation product and a likely contaminant of most PE preparations (Qamar et al., 1990; incorporated herein by reference).

Other recent data indicate that most anti-phospholipid antibodies recognize phospholipid in the context of nearby proteins (Rote, 1996; Chamley et al., 1991). In plasma membranes, the majority of the phospholipid appears to be naturally in non-antigenic bilaminar form (Rote, 1996). Accessory molecules may help facilitate the transition to hexagonal antigenic forms and stabilize their expression (Galli et al., 1993). For example, naturally occurring anti-phospholipid antibodies were first reported to recognize complexes of cardiolipin or phosphatidylserine with $\beta_2$-glycoprotein I ($\beta_2$-GPI or apolipoprotein H, apoH) (Galli et al., 1990; 1993). $\beta_2$-GPI is believed to stabilize phospholipids in antigenic conformations that do not exist in pure phospholipids (McNeil et al., 1990; U.S. Pat. No. 5,344,758; Chamley et al., 1991; Matsuura et al., 1994). Prothrombin has also been implicated in the phospholipid stabilization process (Bevers et al., 1991).

Phospholipid-binding plasma proteins are also generally necessary for antibody recognition of the electrically neutral or zwitterionic phospholipid, phosphatidylethanolamine. Sugi and McIntyre (1995; incorporated herein by reference) identified two prominent PE-binding plasma proteins as high molecular weight kininogen (HMWK or HK) and low molecular weight kininogen (LMWK or LK). Anti-PE antibodies from patients with SLE and/or recurrent spontaneous abortions were shown not to recognize PE, HMWK or LMWK when they were presented independently as sole antigens on ELISA plates (Sugi and McIntyre, 1995). Other anti-PE-positive sera that did not react with PE-HMWK or PE-LMWK were suggested to recognize factor XI or prekallikrein, which normally bind to HMWK (Sugi and McIntyre, 1995; incorporated herein by reference).

The validity of these results was confirmed by showing that intact HMWK binds to various phospholipids, such as cardiolipin, phosphatidylserine, phosphatidylcholine and phosphatidylethanolamine; but that anti-PE antibodies recognize only a kininogen-PE complex, and do not recognize kininogens presented with other phospholipid substrates (Sugi and McIntyre, 1996a; incorporated herein by reference). This indicates that PE induces unique antigenic conformational changes in the kininogens that are not induced when the kininogens bind to other phospholipids (Sugi and McIntyre, 1996a).

It has further been suggested that kininogens can bind to platelets by virtue of exposed PE in the platelet membrane (Sugi and McIntyre, 1996b; incorporated herein by reference). Exogenously added kininogen-dependent anti-PE was shown to increase thrombin-induced platelet aggregation in vitro, but not to alter ADP-induced aggregation (Sugi and McIntyre, 1996b; incorporated herein by reference). In contrast, kininogen independent anti-PE, which recognized PE per se, was reported not augment thrombin-induced platelet aggregation. It was thus proposed that kininogen dependent anti-PE may disrupt the normal anti-thrombotic effects of kininogen (Sugi and McIntyre, 1996b; incorporated herein by reference).

Anti-aminophospholipid antibodies from human patients are therefore a mixture of antibodies that generally recognize aminophospholipids stabilized by protein interactions (Rote, 1996). The antibodies may bind to stabilized phospholipid epitopes, or may bind to an epitope formed from the interaction of the phospholipid and amino acids on the stabilizing protein (Rote, 1996). Either way, such antibodies clearly recognize aminophospholipids in natural membranes in the human body, probably associated with plasma proteins (McNeil et al., 1990; Bevers et al., 1991). These antibodies would thus be appropriate as starting materials for generating an antibody for use in the present invention.

To prepare an anti-aminophospholipid antibody from a human patient, one would simply obtain human lymphocytes from an individual having anti-aminophospholipid antibodies, for example from human peripheral blood, spleen, lymph nodes, tonsils or the like, utilizing techniques that are well known to those of skill in the art. The use of peripheral blood lymphocytes will often be preferred.

Human monoclonal antibodies may be obtained from the human lymphocytes producing the desired anti-aminophospholipid antibodies by immortalizing the human lymphocytes, generally in the same manner as described above for generating any monoclonal antibody. The reactivities of the antibodies in the culture supernatants are generally first checked, employing one or more selected aminophospholipid antigen(s), and the lymphocytes that exhibit high reactivity are grown. The resulting lymphocytes are then fused with a parent line of human or mouse origin, and further selection gives the optimal clones.

The recovery of monoclonal antibodies from the immortalized cells may be achieved by any method generally employed in the production of monoclonal antibodies. For instance, the desired monoclonal antibody may be obtained by cloning the immortalized lymphocyte by the limiting dilution method or the like, selecting the cell producing the desired antibody, growing the selected cells in a medium or the abdominal cavity of an animal, and recovering the desired monoclonal antibody from the culture supernatant or ascites.

Such techniques have been used, for example, to isolate human monoclonal antibodies to Pseudomonas aeruginosa epitopes (U.S. Pat. Nos. 5,196,337 and 5,252,480, each incorporated herein by reference); polyribosylribitol phosphate capsular polysaccharides (U.S. Pat. No. 4,954,449, incorporated herein by reference); the Rh(D) antigen (U.S. Pat. No. 5,665,356, incorporated herein by reference); and viruses, such as human immunodeficiency virus, respiratory syncytial virus, herpes simplex virus, varicella zoster virus and cytomegalovirus (U.S. Pat. Nos. 5,652,138; 5,762,905; and 4,950,595, each incorporated herein by reference).

The applicability of the foregoing techniques to the generation of human anti-aminophospholipid antibodies is clear. Rauch et al. (1986; incorporated herein by reference) generally used such methods to produce hybridomas by fusing lymphocytes from SLE patients with a lymphoblastoid line. This produced human antibodies that bound to hexagonal phase phospholipids, including natural and synthetic forms of phosphatidylethanolamine (Rauch et al., 1986; incorporated herein by reference).

Additionally, the methods described in U.S. Pat. No. 5,648,077 (incorporated herein by reference) can be used to form a trioma or a quadroma that produces a human antibody against a selected aminophospholipid. In a general sense, a hybridoma cell line comprising a parent rodent immortalizing cell, such as a murine myeloma cell, e.g. SP-2, is fused to a human partner cell, resulting in an immortalizing xenogeneic hybridoma cell. This xenogeneic hybridoma cell is fused to a cell capable of producing an anti-arninophospholipid human antibody, resulting in a trioma cell line capable of generating human antibody effective against such antigen in a human. Alternately, when greater stability is desired, a trioma cell line which preferably no longer has the capability of producing its own antibody is made, and this trioma is then fused with a further cell capable of producing an antibody useful against the aminophospholipid antigen to obtain a still more stable hybridoma (quadroma) that produces antibody against the antigen.

E5. Anti-Aminophospholipid Antibodies from Human Lymphocytes

In vitro immunization, or antigen stimulation, may also be used to generate a human anti-aminophospholipid antibody. Such techniques can be used to stimulate peripheral blood lymphocytes from both anti-aminophospholipid antibody-producing human patients, and also from normal, healthy subjects. Indeed, Vlachoyiannopoulos et al. (1993; incorporated herein by reference) reported that low titer anti-aminophospholipid antibodies occur in normal subjects. Even if this were not the case, anti-aminophospholipid antibodies can be prepared from healthy human subjects, simply by stimulating antibody-producing cells with aminophospholipids in vitro.

Such "in vitro immunization" involves antigen-specific activation of non-immunized B lymphocytes, generally within a mixed population of lymphocytes (mixed lymphocyte cultures, MLC). In vitro immunizations may also be supported by B cell growth and differentiation factors and lymphokines. The antibodies produced by these methods are often IgM antibodies (Borrebaeck et al., 1986; incorporated herein by reference).

Another method has been described (U.S. Pat. No. 5,681,729, incorporated herein by reference) wherein human lymphocytes that mainly produce IgG (or IgA) antibodies can be obtained. The method involves, in a general sense, transplanting human lymphocytes to an immunodeficient animal so that the human lymphocytes "take" in the animal body; immunizing the animal with a desired antigen, so as to generate human lymphocytes producing an antibody specific to the antigen; and recovering the human lymphocytes producing the antibody from the animal. The human lymphocytes thus produced can be used to produce a monoclonal antibody by immortalizing the human lymphocytes producing the antibody, cloning the obtained immortalized human-originated lymphocytes producing the antibody, and recovering a monoclonal antibody specific to the desired antigen from the cloned immortalized human-originated lymphocytes.

The immunodeficient animals that may be employed in this technique are those that do not exhibit rejection when human lymphocytes are transplanted to the animals. Such animals may be artificially prepared by physical, chemical or biological treatments. Any immunodeficient animal may be employed. The human lymphocytes may be obtained from human peripheral blood, spleen, lymph nodes, tonsils or the like.

The "taking" of the transplanted human lymphocytes in the animals can be attained by merely administering the human lymphocytes to the animals. The administration route is not restricted and may be, for example, subcutaneous, intravenous or intraperitoneal. The dose of the human lymphocytes is not restricted, and can usually be $10^6$ to $10^8$ lymphocytes per animal. The immunodeficient animal is then immunized with the desired aminophospholipid antigen.

After the immunization, human lymphocytes are recovered from the blood, spleen, lymph nodes or other lymphatic tissues by any conventional method. For example, mononuclear cells can be separated by the Ficoll-Hypaque (specific gravity: 1.077) centrifugation method, and the monocytes removed by the plastic dish adsorption method. The contaminating cells originating from the immunodeficient animal may be removed by using an antiserum specific to the animal cells. The antiserum may be obtained by, for example, immunizing a second, distinct animal with the spleen cells of the immunodeficient animal, and recovering serum from the distinct immunized animal. The treatment with the antiserum may be carried out at any stage. The human lymphocytes may also be recovered by an immunological method employing a human immunoglobulin expressed on the cell surface as a marker.

By these methods, human lymphocytes mainly producing IgG and IgA antibodies specific to one or more selected aminophospholipid(s) can be obtained. Monoclonal antibodies are then obtained from the human lymphocytes by immortalization, selection, cell growth and antibody production.

E6. Transgenic Mice Containing Human Antibody Libraries

Recombinant technology is now available for the preparation of antibodies. In addition to the combinatorial immunoglobulin phage expression libraries disclosed above, another molecular cloning approach is to prepare antibodies from transgenic mice containing human antibody libraries. Such techniques are described in U.S. Pat. No. 5,545,807, incorporated herein by reference.

In a most general sense, these methods involve the production of a transgenic animal that has inserted into its germline genetic material that encodes for at least part of an immunoglobulin of human origin or that can rearrange to encode a repertoire of immunoglobulins. The inserted genetic material may be produced from a human source, or may be produced synthetically. The material may code for at least part of a known immunoglobulin or may be modified to code for at least part of an altered immunoglobulin.

The inserted genetic material is expressed in the transgenic animal, resulting in production of an immunoglobulin derived at least in part from the inserted human immunoglobulin genetic material. It is found the genetic material is rearranged in the transgenic animal, so that a repertoire of immunoglobulins with part or parts derived from inserted genetic material may be produced, even if the inserted genetic material is incorporated in the germline in the wrong position or with the wrong geometry.

The inserted genetic material may be in the form of DNA cloned into prokaryotic vectors such as plasmids and/or cosmids. Larger DNA fragments are inserted using yeast artificial chromosome vectors (Burke et al., 1987; incorporated herein by reference), or by introduction of chromosome fragments (Richer and Lo, 1989; incorporated herein by reference). The inserted genetic material may be introduced to the host in conventional manner, for example by injection or other procedures into fertilized eggs or embryonic stem cells.

In preferred aspects, a host animal that initially does not carry genetic material encoding immunoglobulin constant regions is utilized, so that the resulting transgenic animal will use only the inserted human genetic material when producing immunoglobulins. This can be achieved either by using a naturally occurring mutant host lacking the relevant genetic material, or by artificially making mutants e.g., in cell lines ultimately to create a host from which the relevant genetic material has been removed.

Where the host animal carries genetic material encoding immunoglobulin constant regions, the transgenic animal will carry the naturally occurring genetic material and the inserted genetic material and will produce immunoglobulins derived from the naturally occurring genetic material, the inserted genetic material, and mixtures of both types of genetic material. In this case the desired immunoglobulin can be obtained by screening hybridomas derived from the transgenic animal, e.g., by exploiting the phenomenon of allelic exclusion of antibody gene expression or differential chromosome loss.

Once a suitable transgenic animal has been prepared, the animal is simply immunized with the desired immunogen. Depending on the nature of the inserted material, the animal may produce a chimeric immunoglobulin, e.g. of mixed mouse/human origin, where the genetic material of foreign origin encodes only part of the immunoglobulin; or the animal may produce an entirely foreign immunoglobulin, e.g. of wholly human origin, where the genetic material of foreign origin encodes an entire immunoglobulin.

Polyclonal antisera may be produced from the transgenic animal following immunization. Immunoglobulin-producing cells may be removed from the animal to produce the immunoglobulin of interest. Preferably, monoclonal antibodies are produced from the transgenic animal, e.g., by fusing spleen cells from the animal with myeloma cells and screening the resulting hybridomas to select those producing the desired antibody. Suitable techniques for such processes are described herein.

In an alternative approach, the genetic material may be incorporated in the animal in such a way that the desired antibody is produced in body fluids such as serum or external secretions of the animal, such as milk, colostrum or saliva. For example, by inserting in vitro genetic material encoding for at least part of a human immunoglobulin into a gene of a mammal coding for a milk protein and then introducing the gene to a fertilized egg of the mammal, e.g., by injection, the egg may develop into an adult female mammal producing milk containing immunoglobulin derived at least in part from the inserted human immunoglobulin genetic material. The desired antibody can then be harvested from the milk. Suitable techniques for carrying out such processes are known to those skilled in the art.

The foregoing transgenic animals are usually employed to produce human antibodies of a single isotype, more specifically an isotype that is essential for B cell maturation, such as IgM and possibly IgD. Another preferred method for producing human anti-aminophospholipid antibodies is described in U.S. Pat. Nos. 5,545,806; 5,569,825; 5,625,126; 5,633,425; 5,661,016; and 5,770,429; each incorporated by reference, wherein transgenic animals are described that are capable of switching from an isotype needed for B cell development to other isotypes.

In the development of a B lymphocyte, the cell initially produces IgM with a binding specificity determined by the productively rearranged $V_H$ and $V_L$ regions. Subsequently, each B cell and its progeny cells synthesize antibodies with the same L and H chain V regions, but they may switch the isotype of the H chain. The use of mu or delta constant regions is largely determined by alternate splicing, permitting IgM and IgD to be coexpressed in a single cell. The other heavy chain isotypes (gamma, alpha, and epsilon) are only expressed natively after a gene rearrangement event deletes the C mu and C delta exons. This gene rearrangement process, termed isotype switching, typically occurs by recombination between so called switch segments located immediately upstream of each heavy chain gene (except delta). The individual switch segments are between 2 and 10 kb in length, and consist primarily of short repeated sequences.

For these reasons, it is preferable that transgenes incorporate transcriptional regulatory sequences within about 1–2 kb upstream of each switch region that is to be utilized for isotype switching. These transcriptional regulatory sequences preferably include a promoter and an enhancer element, and more preferably include the 5' flanking (i.e., upstream) region that is naturally associated (i.e., occurs in germline configuration) with a switch region. Although a 5' flanking sequence from one switch region can be operably linked to a different switch region for transgene construction, in some embodiments it is preferred that each switch region incorporated in the transgene construct have the 5' flanking region that occurs immediately upstream in the naturally occurring germline configuration. Sequence information relating to immunoglobulin switch region sequences is known (Mills et al., 1990; Sideras et al., 1989; each incorporated herein by reference).

In the method described in U.S. Pat. Nos. 5,545,806; 5,569,825; 5,625,126; 5,633,425; 5,661,016; and 5,770,429, the human immunoglobulin transgenes contained within the transgenic animal function correctly throughout the pathway of B-cell development, leading to isotype switching. Accordingly, in this method, these transgenes are constructed so as to produce isotype switching and one or more of the following: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

An important requirement for transgene function is the generation of a primary antibody repertoire that is diverse enough to trigger a secondary immune response for a wide range of antigens. The rearranged heavy chain gene consists of a signal peptide exon, a variable region exon and a tandem array of multi-domain constant region regions, each of which is encoded by several exons. Each of the constant region genes encode the constant portion of a different class of immunoglobulins. During B-cell development, V region proximal constant regions are deleted leading to the expression of new heavy chain classes. For each heavy chain class, alternative patterns of RNA splicing give rise to both transmembrane and secreted immunoglobulins.

The human heavy chain locus consists of approximately 200 V gene segments spanning 2 Mb, approximately 30 D gene segments spanning about 40 kb, six J segments clustered within a 3 kb span, and nine constant region gene segments spread out over approximately 300 kb. The entire locus spans approximately 2.5 Mb of the distal portion of the long arm of chromosome 14. Heavy chain transgene fragments containing members of all six of the known $V_H$ families, the D and J gene segments, as well as the mu, delta, gamma 3, gamma 1 and alpha 1 constant regions are known (Berman et al., 1988; incorporated herein by reference). Genomic fragments containing all of the necessary gene segments and regulatory sequences from a human light chain locus is similarly constructed.

The expression of successfully rearranged immunoglobulin heavy and light transgenes usually has a dominant effect by suppressing the rearrangement of the endogenous immunoglobulin genes in the transgenic nonhuman animal. However, in certain embodiments, it is desirable to effect complete inactivation of the endogenous Ig loci so that hybrid immunoglobulin chains comprising a human variable region and a non-human (e.g., murine) constant region cannot be formed, for example by trans-switching between the transgene and endogenous Ig sequences. Using embryonic stem cell technology and homologous recombination, the endogenous immunoglobulin repertoire can be readily eliminated. In addition, suppression of endogenous Ig genes may be accomplished using a variety of techniques, such as antisense technology.

In other aspects of the invention, it may be desirable to produce a trans-switched immunoglobulin. Antibodies comprising such chimeric trans-switched immunoglobulins can be used for a variety of applications where it is desirable to have a non-human (e.g., murine) constant region, e.g., for retention of effector functions in the host. The presence of a murine constant region can afford advantages over a human constant region, for example, to provide murine effector functions (e.g., ADCC, murine complement fixation) so that such a chimeric antibody may be tested in a mouse disease model. Subsequent to the animal testing, the human variable region encoding sequence may be isolated, e.g., by PCR amplification or cDNA cloning from the source (hybridoma clone), and spliced to a sequence encoding a desired human constant region to encode a human sequence antibody more suitable for human therapeutic use.

E7. Humanized Anti-Aminophospholipid Antibodies

Human antibodies generally have at least three potential advantages for use in human therapy. First, because the effector portion is human, it may interact better with the other parts of the human immune system, e.g., to destroy target cells more efficiently by complement-dependent cytotoxicity (CDC) or antibody-dependent cellular cytotoxicity (ADCC). Second, the human immune system should not recognize the antibody as foreign. Third, the half-life in the human circulation will be similar to naturally occurring human antibodies, allowing smaller and less frequent doses to be given.

Various methods for preparing human anti-aminophospholipids are provided herein. In addition to human antibodies, "humanized" antibodies have many advantages. "Humanized" antibodies are generally chimeric or mutant monoclonal antibodies from mouse, rat, hamster, rabbit or other species, bearing human constant and/or variable region domains or specific changes. Techniques for generating a so-called "humanized" anti-aminophospholipid antibody are well known to those of skill in the art.

Humanized antibodies also share the foregoing advantages. First, the effector portion is still human. Second, the human immune system should not recognize the framework or constant region as foreign, and therefore the antibody response against such an injected antibody should be less than against a totally foreign mouse antibody. Third, injected humanized antibodies, as opposed to injected mouse antibodies, will presumably have a half-life more similar to naturally occurring human antibodies, also allowing smaller and less frequent doses.

A number of methods have been described to produce humanized antibodies. Controlled rearrangement of antibody domains joined through protein disulfide bonds to form new, artificial protein molecules or "chimeric" antibodies can be utilized (Konieczny et al., 1981; incorporated herein by reference). Recombinant DNA technology can also be used to construct gene fusions between DNA sequences encoding mouse antibody variable light and heavy chain domains and human antibody light and heavy chain constant domains (Morrison et al., 1984; incorporated herein by reference).

DNA sequences encoding the antigen binding portions or complementarity determining regions (CDR's) of murine monoclonal antibodies can be grafted by molecular means into the DNA sequences encoding the frameworks of human antibody heavy and light chains (Jones et al., 1986; Riechmann et al., 1988; each incorporated herein by reference). The expressed recombinant products are called "reshaped" or humanized antibodies, and comprise the framework of a human antibody light or heavy chain and the antigen recognition portions, CDR's, of a murine monoclonal antibody.

Another method for producing humanized antibodies is described in U.S. Pat. No. 5,639,641, incorporated herein by reference. The method provides, via resurfacing, humanized rodent antibodies that have improved therapeutic efficacy due to the presentation of a human surface in the variable region. In the method: (1) position alignments of a pool of antibody heavy and light chain variable regions is generated to give a set of heavy and light chain variable region framework surface exposed positions, wherein the alignment positions for all variable regions are at least about 98% identical; (2) a set of heavy and light chain variable region framework surface exposed amino acid residues is defined for a rodent antibody (or fragment thereof); (3) a set of heavy and light chain variable region framework surface exposed amino acid residues that is most closely identical to the set of rodent surface exposed amino acid residues is identified; (4) the set of heavy and light chain variable region framework surface exposed amino acid residues defined in step (2) is substituted with the set of heavy and light chain variable region framework surface exposed amino acid residues identified in step (3), except for those amino acid residues that are within 5 Å of any atom of any residue of the complementarity determining regions of the rodent antibody; and (5) the humanized rodent antibody having binding specificity is produced.

A similar method for the production of humanized antibodies is described in U.S. Pat. Nos. 5,693,762; 5,693,761; 5,585,089; and 5,530,101, each incorporated herein by reference. These methods involve producing humanized immunoglobulins having one or more complementarity determining regions (CDR's) and possible additional amino acids from a donor immunoglobulin and a framework region from an accepting human immunoglobulin. Each humanized immunoglobulin chain usually comprises, in addition to the CDR's, amino acids from the donor immunoglobulin framework that are capable of interacting with the CDR's to effect binding affinity, such as one or more amino acids that are immediately adjacent to a CDR in the donor immunoglobulin or those within about 3 Å as predicted by molecular modeling. The heavy and light chains may each be designed by using any one, any combination, or all of the various position criteria described in U.S. Pat. Nos. 5,693,762; 5,693,761; 5,585,089; and 5,530,101, each incorporated herein by reference. When combined into an intact antibody, the humanized immunoglobulins are substantially non-immunogenic in humans and retain substantially the same affinity as the donor immunoglobulin to the original antigen.

An additional method for producing humanized antibodies is described in U.S. Pat. Nos. 5,565,332 and 5,733,743, each incorporated herein by reference. This method combines the concept of humanizing antibodies with the phagemid libraries also described in detail herein. In a general sense, the method utilizes sequences from the antigen binding site of an antibody or population of antibodies directed against an antigen of interest. Thus for a single rodent antibody, sequences comprising part of the antigen binding site of the antibody may be combined with diverse repertoires of sequences of human antibodies that can, in combination, create a complete antigen binding site.

The antigen binding sites created by this process differ from those created by CDR grafting, in that only the portion of sequence of the original rodent antibody is likely to make contacts with antigen in a similar manner. The selected human sequences are likely to differ in sequence and make alternative contacts with the antigen from those of the original binding site. However, the constraints imposed by binding of the portion of original sequence to antigen and the shapes of the antigen and its antigen binding sites, are likely to drive the new contacts of the human sequences to the same region or epitope of the antigen. This process has therefore been termed "epitope imprinted selection" (EIS).

Starting with an animal antibody, one process results in the selection of antibodies that are partly human antibodies. Such antibodies may be sufficiently similar in sequence to human antibodies to be used directly in therapy or after alteration of a few key residues. Sequence differences between the rodent component of the selected antibody with human sequences could be minimized by replacing those residues that differ with the residues of human sequences, for example, by site directed mutagenesis of individual residues, or by CDR grafting of entire loops. However, antibodies with entirely human sequences can also be created. EIS therefore offers a method for making partly human or entirely human antibodies that bind to the same epitope as animal or partly human antibodies respectively. In EIS, repertoires of antibody fragments can be displayed on the surface of filamentous phase and the genes encoding fragments with antigen binding activities selected by binding of the phage to antigen.

Additional methods for humanizing antibodies contemplated for use in the present invention are described in U.S. Pat. Nos. 5,750,078; 5,502,167; 5,705,154; 5,770,403;

5,698,417; 5,693,493; 5,558,864; 4,935,496; and 4,816,567, each incorporated herein by reference.

E8. Mutagenesis by PCR

Site-specific mutagenesis is a technique useful in the preparation of individual antibodies through specific mutagenesis of the underlying DNA. The technique further provides a ready ability to prepare and test sequence variants, incorporating one or more of the foregoing considerations, whether humanizing or not, by introducing one or more nucleotide sequence changes into the DNA.

Although many methods are suitable for use in mutagenesis, the use of the polymerase chain reaction (PCR™) is generally now preferred. This technology offers a quick and efficient method for introducing desired mutations into a given DNA sequence. The following text particularly describes the use of PCR™ to introduce point mutations into a sequence, as may be used to change the amino acid encoded by the given sequence. Adaptations of this method are also suitable for introducing restriction enzyme sites into a DNA molecule.

In this method, synthetic oligonucleotides are designed to incorporate a point mutation at one end of an amplified segment. Following PCR™, the amplified fragments are blunt-ended by treating with Klenow fragments, and the blunt-ended fragments are then ligated and subcloned into a vector to facilitate sequence analysis.

To prepare the template DNA that one desires to mutagenize, the DNA is subcloned into a high copy number vector, such as pUC19, using restriction sites flanking the area to be mutated. Template DNA is then prepared using a plasmid miniprep. Appropriate oligonucleotide primers that are based upon the parent sequence, but which contain the desired point mutation and which are flanked at the 5' end by a restriction enzyme site, are synthesized using an automated synthesizer. It is generally required that the primer be homologous to the template DNA for about 15 bases or so. Primers may be purified by denaturing polyacrylamide gel electrophoresis, although this is not absolutely necessary for use in PCR™. The 5' end of the oligonucleotides should then be phosphorylated.

The template DNA should be amplified by PCR™, using the oligonucleotide primers that contain the desired point mutations. The concentration of $MgCl_2$ in the amplification buffer will generally be about 15 mM. Generally about 20–25 cycles of PCR™ should be carried out as follows: denaturation, 35 sec. at 95° C.; hybridization, 2 min. at 50° C.; and extension, 2 min. at 72° C. The PCR™ will generally include a last cycle extension of about 10 min. at 72° C. After the final extension step, about 5 units of Klenow fragments should be added to the reaction mixture and incubated for a further 15 min. at about 30° C. The exonuclease activity of the Klenow fragments is required to make the ends flush and suitable for blunt-end cloning.

The resultant reaction mixture should generally be analyzed by nondenaturing agarose or acrylamide gel electrophoresis to verify that the amplification has yielded the predicted product. One would then process the reaction mixture by removing most of the mineral oils, extracting with chloroform to remove the remaining oil, extracting with buffered phenol and then concentrating by precipitation with 100% ethanol. Next, one should digest about half of the amplified fragments with a restriction enzyme that cuts at the flanking sequences used in the oligonucleotides. The digested fragments are purified on a low gelling/melting agarose gel.

To subclone the fragments and to check the point mutation, one would subclone the two amplified fragments into an appropriately digested vector by blunt-end ligation. This would be used to transform E. coli, from which plasmid DNA could subsequently be prepared using a miniprep. The amplified portion of the plasmid DNA would then be analyzed by DNA sequencing to confirm that the correct point mutation was generated. This is important as Taq DNA polymerase can introduce additional mutations into DNA fragments.

The introduction of a point mutation can also be effected using sequential PCR™ steps. In this procedure, the two fragments encompassing the mutation are annealed with each other and extended by mutually primed synthesis. This fragment is then amplified by a second PCR™ step, thereby avoiding the blunt-end ligation required in the above protocol. In this method, the preparation of the template DNA, the generation of the oligonucleotide primers and the first PCR™ amplification are performed as described above. In this process, however, the chosen oligonucleotides should be homologous to the template DNA for a stretch of between about 15 and about 20 bases and must also overlap with each other by about 10 bases or more.

In the second PCR™ amplification, one would use each amplified fragment and each flanking sequence primer and carry PCR™ for between about 20 and about 25 cycles, using the conditions as described above. One would again subclone the fragments and check that the point mutation was correct by using the steps outlined above.

In using either of the foregoing methods, it is generally preferred to introduce the mutation by amplifying as small a fragment as possible. Of course, parameters such as the melting temperature of the oligonucleotide, as will generally be influenced by the GC content and the length of the oligo, should also be carefully considered. The execution of these methods, and their optimization if necessary, will be known to those of skill in the art, and are further described in various publications, such as Current Protocols in Molecular Biology, 1995, incorporated herein by reference.

When performing site-specific mutagenesis, Table A can be employed as a reference.

TABLE A

| Amino Acids | Codons |
|---|---|
| Alanine | Ala A GCA GCC GCG GCU |
| Cysteine | Cys C UGC UGU |
| Aspartic acid | Asp D GAC GAU |
| Glutamic acid | Glu E GAA GAG |
| Phenylalanine | Phe F UUC UUU |
| Glycine | Gly G GGA GGC GGG GGU |
| Histidine | His H CAC CAU |
| Isoleucine | Ile i AUA AUC AUU |
| Lysine | Lys K AAA AAG |
| Leucine | Leu L UUA UUG CUA CUC CUG CUU |
| Methionine | Met M AUG |
| Asparagine | Asn N AAC AAU |
| Proline | Pro P CCA CCC CCG CCU |
| Glutamine | Gln Q CAA CAG |
| Arginine | Arg R AGA AGG CGA CGC CGG CGU |
| Serine | Ser S AGC AGU UCA UCC UCG UCU |
| Threonine | Thr T ACA ACC ACG ACU |
| Valine | Val V GUA GUC GUG GUU |
| Tryptophan | Trp W UGG |
| Tyrosine | Tyr Y UACUAU |

E9. Recombinant Expression and Delivery

Given that many methods are available for cloning antibodies, anti-aminophospholipid antibodies may be prepared by routine methods of recombinant expression. The term "expression construct" is meant to include any type of genetic construct containing a nucleic acid coding for a gene product in which part or all of the nucleic acid encoding sequence is capable of being transcribed. The transcript will generally be translated into a protein. Thus, as intended herein, expression preferably includes both transcription of an anti-aminophospholipid antibody gene or DNA and translation of the mRNA into an anti-aminophospholipid antibody protein product.

For the expression of an anti-aminophospholipid antibody, once a suitable clone or clones have been obtained, whether they be cDNA based or genomic, one may proceed to prepare an expression system or "construct" for recombinant antibody production. The engineering of DNA segment(s) for expression in a prokaryotic or eukaryotic system will be performed by techniques generally known to those of skill in recombinant antibody expression (Sambrook et al., 1989; incorporated herein by reference). In order for the construct to effect expression of an anti-aminophospholipid antibody transcript, the polynucleotide encoding the antibody will preferably be under the transcriptional control of a promoter that promotes expression in the chosen host cell.

Recombinantly produced antibodies may be purified and formulated for human administration. Alternatively, nucleic acids encoding anti-aminophospholipid antibodies may be delivered via gene therapy. Although naked recombinant DNA or plasmids may be employed, the use of liposomes or vectors is preferred. The ability of certain viruses to enter cells via receptor-mediated endocytosis and to integrate into host cell genome and express viral genes stably and efficiently have made them attractive candidates for the transfer of foreign genes into mammalian cells. Preferred gene therapy vectors for use in the present invention will generally be viral vectors.

Retroviruses have promise as gene delivery vectors due to their ability to integrate their genes into the host genome, transferring a large amount of foreign genetic material, infecting a broad spectrum of species and cell types and of being packaged in special cell-lines. Other viruses, such as adenovirus, herpes simplex viruses (HSV), cytomegalovirus (CMV), and adeno-associated virus (AAV), such as those described by U.S. Pat. No. 5,139,941 (incorporated herein by reference), may also be engineered to serve as vectors for gene transfer.

Although some viruses that can accept foreign genetic material are limited in the number of nucleotides they can accommodate and in the range of cells they infect, these viruses have been demonstrated to successfully effect gene expression. However, adenoviruses do not integrate their genetic material into the host genome and therefore do not require host replication for gene expression, making them ideally suited for rapid, efficient, heterologous gene expression. Techniques for preparing replication-defective infective viruses are well known in the art.

In certain further embodiments, the gene therapy vector will be HSV. A factor that makes HSV an attractive vector is the size and organization of the genome. Because HSV is large, incorporation of multiple genes or expression cassettes is less problematic than in other smaller viral systems. In addition, the availability of different viral control sequences with varying performance (e.g., temporal, strength) makes it possible to control expression to a greater extent than in other systems. It also is an advantage that the virus has relatively few spliced messages, further easing genetic manipulations. HSV also is relatively easy to manipulate and can be grown to high titers.

Of course, in using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

E10. Antibody Fragments

Irrespective of the source of the original anti-aminophospholipid antibody, either the intact antibody, antibody multimers, or any one of a variety of functional, antigen-binding regions of the antibody may be used in the present invention. Exemplary functional regions include scFv, Fv, Fab', Fab and F(ab')$_2$ fragments of the anti-aminophospholipid antibodies. Techniques for preparing such constructs are well known to those in the art and are further exemplified herein.

The choice of antibody construct may be influenced by various factors. For example, prolonged half-life can result from the active readsorption of intact antibodies within the kidney, a property of the Fc piece of immunoglobulin. IgG based antibodies, therefore, are expected to exhibit slower blood clearance than their Fab' counterparts. However, Fab' fragment-based compositions will generally exhibit better tissue penetrating capability.

Fab fragments can be obtained by proteolysis of the whole immunoglobulin by the non-specific thiol protease, papain. Papain must first be activated by reducing the sulphydryl group in the active site with cysteine, 2-mercaptoethanol or dithiothreitol. Heavy metals in the stock enzyme should be removed by chelation with EDTA (2 mM) to ensure maximum enzyme activity. Enzyme and substrate are normally mixed together in the ratio of 1:100 by weight. After incubation, the reaction can be stopped by irreversible alkylation of the thiol group with iodoacetamide or simply by dialysis. The completeness of the digestion should be monitored by SDS-PAGE and the various fractions separated by protein A-Sepharose or ion exchange chromatography.

The usual procedure for preparation of F(ab')$_2$ fragments from IgG of rabbit and human origin is limited proteolysis by the enzyme pepsin. The conditions, 100× antibody excess w/w in acetate buffer at pH 4.5, 37° C., suggest that antibody is cleaved at the C-terminal side of the inter-heavy-chain disulfide bond. Rates of digestion of mouse IgG may vary with subclass and it may be difficult to obtain high yields of active F(ab')$_2$ fragments without some undigested or completely degraded IgG. In particular, IgG$_{2b}$ is highly susceptible to complete degradation. The other subclasses require different incubation conditions to produce optimal results, all of which is known in the art.

Digestion of rat IgG by pepsin requires conditions including dialysis in 0.1 M acetate buffer, pH 4.5, and then incubation for four hours with 1% w/w pepsin; IgG$_1$ and IgG$_{2a}$ digestion is improved if first dialyzed against 0.1 M formate buffer, pH 2.8, at 4° C., for 16 hours followed by acetate buffer. IgG$_{2b}$ gives more consistent results with incubation in staphylococcal V8 protease (3% w/w) in 0.1 M sodium phosphate buffer, pH 7.8, for four hours at 37° C.

The following patents and patent applications are specifically incorporated herein by reference for the purposes of even further supplementing the present teachings regarding the preparation and use of functional, antigen-binding regions of antibodies, including scFv, Fv, Fab', Fab and F(ab')$_2$ fragments of the anti-aminophospholipid antibodies: U.S. Pat. Nos. 5,855,866 and 5,877,289; 5,965,132; 6,004,555; and 6,093,399.

F. Pharmaceutical Compositions

The most basic pharmaceutical compositions of the present invention will generally comprise an effective amount of at least a first naked anti-aminophospholipid antibody, or antigen-binding fragment thereof, dissolved or dispersed in a pharmaceutically acceptable carrier or aqueous medium. Combined therapeutics are also contemplated, and the same type of underlying pharmaceutical compositions may be employed for both single and combined medicaments.

The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by FDA Office of Biologics standards. Supplementary active ingredients can also be incorporated into the compositions.

F1. Parenteral Formulations

The anti-aminophospholipid antibodies of the present invention will most often be formulated for parenteral administration, e.g., formulated for injection via the intravenous, intramuscular, sub-cutaneous, transdermal, or other such routes, including peristaltic administration and direct instillation into a tumor or disease site (intracavity administration). The preparation of an aqueous composition that contains an anti-aminophospholipid antibody as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

The anti-aminophospholipid antibody compositions can be formulated into a sterile aqueous composition in a neutral or salt form. Solutions of the anti-aminophospholipid antibodies as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate and gelatin.

Prior to or upon formulation, the anti-aminophospholipid antibodies should be extensively dialyzed to remove undesired small molecular weight molecules, and/or lyophilized for more ready formulation into a desired vehicle, where appropriate. Sterile injectable solutions are prepared by incorporating the active anti-aminophospholipid antibodies in the required amount in the appropriate solvent with various of the other ingredients enumerated above, as desired, followed by filtered sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active anti-aminophospholipid antibody ingredient, plus any additional desired ingredient from a previously sterile-filtered solution thereof.

Suitable pharmaceutical compositions in accordance with the invention will generally include an amount of the anti-aminophospholipid antibody admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards.

Upon formulation, anti-aminophospholipid antibody solutions will be administered in a manner compatible with the dosage formulation and in such amount as is therapeutically effective. Formulations are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, liposomal forms and the like. Pharmaceutical "slow release" capsules or compositions may also be used. Slow release formulations are generally designed to give a constant drug level over an extended period and may be used to deliver anti-aminophospholipid antibodies in accordance with the present invention.

F2. Liposomes and Nanocapsules

In certain embodiments, liposomes and/or nanoparticles may also be employed with the anti-aminophospholipid antibodies. The formation and use of liposomes is generally known to those of skill in the art, as summarized below.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 $\mu$m. Sonication of MLVs results in the formation of small unilamellar vesicles (SUVs) with diameters in the range of 200 to 500 Å, containing an aqueous solution in the core.

Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

Nanocapsules can generally entrap compounds in a stable and reproducible way. To avoid side effects due to intracellular polymeric overloading, such ultrafine particles (sized around 0.1 $\mu$m) should be designed using polymers able to be degraded in vivo. Biodegradable polyalkyl-cyanoacrylate nanoparticles that meet these requirements are contemplated for use in the present invention, and such particles may be are easily made.

G. Therapeutic Kits

This invention also provides therapeutic kits comprising anti-aminophospholipid antibodies for use in the present treatment methods. Such kits will generally contain, in suitable container means, a pharmaceutically acceptable formulation of at least one anti-aminophospholipid antibody. The kits may also contain other pharmaceutically acceptable formulations, either for diagnosis/imaging or combined therapy. For example, such kits may contain any one or more of a range of chemotherapeutic or radiotherapeutic drugs; anti-angiogenic agents; anti-tumor cell antibodies; and/or anti-tumor vasculature or anti-tumor stroma immunotoxins or coaguligands.

The kits may have a single container (container means) that contains the anti-aminophospholipid antibody, with or without any additional components, or they may have distinct containers for each desired agent. Where combined therapeutics are provided, a single solution may be premixed, either in a molar equivalent combination, or with one component in excess of the other. Alternatively, each of the anti-aminophospholipid antibody and other anti-cancer agent components of the kit may be maintained separately within distinct containers prior to administration to a patient.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

The containers of the kit will generally include at least one vial, test tube, flask, bottle, syringe or other container means, into which the anti-aminophospholipid antibody, and any other desired agent, may be placed and, preferably, suitably aliquoted. Where separate components are included, the kit will also generally contain a second vial or other container into which these are placed, enabling the administration of separated designed doses. The kits may also comprise a second/third container means for containing a sterile, pharmaceutically acceptable buffer or other diluent.

The kits may also contain a means by which to administer the anti-aminophospholipid antibody to an animal or patient, e.g., one or more needles or syringes, or even an eye dropper, pipette, or other such like apparatus, from which the formulation may be injected into the animal or applied to a diseased area of the body. The kits of the present invention will also typically include a means for containing the vials, or such like, and other component, in close confinement for commercial sale, such as, e.g., injection or blow-molded plastic containers into which the desired vials and other apparatus are placed and retained.

H. Tumor Treatment

The most important use of the present invention is in the treatment of vascularized, malignant tumors; with the treatment of benign tumors, such as BPH, also being contemplated. The invention may also be used in the therapy of other diseases and disorders having, as a component of the disease, prothrombotic blood vessels. Such vasculature-associated diseases include diabetic retinopathy, macular degeneration, vascular restenosis, including restenosis following angioplasty, arteriovenous malformations (AVM), meningioma, hemangioma, neovascular glaucoma and psoriasis; and also angiofibroma, arthritis, rheumatoid arthritis, atherosclerotic plaques, corneal graft neovascularization, hemophilic joints, hypertrophic scars, osler-weber syndrome, pyogenic granuloma retrolental fibroplasia, scleroderma, trachoma, vascular adhesions, synovitis, dermatitis, various other inflammatory diseases and disorders, and even endometriosis.

The anti-aminophospholipid antibody treatment of the invention is most preferably exploited for the treatment of solid tumors. Such uses may employ anti-aminophospholipid antibodies alone or in combination with chemotherapeutic, radiotherapeutic, apoptopic, anti-angiogenic agents and/or immunotoxins or coaguligands. The anti-aminophospholipid antibody methods provided by this invention are broadly applicable to the treatment of any malignant tumor having a vascular component. Typical vascularized tumors are the solid tumors, particularly carcinomas, which require a vascular component for the provision of oxygen and nutrients. Exemplary solid tumors that may be treated using the invention include, but are not limited to, carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, neuroblastomas, and the like.

The present invention is contemplated for use in the treatment of any patient that presents with a solid tumor. However, in that this invention is particularly successful in the treatment of solid tumors of moderate or large sizes, patients in these categories are likely to receive more significant benefits from treatment in accordance with the methods and compositions provided herein.

Therefore, in general, the invention can be used to treat tumors of about 0.3–0.5 cm and upwards, although it is a better use of the invention to treat tumors of greater than 0.5 cm in size. From the studies already conducted in acceptable animal models, it is believed that patients presenting with tumors of between about 1.0 and about 2.0 cm in size will be in the preferred treatment group of patients for anti-aminophospholipid antibody therapy, although tumors up to and including the largest tumors found in humans may also be treated.

Although the present invention is not generally intended as a preventative or prophylactic treatment, use of the invention is certainly not confined to the treatment of patients having tumors of only moderate or large sizes. There are many reasons underlying this aspect of the breadth of the invention. For example, a patient presenting with a primary tumor of moderate size or above may also have various other metastatic tumors that are considered to be small-sized or even in the earlier stages of metastatic tumor seeding. Given that the anti-aminophospholipid antibodies, or combinations, of the invention are generally administered into the systemic circulation of a patient, they will naturally have effects on the secondary, smaller and metastatic tumors, although this may not be the primary intent of the treatment. Furthermore, even in situations where the tumor mass as a whole is a single small tumor, certain beneficial anti-tumor effects will result from the use of the present anti-aminophospholipid antibody treatment.

The guidance provided herein regarding the most suitable patients for use in connection with the present invention is intended as teaching that certain patient's profiles may assist with the selection of patients for treatment by the present invention. The pre-selection of certain patients, or categories of patients, does not in any way negate the basic usefulness of the present invention in connection with the treatment of all patients having a vascularized tumor. A further consideration is the fact that the assault on the tumor provided by the anti-aminophospholipid antibody therapy of the invention may predispose the tumor to further therapeutic treatment, such that the subsequent treatment results in an overall synergistic effect or even leads to total remission or cure.

It is not believed that any particular type of tumor should be excluded from treatment using the present invention. However, the type of tumor cells may be relevant to the use of the invention in combination with secondary therapeutic agents, particularly chemotherapeutics and anti-tumor cell immunotoxins. As the effect of the present therapy is to destroy the tumor vasculature, and as the vasculature is substantially or entirely the same in all solid tumors, it will be understood that the present anti-aminophospholipid methodology is widely or entirely applicable to the treatment of all solid tumors, irrespective of the particular phenotype or genotype of the tumor cells themselves. The data presented herein is compelling as it shows impressive results in a tumor model that is resistant to necrosis.

Therapeutically effective doses of anti-aminophospholipid antibodies are readily determinable using data from an animal model, as shown in the studies detailed herein. Experimental animals bearing solid tumors are frequently used to optimize appropriate therapeutic doses prior to translating to a clinical environment. Such models are known to be very reliable in predicting effective anti-cancer strategies. For example, mice bearing solid tumors, such as used in the Examples, are widely used in pre-clinical testing. The inventors have used such art-accepted mouse models to determine working ranges of naked anti-aminophospholipid antibodies that give beneficial anti-tumor effects with minimal toxicity.

As is known in the art, there are realistic objectives that may be used as a guideline in connection with pre-clinical testing before proceeding to clinical treatment. However, due to the safety already demonstrated in accepted models, pre-clinical testing of the present invention will be more a matter of optimization, rather than to confirm effectiveness. Thus, pre-clinical testing may be employed to select the most advantageous anti-aminophospholipid antibodies, doses or combinations.

Any anti-aminophospholipid antibody dose, or combined medicament, that results in any consistent detectable tumor vasculature destruction, thrombosis and anti-tumor effects will still define a useful invention. Destructive, thrombotic and necrotic effects should be observed in between about 10% and about 40–50% of the tumor blood vessels and tumor tissues, upwards to between about 50% and about 99% of such effects being observed. The present invention may also be effective against vessels downstream of the tumor, i.e., target at least a sub-set of the draining vessels, particularly as cytokines released from the tumor will be acting on these vessels, changing their antigenic profile.

It will also be understood that even in such circumstances where the anti-tumor effects of the anti-aminophospholipid antibody dose, or combined therapy, are towards the low end of this range, it may be that this therapy is still equally or even more effective than all other known therapies in the context of the particular tumor targets. It is unfortunately evident to a clinician that certain tumors cannot be effectively treated in the intermediate or long term, but that does not negate the usefulness of the present therapy, particularly where it is at least about as effective as the other strategies generally proposed.

In designing appropriate doses of anti-aminophospholipid antibodies, or combined therapeutics, for the treatment of vascularized tumors, one may readily extrapolate from the animal studies described herein in order to arrive at appropriate doses for clinical administration. To achieve this conversion, one would account for the mass of the agents administered per unit mass of the experimental animal and, preferably, account for the differences in the body surface area between the experimental animal and the human patient. All such calculations are well known and routine to those of ordinary skill in the art.

For example, in taking the successful dose of 20 $\mu$g antibody per mouse (total body weight of about 20 g), and applying standard calculations based upon mass and surface area, effective doses for use in human patients would be between about 1 mg and about 500 mgs antibody per patient, and preferably, between about 10 mgs and about 100 mgs antibody per patient. In addition to all variable clinical and therapeutic parameters, this variation also accounts for the present tumor necrosis data being generated using a tumor model that is resistant to necrosis, and in which less tumor vessel staining was observed than in other models.

Accordingly, using this information, the inventors contemplate that useful low doses of naked anti-aminophospholipid antibodies for human administration will be about 1, 2, 3, 4, 5, 6, 7, 8, 9, 10, 15, 20, 25 or about 30 mgs or so per patient; and useful high doses of naked anti-aminophospholipid antibodies for human administration will be about 250, 275, 300, 325, 350, 375, 400, 425, 450, 475 or about 500 mgs or so per patient. Useful intermediate doses of naked anti-aminophospholipid antibodies for human administration are contemplated to be about 35, 40, 50, 60, 70, 80, 90, 100, 125, 150, 175, 200 or about 225 mgs or so per patient. Any particular range using any of the foregoing recited exemplary doses or any value intermediate between the particular stated ranges is also contemplated.

In general, dosage ranges of between about 5–100 mgs, about 10–80 mgs, about 20–70 mgs, about 25–60 mgs, or about 30–50 mgs or so of antibody per patient will be preferred. Notwithstanding these stated ranges, it will be understood that, given the parameters and detailed guidance presented herein, further variations in the active or optimal ranges will be encompassed within the present invention. Although doses in and around about 5 or 10 to about 70, 80, 90 or 100 mgs per patient are currently preferred, it will be understood that lower doses may be more appropriate in combination with other agents, and that high doses can still be tolerated, particularly given the enhanced safety of the unconjugated anti-aminophospholipid antibodies for use in the invention. The use of human or humanized naked anti-aminophospholipid antibodies renders the present invention even safer for clinical use, further reducing the chances of significant toxicity or side effects in healthy tissues.

The intention of the therapeutic regimens of the present invention is generally to produce significant anti-tumor effects whilst still keeping the dose below the levels associated with unacceptable toxicity. In addition to varying the dose itself, the administration regimen can also be adapted to optimize the treatment strategy. A currently preferred treatment strategy is to administer between about 1–500 mgs, and preferably, between about 10–100 mgs of the anti-aminophospholipid antibody, or therapeutic cocktail containing such, about 3 times within about a 7 day period. For example, doses would be given on about day 1, day 3 or 4 and day 6 or 7.

In administering the particular doses themselves, one would preferably provide a pharmaceutically acceptable composition (according to FDA standards of sterility, pyrogenicity, purity and general safety) to the patient systemically. Intravenous injection is generally preferred, and the most preferred method is to employ a continuous infusion over a time period of about 1 or 2 hours or so. Although it is not required to determine such parameters prior to treatment using the present invention, it should be noted that the studies detailed herein result in at least some thrombosis being observed specifically in the blood vessels of a solid tumor within about 12–24 hours of injection, and that the tumor cells themselves begin to die within about 24 to 72 hours. Widespread tumor necrosis is generally observed in the next about 48–96 hours, up to and including greater than 60% necrosis being observed.

Naturally, before wide-spread use, clinical trials will be conducted. The various elements of conducting a clinical trial, including patient treatment and monitoring, will be known to those of skill in the art in light of the present disclosure. The following information is being presented as a general guideline for use in establishing such trials.

Patients chosen for the first anti-aminophospholipid antibody treatment studies will have failed to respond to at least one course of conventional therapy, and will have objectively measurable disease as determined by physical examination, laboratory techniques, and/or radiographic procedures. Any chemotherapy should be stopped at least 2 weeks before entry into the study. Where murine monoclonal antibodies or antibody portions are employed, the patients should have no history of allergy to mouse immunoglobulin.

Certain advantages will be found in the use of an indwelling central venous catheter with a triple lumen port. The anti-aminophospholipid antibodies should be filtered, for example, using a $0.22\mu$ filter, and diluted appropriately, such as with saline, to a final volume of 100 ml. Before use, the test sample should also be filtered in a similar manner, and its concentration assessed before and after filtration by determining the $A_280$. The expected recovery should be within the range of 87% to 99%, and adjustments for protein loss can then be accounted for.

These anti-aminophospholipid antibodies may be administered over a period of approximately 4–24 hours, with each patient receiving 2–4 infusions at 2–7 day intervals. Administration can also be performed by a steady rate of infusion over a 7 day period. The infusion given at any dose level should be dependent upon any toxicity observed. Hence, if Grade II toxicity was reached after any single infusion, or at a particular period of time for a steady rate infusion, further doses should be withheld or the steady rate infusion stopped unless toxicity improved. Increasing doses of anti-aminophospholipid antibodies should be administered to groups of patients until approximately 60% of patients showed unacceptable Grade III or IV toxicity in any category. Doses that are $\frac{2}{3}$ of this value are defined as the safe dose.

Physical examination, tumor measurements, and laboratory tests should, of course, be performed before treatment and at intervals up to 1 month later. Laboratory tests should include complete blood counts, serum creatinine, creatine kinase, electrolytes, urea, nitrogen, SGOT, bilirubin, albumin, and total serum protein. Serum samples taken up to 60 days after treatment should be evaluated by radioimmunoassay for the presence of the administered anti-aminophospholipid antibodies, and antibodies against any portions thereof. Immunological analyses of sera, using any standard assay such as, for example, an ELISA or RIA, will allow the pharmacokinetics and clearance of the anti-aminophospholipid therapeutic agent to be evaluated.

To evaluate the anti-tumor responses, the patients should be examined at 48 hours to 1 week and again at 30 days after the last infusion. When palpable disease was present, two perpendicular diameters of all masses should be measured daily during treatment, within 1 week after completion of therapy, and at 30 days. To measure nonpalpable disease, serial CT scans could be performed at 1-cm intervals throughout the chest, abdomen, and pelvis at 48 hours to 1 week and again at 30 days. Tissue samples should also be evaluated histologically, and/or by flow cytometry, using biopsies from the disease sites or even blood or fluid samples if appropriate.

Clinical responses may be defined by acceptable measure. For example, a complete response may be defined by the disappearance of all measurable tumor 1 month after treatment. Whereas a partial response may be defined by a 50% or greater reduction of the sum of the products of perpendicular diameters of all evaluable tumor nodules 1 month after treatment, with no tumor sites showing enlargement.

Similarly, a mixed response may be defined by a reduction of the product of perpendicular diameters of all measurable lesions by 50% or greater 1 month after treatment, with progression in one or more sites.

In light of results from clinical trials, such as those described above, an even more precise treatment regimen may be formulated. Even so, some variation in dosage may later be necessary depending on the condition of the subject being treated. The physician responsible for administration will, in light of the present disclosure, be able to determine the appropriate dose for the individual subject. Such optimization and adjustment is routinely carried out in the art and by no means reflects an undue amount of experimentation.

I. Tumor Imaging

The present invention further provides combined tumor treatment and imaging methods, based upon anti-aminophospholipid binding ligands. Anti-aminophospholipid binding proteins or antibodies that are linked to one or more detectable agents are envisioned for use in pre-imaging the tumor, forming a reliable image prior to the treatment, which itself targets the aminophospholipid markers. In addition to antibodies, the use of detectably labeled annexins and other aminophospholipid binding ligands is contemplated, as disclosed and claimed in first and second provisional applications Ser. No. 60/092,589 (filed Jul. 13, 1998) and Ser. No. 60/110,600 (filed Dec. 2, 1998) and in co-filed U.S. and PCT patent application Ser. No. 09/351,457, now U.S. Pat. No. 6,132,694; Ser. No. 09/351,598, Ser. No. 09/351,149 and WO 00/02584, each specifically incorporated herein by reference.

The anti-aminophospholipid imaging ligands or antibodies, or conjugates thereof, will generally comprise an anti-aminophospholipid antibody or binding ligand operatively attached, or conjugated to, a detectable label. "Detectable labels" are compounds or elements that can be detected due to their specific functional properties, or chemical characteristics, the use of which allows the component to which they are attached to be detected, and further quantified if desired. Preferably, the detectable labels are those detectable in vivo using non-invasive methods.

Antibody and binding protein conjugates for use as diagnostic agents generally fall into two classes, those for use in in vitro diagnostics, such as in a variety of immunoassays, and those for use in vivo diagnostic protocols. It is the in vivo imaging methods that are particularly intended for use with this invention.

Many appropriate imaging agents are known in the art, as are methods for their attachment to antibodies and binding ligands (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the antibody (U.S. Pat. No. 4,472,509). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

An example of detectable labels are the paramagnetic ions. In this case, suitable ions include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred.

Ions useful in other contexts, such as X-ray imaging, include but are not limited to lanthanum (III), gold (III), lead (II), and especially bismuth (III). Fluorescent labels include rhodamine, fluorescein and renographin. Rhodamine and fluorescein are often linked via an isothiocyanate intermediate.

In the case of radioactive isotopes for diagnostic applications, suitable examples include $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technetium$^{99m}$ and yttrium$^{90}$. $^{125}$I is often being preferred for use in certain embodiments, and technicium$^{99m}$ and indium$^{111}$ are also often preferred due to their low energy and suitability for long range detection.

Radioactively labeled anti-aminophospholipid antibodies and binding ligands for use in the present invention may be produced according to well-known methods in the art. For instance, intermediary functional groups that are often used to bind radioisotopic metallic ions to antibodies are diethylenetriaminepentaacetic acid (DTPA) and ethylene diaminetetracetic acid (EDTA).

Monoclonal antibodies can also be iodinated by contact with sodium or potassium iodide and a chemical oxidizing agent such as sodium hypochlorite, or an enzymatic oxidizing agent, such as lactoperoxidase. Anti-aminophospholipid antibodies according to the invention may be labeled with technetium-$^{99}$m by ligand exchange process, for example, by reducing pertechnate with stannous solution, chelating the reduced technetium onto a Sephadex column and applying the antibody to this column; or by direct labeling techniques, e.g., by incubating pertechnate, a reducing agent such as $SNCl_2$, a buffer solution such as sodium-potassium phthalate solution, and the antibody.

Any of the foregoing type of detectably labeled anti-aminophospholipid antibodies and aminophospholipid binding ligands may be used in the imaging aspects of the present invention. Although not previously proposed for use in combined tumor imaging and treatment, the detectably-labeled annexins of U.S. Pat. No. 5,627,036; WO 95/19791; WO 95/27903; WO 95/34315; WO 96/17618; and WO 98/04294; each incorporated herein by reference; may also be employed.

WO 95/27903 (incorporated herein by reference) provides annexins for use in detecting apoptotic cells. Any of the annexin-detectable agent markers of WO 95/27903 may be used herein, although it will be known that certain of these are more suitable for in vitro uses. WO 95/27903 is also specifically incorporated herein by reference for purposes of providing detectable kits that may be adapted for combined use with the therapeutics of the present invention.

Each of WO 95/19791; WO 95/34315; WO 96/17618; and WO 98/04294; are also incorporated herein by reference for purposes of further describing radiolabelled annexin conjugates for diagnostic imaging. The intent of each of the foregoing documents is to provide radiolabelled annexins for use in imaging vascular thromboses, particularly in or near the heart, such as in deep vein thrombosis, pulmonary embolism, myocardial infarction, atrial fibrillation, problems with prosthetic cardiovascular materials, stroke, and the like. These radiolabelled annexins were also proposed for use in imaging activated platelets, e.g., in conditions such as abscesses, restenosis, inflammation of joints, clots in cerebral arteries, etc.

U.S. Pat. No. 5,627,036 (incorporated herein by reference) also generally concerns 'annexine' (annexin) binding ligands for use in analyzing platelet phosphatidylserine. It is explained in U.S. Pat. No. 5,627,036 that hemostatic disorders, such as arterial, coronary and venous thrombosis, are usually idiopathic, which makes prediction and prevention difficult. To recognize such hemostatic disorders earlier, the detection of activated platelets is proposed. The detectably labeled annexins compositions are thus disclosed in order to detect activated platelets in hemostatic disorders (U.S. Pat. No. 5,627,036).

Although proposing a wide range of diagnostic uses, none of WO 95/19791; WO 95/34315; WO 96/17618; or WO 98/04294 make reference to imaging the vasculature of solid tumors. Neither does U.S. Pat. No. 5,627,036 make any such suggestions. Nonetheless, the disclosed detectable and radiolabelled annexin compositions per se may now be used to advantage in this regard, in light of the surprising discoveries disclosed herein.

In particular, U.S. Pat. No. 5,627,036 (incorporated herein by reference) discloses annexins detectably labeled with fluorescein isothiocyanate; radioisotopes of halogens, technetium, lead, mercury, thallium or indium; and paramagnetic contrast agents.

WO 95/19791 (incorporated herein by reference) provides conjugates of annexin bonded to an $N_2S_2$ chelate that can be radiolabelled by complexing a radionuclide to the chelate. WO 95/34315 (incorporated herein by reference) provides annexin conjugates comprising one or more galactose residues with the $N_2S_2$ chelate. The galactose moiety is said to facilitate the rapid elimination of the radiolabelled conjugate from the circulation, reducing radiation damage to non-target tissues and background 'noise.'

WO 96/17618 (incorporated herein by reference) in turn provides annexin conjugates suitable for radiolabeling with diagnostic imaging agents that comprise an annexin with a cluster of galactose residues and an $N_2S_2$ chelate. These are reported to have a shorter circulating half-life and a higher binding affinity for target sites than the foregoing radiolabeled annexin-galactose conjugates.

Still further radiolabeled annexin conjugates are provided by WO 98/04294 (incorporated herein by reference). These conjugates comprise an annexin that is modified to provide an accessible sulphydryl group conjugated to a hexose moiety that is recognized by a mammalian liver receptor. Annexin multimer conjugates and chelating compounds conjugated via esterase-sensitive bonds are also provided.

Each of WO 95/19791; WO 95/34315; WO 96/17618; and WO 98/04294; are also specifically incorporated herein by reference for purposes of providing annexin conjugate components for radiolabelling that are amenable to packaging in "cold kits", i.e., wherein the components are provided in separate vials. U.S. Pat. No. 5,627,036 similarly provides kits comprising a carrier being compartmentalized to receive detectably labeled annexins that may be adapted for use herewith.

Although suitable for use in in vitro diagnostics, the present aminophospholipid detection methods are more intended for forming an image of the tumor vasculature of a patient prior to treatment with therapeutic agent-targeting agent constructs. The in vivo diagnostic or imaging methods generally comprise administering to a patient a diagnostically effective amount of an anti-aminophospholipid antibody or binding ligand that is conjugated to a marker that is detectable by non-invasive methods. The antibody- or binding ligand-marker conjugate is allowed sufficient time to localize and bind to the arninophospholipid expressed on the luminal surface of the tumor vasculature. The patient is then exposed to a detection device to identify the detectable marker, thus forming an image of the tumor vasculature.

The nuclear magnetic spin-resonance isotopes, such as gadolinium, are detected using a nuclear magnetic imaging device; and radioactive substances, such as technicium$^{99m}$ or indium$^{111}$, are detected using a gamma scintillation camera or detector. U.S. Pat. No. 5,627,036 is also specifically incorporated herein by reference for purposes of providing even further guidance regarding the safe and effective introduction of such detectably labeled constructs into the blood of an individual, and means for determining the distribution of the detectably labeled annexin extracorporally, e.g., using a gamma scintillation camera or by magnetic resonance measurement.

Dosages for imaging embodiments are generally less than for therapy, but are also dependent upon the age and weight of a patient. A one time dose of between about 0.1, 0.5 or about 1 mg and about 9 or 10 mgs, and more preferably, of between about 1 mg and about 5–10 mgs of anti-aminophospholipid antibody- or aminophospholipid binding ligand-conjugate per patient is contemplated to be useful. U.S. Pat. No. 5,627,036; and WO 95/19791, each incorporated herein by reference, are also instructive regarding doses of detectably-labeled annexins.

J. Combination Therapies

The anti-aminophospholipid antibody treatment methods of the present invention may be combined with any other methods generally employed in the treatment of the particular tumor, disease or disorder that the patient exhibits. So long as a particular therapeutic approach is not known to be detrimental to the patient's condition in itself, and does not significantly counteract the anti-aminophospholipid antibody treatment, its combination with the present invention is contemplated.

In connection solid tumor treatment, the present invention may be used in combination with classical approaches, such as surgery, radiotherapy, chemotherapy, and the like. The invention therefore provides combined therapies in which anti-aminophospholipid antibodies are used simultaneously with, before, or after surgery or radiation treatment; or are administered to patients with, before, or after conventional chemotherapeutic, radiotherapeutic or anti-angiogenic agents, or targeted immunotoxins or coaguligands.

Combination therapy for other vascular diseases is also contemplated. A particular example of such is benign prostatic hyperplasia (BPH), which may be treated with anti-aminophospholipid antibodies in combination other treatments currently practiced in the art. For example, targeting of immunotoxins to markers localized within BPH, such as PSA.

When one or more agents are used in combination with the anti-aminophospholipid antibody therapy, there is no requirement for the combined results to be additive of the effects observed when each treatment is conducted separately. Although at least additive effects are generally desirable, any increased anti-tumor effect above one of the single therapies would be of benefit. Also, there is no particular requirement for the combined treatment to exhibit synergistic effects, although this is certainly possible and advantageous. Agents particularly contemplated for use in achieving potentially synergistic effects are those that injure, or induce apoptosis in, the tumor endothelium, as such injury or apoptosis should amplify the overall therapeutic effect.

To practice combined anti-tumor therapy, one would simply administer to an animal an anti-aminophospholipid antibody in combination with another anti-cancer agent in a manner effective to result in their combined anti-tumor actions within the animal. The agents would therefore be provided in amounts effective and for periods of time effective to result in their combined presence within the tumor vasculature and their combined actions in the tumor environment. To achieve this goal, the anti-aminophospholipid antibodies and anti-cancer agents may be administered to the animal simultaneously, either in a single composition, or as two distinct compositions using different administration routes.

Alternatively, the anti-aminophospholipid antibody treatment may precede, or follow, the anti-cancer agent treatment by, e.g., intervals ranging from minutes to weeks. In certain embodiments where the anti-cancer agent and anti-aminophospholipid antibody are applied separately to the animal, one would ensure that a significant period of time did not expire between the time of each delivery, such that the anti-cancer agent and anti-aminophospholipid antibody composition would still be able to exert an advantageously combined effect on the tumor. In such instances, it is contemplated that one would contact the tumor with both agents within about 5 minutes to about one week of each other and, more preferably, within about 12–72 hours of each other, with a delay time of only about 12–48 hours being most preferred.

Exemplary anti-cancer agents that would be given prior to the anti-aminophospholipid antibody are agents that induce the expression of aminophospholipids within the tumor vasculature. For example, agents that stimulate localized calcium production and/or that induce apoptosis will generally result in increased PS expression, which can then be targeted using a subsequent anti-PS antibody. Anti-aminophospholipid antibodies would be first administered in other situations to cause tumor destruction, followed by anti-angiogenic therapies or therapies directed to targeting necrotic tumor cells.

The general use of combinations of substances in cancer treatment is well know. For example, U.S. Pat. No. 5,710,134 (incorporated herein by reference) discloses components that induce necrosis in tumors in combination with non-toxic substances or "prodrugs". The enzymes set free by necrotic processes cleave the non-toxic "prodrug" into the toxic "drug", which leads to tumor cell death. Also, U.S. Pat. No. 5,747,469 (incorporated herein by reference) discloses the combined use of viral vectors encoding p53 and DNA damaging agents. Any such similar approaches can be used with the present invention.

In some situations, it may even be desirable to extend the time period for treatment significantly, where several days (2, 3, 4, 5, 6 or 7), several weeks (1, 2, 3, 4, 5, 6, 7 or 8) or even several months (1, 2, 3, 4, 5, 6, 7 or 8) lapse between the respective administrations. This would be advantageous in circumstances where one treatment was intended to substantially destroy the tumor, such as the anti-aminophospholipid antibody treatment, and another treatment was intended to prevent micrometastasis or tumor re-growth, such as the administration of an anti-angiogenic agent. The EN 7/44 antibody of Hagemeier et al. (1986) is not believed to be an effective anti-angiogenic agent, lacking binding to a surface accessible antigen, amongst other deficiencies.

It also is envisioned that more than one administration of either the anti-aminophospholipid antibody or the anti-cancer agent will be utilized. The anti-aminophospholipid antibodies and anti-cancer agents may be administered interchangeably, on alternate days or weeks; or a sequence of anti-aminophospholipid antibody treatment may be given, followed by a sequence of anti-cancer agent therapy. In any event, to achieve tumor regression using a combined therapy, all that is required is to deliver both agents in a combined amount effective to exert an anti-tumor effect, irrespective of the times for administration.

In terms of surgery, any surgical intervention may be practiced in combination with the present invention. In connection with radiotherapy, any mechanism for inducing DNA damage locally within tumor cells is contemplated, such as γ-irradiation, X-rays, UV-irradiation, microwaves and even electronic emissions and the like. The directed delivery of radioisotopes to tumor cells is also contemplated, and this may be used in connection with a targeting antibody or other targeting means.

Cytokine therapy also has proven to be an effective partner for combined therapeutic regimens. Various cytokines may be employed in such combined approaches. Examples of cytokines include IL-1α IL-1β, IL-2, IL-3, IL-4, IL-5, IL-6, IL-7, IL-8, IL-9, IL-10, IL11, IL12, IL-13, TGF-β, GM-CSF, M-CSF, G-CSF, TNFα, TNFβ, LAF, TCGF, BCGF, TRF, BAF, BDG, MP, LIF, OSM, TMF, PDGF, IFN-α, IFN-β, IFN-γ. Cytokines are administered according to standard regimens, consistent with clinical indications such as the condition of the patient and relative toxicity of the cytokine. Uteroglobins may also be used to prevent or inhibit metastases (U.S. Pat. No. 5,696,092; incorporated herein by reference).

J1. Chemotherapeutics

In certain embodiments, the anti-aminophospholipid antibodies of the present invention may be administered in combination with a chemotherapeutic agent. Chemotherapeutic drugs can kill proliferating tumor cells, enhancing the necrotic areas created by the overall treatment. The drugs can thus enhance the thrombotic action of the anti-aminophospholipid antibodies.

By inducing the formation of thrombi in tumor vessels, the anti-aminophospholipid antibodies can enhance the action of the chemotherapeutics by retaining or trapping the drugs within the tumor. The chemotherapeutics are thus retained within the tumor, while the rest of the drug is cleared from the body. Tumor cells are thus exposed to a higher concentration of drug for a longer period of time. This entrapment of drug within the tumor makes it possible to reduce the dose of drug, making the treatment safer as well as more effective.

Irrespective of the underlying mechanism(s), a variety of chemotherapeutic agents may be used in the combined treatment methods disclosed herein. Chemotherapeutic agents contemplated as exemplary include, e.g., tamoxifen, taxol, vincristine, vinblastine, etoposide (VP-16), adriamycin, 5-fluorouracil (5FU), camptothecin, actinomycin-D, mitomycin C, cisplatin (CDDP), combretastatin(s) and derivatives and prodrugs thereof As will be understood by those of ordinary skill in the art, the appropriate doses of chemotherapeutic agents will be generally around those already employed in clinical therapies wherein the chemotherapeutics are administered alone or in combination with other chemotherapeutics. By way of example only, agents such as cisplatin, and other DNA alkylating may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Further useful agents include compounds that interfere with DNA replication, mitosis, chromosomal segregation and/or tubulin activity. Such chemotherapeutic compounds include adriamycin, also known as doxorubicin, etoposide, verapamil, podophyllotoxin(s), combretastatin(s) and the like. Widely used in a clinical setting for the treatment of neoplasms, these compounds are administered through bolus injections intravenously at doses ranging from 25–75 mg/m² at 21 day intervals for adriamycin, to 35–50 mg/m² for etoposide intravenously or double the intravenous dose orally.

Agents that disrupt the synthesis and fidelity of polynucleotide precursors may also be used. Particularly useful are agents that have undergone extensive testing and are readily available. As such, agents such as 5-fluorouracil (5-FU) are preferentially used by neoplastic tissue, making this agent particularly usefull for targeting to neoplastic cells. Although quite toxic, 5-FU, is applicable in a wide range of carriers, including topical, however intravenous administration with doses ranging from 3 to 15 mg/kg/day being commonly used.

Exemplary chemotherapeutic agents that are useful in connection with combined therapy are listed in Table B. Each of the agents listed therein are exemplary and by no means limiting. The skilled artisan is directed to "Remington's Pharmaceutical Sciences" 15th Edition, chapter 33, in particular pages 624–652. Some variation in dosage will necessarily occur depending on the condition of the subject being treated. The physician responsible for administration will be able to determine the appropriate dose for the individual subject.

TABLE B

CHEMOTHERAPEUTIC AGENTS USEFUL IN NEOPLASTIC DISEASE

| CLASS | TYPE OF AGENT | NONPROPRIETARY NAMES (OTHER NAMES) | DISEASE |
|---|---|---|---|
| Alkylating Agents | Nitrogen Mustards | Mechlorethamine (HN$_2$) | Hodgkin's disease, non-Hodgkin's lymphomas |
|  |  | Cyclophosphamide Ifosfamide | Acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas |
|  |  | Melphalan (L-sarcolysin) | Multiple myeloma, breast, ovary |
|  |  | Chlorambucil | Chronic lymphacytic leukemia, primary macroglobulinemia, Hodgkin's disease, non-Hodgkin's lymphomas |
|  | Ethylenimenes and Methylmelamines | Hexamethylmelamine | Ovary |
|  |  | Thiotepa | Bladder, breast, ovary |
|  | Alkyl Sulfonates | Busulfan | Chronic granulacytic leukemia |
|  | Nitrasoureas | Carmustine (BCNU) | Hodgkin's disease, non-Hodgkin's lymphomas, primary brain tumors, multiple myeloma, malignant melanoma |
|  |  | Lomustine (CCNU) | Hodgkin's disease, non-Hodgkin's lymphomas, primary brain tumors, small-cell lung |
|  |  | Semustine (methyl-CCNU) | Primary brain tumors, stomach, colon |
|  |  | Streptozocin (streptozotocin) | Malignant pancreatic insulinoma, malignant carcinoid |
|  | Triazines | Dacarbazine (DTIC; dimethyltriazenoimidazolecarboxamide) | Malignant melanoma, Hodgkin's disease, soft-tissue sarcomas |
| Antimetabolites | Folic Acid Analogs | Methotrexate (amethopterin) | Acute lymphocytic leukemia, choriocarcinoma, mycosis fungoides, breast, head and neck, lung, osteogenic sarcoma |
|  | Pyrimidine Analogs | Fluouracil (5-fluorouracil; 5-FU) | Breast, colon, stomach, pancreas, ovary, head and neck, urinary bladder, premalignant skin lesians (topical) |
|  |  | Floxuridine (fluorodeoxyuridine; FUdR) |  |
|  |  | Cytarabine (cytosine arabinoside) | Acute granulocytic and acute lymphocytic leukemias |
|  | Purine Analogs and Related Inhibitors | Mercaptapurine (5-mercaptopurine; 6-MP) | Acute lymphocytic, acute granulocytic and chronic granulocytic leukemias |
|  |  | Thioguanine (6-thioguanine; TG) | Acute granulocytic, acute lymphocytic and chronic granulocytic leukemias |
|  |  | Pentostatin (2-deoxycoformycin) | Hairy cell leukemia, mycosis fungoides, chronic lymphocytic leukemia |
| Natural Products | Vinca Alkaloids | Vinblastine (VLB) | Hodgkin's disease, non-Hodgkin's lymphomas, breast, testis |
|  |  | Vincristine | Acute lymphocytic leukemia, neuroblastoma, Wilms' tumor, rhabdomyosarcoma, Hodgkin's disease, non-Hodgkin's lymphomas, small-cell lung |

TABLE B-continued

CHEMOTHERAPEUTIC AGENTS USEFUL IN NEOPLASTIC DISEASE

| CLASS | TYPE OF AGENT | NONPROPRIETARY NAMES (OTHER NAMES) | DISEASE |
|---|---|---|---|
| | Epipodophyllotoxins | Etoposide<br>Tertiposide | Testis, small-cell lung and other lung, breast, Hodgkin's disease, non-Hodgkin's lymphomas, acute granulocytic leukemia, Kaposi's sarcoma |
| | Antibiotics | Dactinomycin (actinomycin D) | Choriocarcinoma, Wilms' tumor, rhabdomyosarcoma, testis, Kaposi's sarcoma |
| | | Daunorubicin (daunomycin; rubidomycin) | Acute granulocytic and acute lymphocytic leukemias |
| | | Doxorubicin | Soft-tissue, osteogenic and other sarcomas; Hodgkin's disease, non-Hodgkin's lymphomas, acute leukemias, breast, genitourinary, thyroid, lung, stomach, neuroblastoma |
| | | Bleomycin | Testis, head and neck, skin, esophagus, lung and genitourinary tract; Hodgkin's disease, non Hodgkin's lymphomas |
| | | Plicamycin (mithramycin) | Testis, malignant hypercalcemia |
| | | Mitomycin (mitomycin C) | Stomach, cervix, colon, breast, pancreas, bladder, head and neck |
| | Enzymes | L-Asparaginase | Acute lymphocytic leukemia |
| | Biological Response Modifiers | Interferon alfa | Hairy cell leukemia, Kaposi's sarcoma, melanoma, carcinoid, renal cell, ovary, bladder, non-Hodgkin's lymphomas, mycosis fungoides, multiple myeloma, chronic granulocytic leukemia |
| Miscellaneous Agents | Platinum Coordination Complexes | Cisplatin (cis-DDP)<br>Carboplatin | Testis, ovary, bladder, head and neck, lung, thyroid, cervix, endometrium, neuroblastoma, osteogenic sarcoma |
| | Anthracenediane | Mitoxantrane | Acute granulacytic leukemia, breast |
| | Substituted Urea | Hydroxyurea | Chronic granulacytic leukemia, polycythemia vera, essental thrombocytosis, malignant melanoma |
| | Methyl Hydrazine Derivative | Procarbazine (N-methylhydrazine, MIH) | Hodgkin's disease |
| | Adrenocortical Suppressant | Mitatane (o,p'-DDD) | Adrenal cortex |
| | | Aminoglutethimide | Breast |
| Hormones and Antagonists | Adrenocarticosteroids | Prednisone (several other equivalent preparations available) | Acute and chronic lymphocytic leukemias, non-Hodgkin's lymphomas, Hodgkin's disease, breast |
| | Progestins | Hydroxyprogesterone caproate<br>Medroxyprogesterone acetate<br>Megestrol acetate | Endometrium, breast |
| | Estrogens | Diethylstilbestrol<br>Ethinyl estradiol (other preparations available) | Breast, prostate |
| | Antiestrogen | Tamoxifen | Breast |
| | Androgens | Testosterone propionate<br>Fluoxymesterone (other preparations available) | Breast |
| | Antiandrogen | Flutamide | Prostate |
| | Gonadotropin-releasing hormone analog | Leuprolide | Prostate |

J2. Anti-Angiogenics

The term "angiogenesis" refers to the generation of new blood vessels, generally into a tissue or organ. Under normal physiological conditions, humans or animals undergo angiogenesis only in very specific restricted situations. For example, angiogenesis is normally observed in wound healing, fetal and embryonic development and formation of the corpus luteum, endometrium and placenta. Uncontrolled (persistent and/or unregulated) angiogenesis is related to various disease states, and occurs during tumor development and metastasis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

As persistent, unregulated angiogenesis occurs during tumor development and metastasis, the treatment methods of this invention may be used in combination with any one or more "anti-angiogenic" therapies. Exemplary anti-angiogenic agents that are useful in connection with combined therapy are listed in Table C. Each of the agents listed therein is exemplary and by no means limiting.

The amino acid sequence of angiostatin varies slightly between species. For example, in human angiostatin, the amino acid sequence is substantially similar to the sequence of the above described murine plasminogen fragment, although an active human angiostatin sequence may start at either amino acid number 97 or 99 of an intact human plasminogen amino acid sequence. Further, human plasminogen may be used, as it has similar anti-angiogenic activity, as shown in a mouse tumor model.

Certain anti-angiogenic therapies have already been shown to cause tumor regressions, and angiostatin is one such agent. Endostatin, a 20 kDa COOH-terminal fragment

TABLE C

Inhibitors and Negative Regulators of Angiogenesis

| Substances | References |
| --- | --- |
| Angiostatin | O'Reilly et al., 1994 |
| Endostatin | O'Reilly et al., 1997 |
| 16kDa prolactin fragment | Ferrara et al., 1991; Clapp et al., 1993; D'Angelo et al., 1995; Lee et al., 1998 |
| Laminin peptides | Kleinman et al., 1993; Yamamura et al., 1993; Iwamoto et al., 1996; Tryggvason, 1993 |
| Fibronectin peptides | Grant et al., 1998; Sheu et al., 1997 |
| Tissue metalloproteinase inhibitors (TIMP 1, 2, 3, 4) | Sang, 1998 |
| Plasminogen activator inhibitors (PAI-1, -2) | Soff et al., 1995 |
| Tumor necrosis factor α (high dose, in vitro) | Frater-Schroder et al., 1987 |
| TGF-β1 | RayChadhury and D'Amore, 1991; Tada et al., 1994 |
| Interferons (IFN-α, -β, γ) | Moore et al., 1998; Lingen et al., 1998 |
| ELR- CXC Chemokines: IL-12; SDF-1; MIG; Platelet factor 4 (PF-4); IP-10 | Moore et al., 1998; Hiscox and Jiang, 1997; Coughlin et al., 1998; Tanaka et al., 1997 |
| Thrombospondin (TSP) | Good et al., 1990; Frazier, 1991; Bornstein, 1992; Tolsma et al., 1993; Sheibani and Frazier, 1995; Volpert et al., 1998 |
| SPARC | Hasselaar and Sage, 1992; Lane et al., 1992; Jendraschak and Sage, 1996 |
| 2-Methoxyoestradiol | Fotsis et al., 1994 |
| Proliferin-related protein | Jackson et al., 1994 |
| Suramin | Gagliardi et al., 1992; Takano et al., 1994; Waltenberger et al., 1996; Gagliardi et al., 1998; Manetti et al., 1998 |
| Thalidomide | D'Amato et al., 1994; Kenyon et al., 1997 Wells, 1998 |
| Cortisone | Thorpe et al., 1993 Folkman et al., 1983 Sakamoto et al., 1986 |
| Linomide | Vukanovic et al., 1993; Ziche et al., 1998; Nagler et al., 1998 |
| Fumagillin (AGM-1470; TNP-470) | Sipos et al., 1994; Yoshida et al., 1998 |
| Tamoxifen | Gagliardi and Collins, 1993; Linder and Borden, 1997; Haran et al., 1994 |
| Korean mistletoe extract (*Viscum album coloratum*) | Yoon et al., 1995 |
| Retinoids | Oikawa et al., 1989; Lingen et al., 1996; Majewski et al. 1996 |
| CM101 | Hellerqvist et al., 1993; Quinn et al., 1995; Wamil et al., 1997; DeVore et al., 1997 |
| Dexamethasone | Hori et al., 1996; Wolff et al., 1997 |
| Leukemia inhibitory factor (LIF) | Pepper et al., 1995 |

A certain preferred component for use in inhibiting angiogenesis is a protein named "angiostatin". This component is disclosed in U.S. Pat. Nos. 5,776,704; 5,639,725 and 5,733,876, each incorporated herein by reference. Angiostatin is a protein having a molecular weight of between about 38 kD and about 45 kD, as determined by reducing polyacrylamide gel electrophoresis, which contains approximately Kringle regions 1 through 4 of a plasminogen molecule. Angiostatin generally has an amino acid sequence substantially similar to that of a fragment of murine plasminogen beginning at amino acid number 98 of an intact murine plasminogen molecule.

of collagen XVIII, the bacterial polysaccharide CM101, and the antibody LM609 also have angiostatic activity. However, in light of their other properties, they are referred to as anti-vascular therapies or tumor vessel toxins, as they not only inhibit angiogenesis but also initiate the destruction of tumor vessels through mostly undefined mechanisms. Their combination with the present invention is clearly envisioned.

Angiostatin and endostatin have become the focus of intense study, as they are the first angiogenesis inhibitors that have demonstrated the ability to not only inhibit tumor growth but also cause tumor regressions in mice. There are multiple proteases that have been shown to produce angiostatin from plasminogen including elastase, macrophage metalloelastase (MME), matrilysin (MMP-7), and 92 kDa gelatinase B/type IV collagenase (MMP-9).

MME can produce angiostatin from plasminogen in tumors and granulocyte-macrophage colony-stimulating factor (GMCSF) upregulates the expression of MME by macrophages inducing the production of angiostatin. The role of MME in angiostatin generation is supported by the finding that MME is in fact expressed in clinical samples of hepatocellular carcinomas from patients. Another protease thought to be capable of producing angiostatin is stromelysin-1 (MMP-3). MMP-3 has been shown to produce angiostatin-like fragments from plasminogen in vitro.

The mechanism of action for angiostatin is currently unclear, it is hypothesized that it binds to an unidentified cell surface receptor on endothelial cells inducing endothelial cell to undergo programmed cell death or mitotic arrest. Endostatin appears to be an even more powerful anti-angiogenesis and anti-tumor agent although its biology is much less clear. Endostatin is effective at causing regressions in a number of tumor models in mice. Tumors do not develop resistance to endostatin and, after multiple cycles of treatment, tumors enter a dormant state during which they do not increase in volume. In this dormant state, the percentage of tumor cells undergoing apoptosis was increased, yielding a population that essentially stays the same size. Endostatin is also thought to bind an unidentified endothelial cell surface receptor that mediates its effect.

CM101 is a bacterial polysaccharide that has been well characterized in its ability to induce neovascular inflammation in tumors. CM101 binds to and cross-links receptors expressed on dedifferentiated endothelium that stimulates the activation of the complement system. It also initiates a cytokine-driven inflammatory response that selectively targets the tumor. It is a uniquely antipathoangiogenic agent that downregulates the expression VEGF and its receptors. CM101 is currently in clinical trials as an anti-cancer drug, and can be used in combination herewith.

Thrombospondin (TSP-1) and platelet factor 4 (PF4) may also be used in combination with the present invention. These are both angiogenesis inhibitors that associate with heparin and are found in platelet α-granules. TSP-1 is a large 450 kDa multi-domain glycoprotein that is constituent of the extracellular matrix. TSP-1 binds to many of the proteoglycan molecules found in the extracellular matrix including, HSPGs, fibronectin, laminin, and different types of collagen. TSP-1 inhibits endothelial cell migration and proliferation in vitro and angiogenesis in vivo. TSP-1 can also suppress the malignant phenotype and tumorigenesis of transformed endothelial cells. The tumor suppressor gene p53 has been shown to directly regulate the expression of TSP-1 such that, loss of p53 activity causes a dramatic reduction in TSP-1 production and a concomitant increase in tumor initiated angiogenesis.

PF4 is a 70aa protein that is member of the CXC ELR-family of chemokines that is able to potently inhibit endothelial cell proliferation in vitro and angiogenesis in vivo. PF4 administered intratumorally or delivered by an adenoviral vector is able to cause an inhibition of tumor growth.

Interferons and metalloproteinase inhibitors are two other classes of naturally occurring angiogenic inhibitors that can be combined with the present invention. The anti-endothelial activity of the interferons has been known since the early 1980s, however, the mechanism of inhibition is still unclear. It is known that they can inhibit endothelial cell migration and that they do have some anti-angiogenic activity in vivo that is possibly mediated by an ability to inhibit the production of angiogenic promoters by tumor cells. Vascular tumors in particular are sensitive to interferon, for example, proliferating hemangiomas can be successfully treated with IFNα.

Tissue inhibitors of metalloproteinases (TIMPs) are a family of naturally occurring inhibitors of matrix metalloproteases (MMPs) that can also inhibit angiogenesis and can be used in combined treatment protocols with the present invention. MMPs play a key role in the angiogenic process as they degrade the matrix through which endothelial cells and fibroblasts migrate when extending or remodeling the vascular network. In fact, one member of the MMPs, MMP-2, has been shown to associate with activated endothelium through the integrin αvβ3 presumably for this purpose. If this interaction is disrupted by a fragment of MMP-2, then angiogenesis is downregulated and in tumors growth is inhibited.

There are a number of pharmacological agents that inhibit angiogenesis, any one or more of which may be used in combination with the present invention. These include AGM-1470/TNP-470, thalidomide, and carboxyamidotriazole (CAI). Fumagillin was found to be a potent inhibitor of angiogenesis in 1990, and since then the synthetic analogues of fumagillin, AGM-1470 and TNP-470 have been developed. Both of these drugs inhibit endothelial cell proliferation in vitro and angiogenesis in vivo. TNP-470 has been studied extensively in human clinical trials with data suggesting that long-term administration is optimal.

Thalidomide was originally used as a sedative but was found to be a potent teratogen and was discontinued. In 1994 it was found that thalidomide is an angiogenesis inhibitor. Thalidomide is currently in clinical trials as an anti-cancer agent as well as a treatment of vascular eye diseases.

CAI is a small molecular weight synthetic inhibitor of angiogenesis that acts as a calcium channel blocker that prevents actin reorganization, endothelial cell migration and spreading on collagen IV. CAI inhibits neovascularization at physiological attainable concentrations and is well tolerated orally by cancer patients. Clinical trials with CAI have yielded disease stabilization in 49% of cancer patients having progressive disease before treatment.

Cortisone in the presence of heparin or heparin fragments was shown to inhibit tumor growth in mice by blocking endothelial cell proliferation. The mechanism involved in the additive inhibitory effect of the steroid and heparin is unclear although it is thought that the heparin may increase the uptake of the steroid by endothelial cells. The mixture has been shown to increase the dissolution of the basement membrane underneath newly formed capillaries and this is also a possible explanation for the additive angiostatic effect. Heparin-cortisol conjugates also have potent angiostatic and anti-tumor effects activity in vivo.

Further specific angiogenesis inhibitors, including, but not limited to, Anti-Invasive Factor, retinoic acids and paclitaxel (U.S. Pat. No. 5,716,981; incorporated herein by reference); AGM-1470 (Ingber et al., 1990; incorporated herein by reference); shark cartilage extract (U.S. Pat. No. 5,618,925; incorporated herein by reference); anionic polyamide or polyurea oligomers (U.S. Pat. No. 5,593,664; incorporated herein by reference); oxindole derivatives (U.S. Pat. No. 5,576,330; incorporated herein by reference); estradiol derivatives (U.S. Pat. No. 5,504,074; incorporated herein by reference); and thiazolopyrimidine derivatives (U.S. Pat. No. 5,599,813; incorporated herein by reference) are also contemplated for use as anti-angiogenic compositions for the combined uses of the present invention.

Compositions comprising an antagonist of an $\alpha_v\beta_3$ integrin may also be used to inhibit angiogenesis in combination with the present invention. As disclosed in U.S. Pat. No. 5,766,591 (incorporated herein by reference), RGD-containing polypeptides and salts thereof, including cyclic polypeptides, are suitable examples of $\alpha_v\beta_3$ integrin antagonists.

The antibody LM609 against the $\alpha_v\beta_3$ integrin also induces tumor regressions. Integrin $\alpha_v\beta_3$ antagonists, such as LM609, induce apoptosis of angiogenic endothelial cells leaving the quiescent blood vessels unaffected. LM609 or other $\alpha_v\beta_3$ antagonists may also work by inhibiting the interaction of $\alpha_v\beta_3$ and MMP-2, a proteolytic enzyme thought to play an important role in migration of endothelial cells and fibroblasts.

Apoptosis of the angiogenic endothelium in this case may have a cascade effect on the rest of the vascular network. Inhibiting the tumor vascular network from completely responding to the tumor's signal to expand may, in fact, initiate the partial or full collapse of the network resulting in tumor cell death and loss of tumor volume. It is possible that endostatin and angiostatin function in a similar fashion. The fact that LM609 does not affect quiescent vessels but is able to cause tumor regressions suggests strongly that not all blood vessels in a tumor need to be targeted for treatment in order to obtain an anti-tumor effect.

Targeted or non-targeted angiopoietins, preferably angiopoietin-2, may also be used in combination with the present invention (see discussion below for targeted angiopoietins). Angiopoietin-2 (SEQ ID NO:3 and SEQ ID NO:4) is a ligand for Tie2 and generally counteracts blood vessel maturation/stability mediated by angiopoietin-1. It is thus an antagonist of angiopoietin-1, and acts to disturb capillary structure. In the absence of another angiogenic signal (such as VEGF), angiopoietin-2 causes vessels to destabilize and become immature (Holash et al., 1999; incorporated herein by reference). Provision of targeted or non-targeted angiopoietin-2 in connection with the methods of the present invention is thus contemplated, particularly in tumors with low VEGF levels and/or in combination with VEGF inhibition. Manipulation of angiopoietin-1 and two new angiopoietins, angiopoietin-3 (mouse) and angiopoietin-4 (human), could also be used in conjunction with this invention.

Other methods of therapeutic intervention based upon altering signaling through the Tie2 receptor can also be used in combination with the present invention, such as using a soluble Tie2 receptor capable of blocking Tie2 activation (Lin et al., 1998). Delivery of such a construct using recombinant adenoviral gene therapy has been shown to be effective in treating cancer and reducing metastases (Lin et al., 1998).

J3. Apoptosis-Inducing Agents

Therapeutic agent-targeting agent treatment may also be combined with treatment methods that induce apoptosis in any cells within the tumor, including tumor cells and tumor vascular endothelial cells. Although many anti-cancer agents may have, as part of their mechanism of action, an apoptosis-inducing effect, certain agents have been discovered, designed or selected with this as a primary mechanism, as described below.

A number of oncogenes have been described that inhibit apoptosis, or programmed cell death. Exemplary oncogenes in this category include, but are not limited to, bcr-abl, bcl-2 (distinct from bcl-1, cyclin D1; GenBank accession numbers M14745, X06487; U.S. Pat. Nos. 5,650,491; and 5,539,094; each incorporated herein by reference) and family members including Bcl-xl, Mcl-1, Bak, A1, A20. Overexpression of bcl-2 was first discovered in T cell lymphomas. bcl-2 functions as an oncogene by binding and inactivating Bax, a protein in the apoptotic pathway. Inhibition of bcl-2 function prevents inactivation of Bax, and allows the apoptotic pathway to proceed. Thus, inhibition of this class of oncogenes, e.g., using antisense nucleotide sequences, is contemplated for use in the present invention in aspects wherein enhancement of apoptosis is desired (U.S. Pat. Nos. 5,650,491; 5,539,094; and 5,583,034; each incorporated herein by reference).

Many forms of cancer have reports of mutations in tumor suppressor genes, such as p53. Inactivation of p53 results in a failure to promote apoptosis. With this failure, cancer cells progress in tumorigenesis, rather than become destined for cell death. Thus, provision of tumor suppressors is also contemplated for use in the present invention to stimulate cell death. Exemplary tumor suppressors include, but are not limited to, p53, Retinoblastoma gene (Rb), Wilm's tumor (WT1), bax alpha, interleukin-1b-converting enzyme and family, MEN-1 gene, neurofibromatosis, type 1 (NF1), cdk inhibitor p16, colorectal cancer gene (DCC), familial adenomatosis polyposis gene (FAP), multiple tumor suppressor gene (MTS-1), BRCA1 and BRCA2.

Preferred for use are the p53 (U.S. Pat. Nos. 5,747,469; 5,677,178; and 5,756,455; each incorporated herein by reference), Retinoblastoma, BRCA1 (U.S. Pat. Nos. 5,750,400; 5,654,155; 5,710,001; 5,756,294; 5,709,999; 5,693,473; 5,753,441; 5,622,829; and 5,747,282; each incorporated herein by reference), MEN-1 (GenBank accession number U93236) and adenovirus E1A (U.S. Pat. No. 5,776,743; incorporated herein by reference) genes.

Other compositions that may be used include genes encoding the tumor necrosis factor related apoptosis inducing ligand termed TRAIL, and the TRAIL polypeptide (U.S. Pat. No. 5,763,223; incorporated herein by reference); the 24 kD apoptosis-associated protease of U.S. Pat. No. 5,605,826 (incorporated herein by reference); Fas-associated factor 1, FAF1 (U.S. Pat. No. 5,750,653; incorporated herein by reference). Also contemplated for use in these aspects of the present invention is the provision of interleukin-1β-converting enzyme and family members, which are also reported to stimulate apoptosis.

Compounds such as carbostyril derivatives (U.S. Pat. Nos. 5,672,603; and 5,464,833; each incorporated herein by reference); branched apogenic peptides (U.S. Pat. No. 5,591,717; incorporated herein by reference); phosphotyrosine inhibitors and non-hydrolyzable phosphotyrosine analogs (U.S. Pat. Nos. 5,565,491; and 5,693,627; each incorporated herein by reference); agonists of RXR retinoid receptors (U.S. Pat. No. 5,399,586; incorporated herein by reference); and even antioxidants (U.S. Pat. No. 5,571,523; incorporated herein by reference) may also be used. Tyrosine kinase inhibitors, such as genistein, may also be linked to ligands that target a cell surface receptor (U.S. Pat. No. 5,587,459; incorporated herein by reference).

J4. Immunotoxins and Coaguligands

The naked anti-aminophospholipid antibody treatment methods of the invention may be used in combination with immunotoxins (ITs) and/or coaguligands in which the targeting portion thereof, e.g., antibody or ligand, is directed to a relatively specific marker of the tumor cells, tumor vasculature or tumor stroma. In common with the chemotherapeutic and anti-angiogenic agents discussed above, the use of an anti-aminophospholipid antibody in combination with a targeted toxin or coagulant will generally result in the distinct agents being directed against different targets within the tumor environment. This should result in additive, markedly greater than additive or even synergistic anti-tumor results.

Generally speaking, antibodies or ligands for use in these additional aspects of the invention will preferably recognize accessible tumor antigens that are preferentially, or specifically, expressed in the tumor site. The antibodies or ligands will also preferably exhibit properties of high affinity; and the antibodies, ligands or conjugates thereof, will not exert significant in vivo side effects against life-sustaining normal tissues, such as one or more tissues selected from heart, kidney, brain, liver, bone marrow, colon, breast, prostate, thyroid, gall bladder, lung, adrenals, muscle, nerve fibers, pancreas, skin, or other life-sustaining organ or tissue in the human body. The term "significant side effects", as used herein, refers to an antibody, ligand or antibody conjugate, that, when administered in vivo, will produce only negligible or clinically manageable side effects, such as those normally encountered during chemotherapy.

At least one binding region of these second anti-cancer agents employed in combination with the anti-aminophospholipid antibodies of the invention will be a component that is capable of delivering a toxin or coagulation factor to the tumor region, i.e., capable of localizing within a tumor site. Such targeting agents may be directed against a component of a tumor cell, tumor vasculature or tumor stroma. The targeting agents will generally bind to a surface-expressed, surface-accessible or surface-localized component of a tumor cell, tumor vasculature or tumor stroma. However, once tumor vasculature and tumor cell destruction begins, internal components will be released, allowing additional targeting of virtually any tumor component.

Many tumor cell antigens have been described, any one which could be employed as a target in connection with the combined aspects of the present invention. Appropriate tumor cell antigens for additional immunotoxin and coaguligand targeting include those recognized by the antibodies B3 (U.S. Pat. No. 5,242,813; incorporated herein by reference; ATCC HB 10573); KSI/4 (U.S. Pat. No. 4,975,369; incorporated herein by reference; obtained from a cell comprising the vectors NRRL B-18356 and/or NRRL B-18357); 260F9 (ATCC HB 8488); and D612 (U.S. Pat. No. 5,183,756; incorporated herein by reference; ATCC HB 9796). One may also consult the ATCC Catalogue of any subsequent year to identify other appropriate cell lines producing anti-tumor cell antibodies.

For tumor vasculature targeting, the targeting antibody or ligand will often bind to a marker expressed by, adsorbed to, induced on or otherwise localized to the intratumoral blood vessels of a vascularized tumor. Appropriate expressed target molecules include, for example, endoglin, E-selectin, P-selectin, VCAM-1, ICAM-1, PSMA (Liu et al., 1997), a TIE, a ligand reactive with LAM-1, a VEGF/VPF receptor, an FGF receptor, $\alpha_v\beta_3$ integrin, pleiotropin and endosialin. Suitable adsorbed targets are those such as VEGF, FGF, TGFβ, HGF, PF4, PDGF, TIMP, a ligand that binds to a TIE and tumor-associated fibronectin isoforns. Antigens naturally and artificially inducible by cytokines and coagulants may also be targeted, such as ELAM-1, VCAM-1, ICAM-1, a ligand reactive with LAM-1, endoglin, and even MHC Class II (cytokine-inducible, e.g., by IL-1, TNF-α, IFN-γ, IL4 and/or TNF-β); and E-selectin, P-selectin, PDGF and ICAM-1 (coagulant-inducible e.g., by thrombin, Factor IX/IXa, Factor X/Xa and/or plasmin).

The following patents and patent applications are specifically incorporated herein by reference for the purposes of even further supplementing the present teachings regarding the preparation and use of immunotoxins directed against expressed, adsorbed, induced or localized markers of tumor vasculature: U.S. Pat. Nos. 5,855,866; 5,776,427; 5,863,538; 5,660,827; 5,855,866 and 5,877,289; and 6,004,554; 5,965,132; 6,051,230; 6,004,555; 6,036,955; and 6,093,399 and U.S. application Ser. No. 07/846,349.

Suitable tumor stromal targets include components of the tumor extracellular matrix or stroma, or components those bound therein; including basement membrane markers, type IV collagen, laminin, heparan sulfate, proteoglycan, fibronectins, activated platelets, LIBS and tenascin. A preferred target for such uses is RIBS.

The following patents and patent applications are specifically incorporated herein by reference for the purposes of even further supplementing the present teachings regarding the preparation and use of tumor stromal targeting agents: U.S. Pat. Nos. 5,877,289 and 6,004,555; 6,036,955 and 6,093,399.

In certain applications, the second anti-cancer therapeutics will be antibodies or ligands operatively attached to cytotoxic or otherwise anti-cellular agents having the ability to kill or suppress the growth or cell division of endothelial cells. Suitable anti-cellular agents include chemotherapeutic agents and radioisotopes, as well as cytotoxins. Exemplary chemotherapeutic agents include: steroids; cytokines; anti-metabolites, such as cytosine arabinoside, fluorouracil, methotrexate or aminopterin; anthracyclines; mitomycin C; vinca alkaloids; antibiotics; demecolcine; etoposide; mithramycin; and anti-tumor alkylating agents, such as chlorambucil or melphalan.

In most combined therapeutic applications, toxin moieties will be preferred, due to the much greater ability of most toxins to deliver a cell killing effect, as compared to other potential agents. Therefore, preferred anti-cellular agents for second therapeutics are plant-, fungus- or bacteria-derived toxins. Exemplary toxins include epipodophyllotoxins; bacterial endotoxin or the lipid A moiety of bacterial endotoxin; ribosome inactivating proteins, such as saporin or gelonin; α-sarcin; aspergillin; restrictocin; ribonucleases, such as placental ribonuclease; diphtheria toxin and pseudomonas exotoxin.

Certain preferred toxins are gelonin and the A chain toxins, such as ricin A chain. The most preferred toxin moiety is often ricin A chain that has been treated to modify or remove carbohydrate residues, so called "deglycosylated A chain" (dgA). Deglycosylated ricin A chain is preferred because of its extreme potency, longer half-life, and because it is economically feasible to manufacture it a clinical grade and scale. Recombinant and/or truncated ricin A chain may also be used.

Other agents for use with immunoconjugates for targeting tumor vasculature or tumor stroma are the angiopoietins. The angiopoietins, like the members of the VEGF family, are growth factors largely specific for vascular endothelium (Davis and Yancopoulos, 1999; Holash et al., 1999; incorporated herein by reference). The angiopoietins first described were a naturally occurring agonist, angiopoietin-1 (Ang-1; SEQ ID NO:1 and SEQ ID NO:2), and a naturally occurring antagonist, angiopoietin-2 (Ang-2; SEQ ID NO:3 and SEQ ID NO:4), both of which act by means of the endothelial cell tyrosine kinase receptor, Tie2.

Two new angiopoietins, angiopoietin-3 (mouse) and angiopoietin-4 (human) have also been identified (Valenzuela et al., 1999). Angiopoietin-3 appears to act as an antagonist, whereas angiopoietin-4 appears to function as an agonist (Valenzuela et al., 1999). A protein termed angiopoietin-3 was also cloned from human heart and reported not to have mitogenic effects on endothelial cells (Kim et al., 1999). Fusion proteins of angiopoietin-1 and angiopoietin-2 have also been created, as exemplified by the stable Ang-1-Ang-2 fusion protein included herein as SEQ ID NO:5.

Whereas VEGF is necessary for the early stages of vascular development, angiopoietin-1 is generally required for the later stages of vascular remodeling. Angiopoietin-1 is thus a maturation or stabilization factor, which converts immature vessels to mature vessels.

Angiopoietin-1 has been shown to augment revascularization in ischemic tissue (Shyu et al., 1998) and to increase the survival of vascular networks exposed to either VEGF or a form of aFGF (Papapetropoulos et al., 1999). These authors also showed that angiopoietin-1 prevents apoptotic death in HUVEC triggered by withdrawal of the same form of aFGF (Papapetropoulos et al., 1999). Such data are consistent with the direct role of angiopoietin-1 on human endothelial cells and its interaction with other angiogenic molecules to stabilize vascular structures by promoting the survival of differentiated endothelial cells.

Angiopoietin-2 is a preferred agent for use in targeted combination therapy, particularly in tumors with low VEGF levels and/or in combination with VEGF inhibition. Angiopoietin-2 is also a ligand for Tie2, but generally counteracts blood vessel maturation/stability mediated by angiopoietin-1. It is thus an antagonist of angiopoietin-1, and acts to disturb capillary structure. However, as angiopoietin-2 renders endothelial cells responsive to angiogenic stimuli, it can initiate neovascularization in combination with other appropriate signals, particularly VEGF (Asahara et al., 1998; Holash et al., 1999; incorporated herein by reference).

In the absence of another angiogenic signal, angiopoietin-2 causes vessels to destabilize and become immature. In the presence of a stimulus, such as VEGF, angiopoietin-2 promotes angiogenesis. Indeed, the angiogenic effects of a number of regulators are believed to be achieved, at least in part, through the regulation of an autocrine loop of angiopoietin-2 activity in microvascular endothelial cells (Mandriota and Pepper, 1998).

Angiopoietin-2 expression in tumor tissue has been reported (Tanaka et al., 1999), where it presumably acts in combination with VEGF to promote angiogenesis (Stratmann et al., 1998; Holash et al., 1999). However, as angiopoietin-2 provides a negative signal when VEGF is low or absent, provision of angiopoietin-2 can be a useful therapeutic approach. Angiopoietin-2 can be administered as a protein therapeutic or via gene therapy (see above), or in a tumor-targeted form. Although all types of targeted angiopoietin-2 constructs are envisioned for use in the combined therapy aspects of the invention, currently preferred agents for targeting angiopoietin-2 to the tumor are those that bind to aminophospholipids, including anti-PS antibodies and annexins.

For tumor targeting and treatment with immunotoxins, the following patents and patent applications are specifically incorporated herein by reference for the purposes of even further supplementing the present teachings regarding anti-cellular and cytotoxic agents: U.S. Pat. Nos. 5,855,866; 5,776,427; 5,863,538; and 5,660,827; and 6,004,554; 5,965,132 and 6,051,230; and U.S. application Ser. No. 07/846,349.

The second, targeted agent for optional use with the anti-aminophospholipid antibodies of the invention may also comprise a targeted component that is capable of promoting coagulation, i.e., a "coaguligand". Here, the targeting antibody or ligand may be directly or indirectly, e.g., via another antibody, linked to a factor that directly or indirectly stimulates coagulation.

Preferred coagulation factors for such uses are Tissue Factor (TF) and TF derivatives, such as truncated TF (tTF), dimeric and multimeric TF, and mutant TF deficient in the ability to activate Factor VII. Other suitable coagulation factors include vitamin K-dependent coagulants, such as Factor II/IIa, Factor VII/VIIa, Factor IX/IXa and Factor X/Xa; vitamin K-dependent coagulation factors that lack the Gla modification; Russell's viper venom Factor X activator; platelet-activating compounds, such as thromboxane $A_2$ and thromboxane $A_2$ synthase; and inhibitors of fibrinolysis, such as α2-antiplasmin.

Tumor targeting and treatment with coaguligands is described in the following patents and patent applications, each of which are specifically incorporated herein by reference for the purposes of even further supplementing the present teachings regarding coaguligands and coagulation factors: U.S. Pat. Nos. 5,855,866 and 5,877,289; 5,965,132; 6,004,554; 6,036,955; and 6,093,399 and U.S. application Ser. No. 07/846,349.

As somewhat wider distribution of a coagulating agent will not be associated with severe side effects, there is a less stringent requirement imposed on the targeting element of coaguligands than with immunotoxins. Therefore, to achieve specific targeting means that coagulation is promoted in the tumor vasculature relative to the vasculature in non-tumor sites. Thus, specific targeting of a coaguligand is a functional term, rather than a purely physical term relating to the biodistribution properties of the targeting agent. It is not unlikely that useful targets may be not be entirely tumor-restricted, and that targeting ligands that are effective to promote tumor-specific coagulation may nevertheless be safely found at other sites of the body following administration, as occurs with VCAM-1.

The preparation of immunotoxins is generally well known in the art (see, e.g., U.S. Pat. No. 4,340,535, incorporated herein by reference). Each of the following patents and patent applications are further incorporated herein by reference for the purposes of even further supplementing the present teachings regarding immunotoxin generation, purification and use: U.S. Pat. Nos. 5,855,866; 5,776,427; 5,863, 538; and 5,660,827; 6,004,554; 5,965,132; and 6,051,230; and U.S. application Ser. No. 07/846,349.

In the preparation of immunotoxins, advantages may be achieved through the use of certain linkers. For example, linkers that contain a disulfide bond that is sterically "hindered" are often preferred, due to their greater stability in vivo, thus preventing release of the toxin moiety prior to binding at the site of action. It is generally desired to have a conjugate that will remain intact under conditions found everywhere in the body except the intended site of action, at which point it is desirable that the conjugate have good "release" characteristics.

Depending on the specific toxin compound used, it may be necessary to provide a peptide spacer operatively attaching the targeting agent and the toxin compound, wherein the peptide spacer is capable of folding into a disulfide-bonded loop structure. Proteolytic cleavage within the loop would then yield a heterodimeric polypeptide wherein the targeting agent and the toxin compound are linked by only a single disulfide bond.

When certain other toxin compounds are utilized, a non-cleavable peptide spacer may be provided to operatively attach the targeting agent and the toxin compound. Toxins that may be used in conjunction with non-cleavable peptide spacers are those that may, themselves, be converted by proteolytic cleavage, into a cytotoxic disulfide-bonded form. An example of such a toxin compound is a Pseudonomas exotoxin compound.

A variety of chemotherapeutic and other pharmacological agents can also be successfully conjugated to antibodies or targeting ligands. Exemplary antineoplastic agents that have been conjugated to antibodies include doxorubicin, daunomycin, methotrexate and vinblastine. Moreover, the attachment of other agents such as neocarzinostatin, macromycin, trenimon and α-amanitin has been described (see U.S. Pat. Nos. 5,855,866; and 5,965,132 and references incorporated therein.

In light of one of the present inventors earlier work, the preparation of coaguligands is now also easily practiced. The operable association of one or more coagulation factors with a targeting agent may be a direct linkage, such as those described above for the immunotoxins. Alternatively, the operative association may be an indirect attachment, such as where the targeting agent is operatively attached to a second binding region, preferably and antibody or antigen binding region of an antibody, that binds to the coagulation factor. The coagulation factor should be attached to the targeting agent at a site distinct from its functional coagulating site, particularly where a covalent linkage is used to join the molecules.

Indirectly linked coaguligands are most often based upon bispecific antibodies. The preparation of bispecific antibodies is also well known in the art. One preparative method involves the separate preparation of antibodies having specificity for the targeted tumor component, on the one hand, and the coagulating agent on the other. Peptic F(ab'γ)$_2$ fragments from the two chosen antibodies are then generated, followed by reduction of each to provide separate Fab'γSH fragments. The SH groups on one of the two partners to be coupled are then alkylated with a cross-linking reagent, such as o-phenylenedimaleimide, to provide free maleimide groups on one partner. This partner may then be conjugated to the other by means of a thioether linkage, to give the desired F(ab'γ)$_2$ heteroconjugate (Glennie et al., 1987; incorporated herein by reference). Other approaches, such as cross-linking with SPDP or protein A may also be carried out.

Another method for producing bispecific antibodies is by the fusion of two hybridomas to form a quadroma. As used herein, the term "quadroma" is used to describe the productive fusion of two B cell hybridomas. Using now standard techniques, two antibody producing hybridomas are fused to give daughter cells, and those cells that have maintained the expression of both sets of clonotype immunoglobulin genes are then selected.

A preferred method of generating a quadroma involves the selection of an enzyme deficient mutant of at least one of the parental hybridomas. This first mutant hybridoma cell line is then fused to cells of a second hybridoma that had been lethally exposed, e.g., to iodoacetamide, precluding its continued survival. Cell fusion allows for the rescue of the first hybridoma by acquiring the gene for its enzyme deficiency from the lethally treated hybridoma, and the rescue of the second hybridoma through fusion to the first hybridoma. Preferred, but not required, is the fusion of immunoglobulins of the same isotype, but of a different subclass. A mixed subclass antibody permits the use if an alternative assay for the isolation of a preferred quadroma.

Microtiter identification embodiments, FACS, immunofluorescence staining, idiotype specific antibodies, antigen binding competition assays, and other methods common in the art of antibody characterization may be used to identify preferred quadromas. Following the isolation of the quadroma, the bispecific antibodies are purified away from other cell products. This may be accomplished by a variety of antibody isolation procedures, known to those skilled in the art of immunoglobulin purification (see, e.g., Antibodies: A Laboratory Manual, 1988; incorporated herein by reference). Protein A or protein G sepharose columns are preferred.

In the preparation of both immunotoxins and coaguligands, recombinant expression may be employed. The nucleic acid sequences encoding the chosen targeting agent, and toxin or coagulant, are attached in-frame in an expression vector. Recombinant expression thus results in translation of the nucleic acid to yield the desired targeting agent-toxin/coagulant compound.

The following patents and patent applications are each incorporated herein by reference for the purposes of even further supplementing the present teachings regarding coaguligand preparation, purification and use, including bispecific antibody coaguligands: U.S. Pat. Nos. 5,855,866 and 5,877,289; 5,965,132; 6,004,555; 6,036,955; and 6,093,399 and U.S. applications Ser. Nos. 07/846,349; 08/273,567; 08/485,482; and 08/472,631.

Effective doses of immunotoxins and coaguligands for combined use with the naked anti-aminophospholipid antibodies in the treatment of cancer will be between about 0.1 mg/kg and about 2 mg/kg, and preferably, of between about 0.8 mg/kg and about 1.2 mg/kg, when administered via the IV route at a frequency of about 1 time per week. Some variation in dosage will necessarily occur depending on the condition of the subject being treated. The physician responsible for administration will determine the appropriate dose for the individual subject.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

VCAM-1 Expression on Tumor and Normal Blood Vessels

A. Materials and Methods

1. Materials

Na$^{125}$I was obtained from Amersham (Arlington Heights, Ill.). Dulbecco's modified Eagle's tissue culture medium (DMEM) and Dulbecco PBS containing Ca$^{2+}$ and Mg$^{2+}$ were obtained from Gibco (Grand Island, N.Y.). Fetal calf serum was obtained from Hyclone (Logan, Utah). O-phenylenediamine, hydrogen peroxide, 3-aminopropyltriethoxy-silane and sterile, endotoxin-free saline (0.9% NaCl in 100 ml of water) were from Sigma (St. Louis, Mo.). SMPT was from Pierce (Rockford, Ill.). Proplex T containing factor VII (74 IU/ml), factor X and factor IX (17 IU/ml) was purchased from Baxter Diagnostics Inc. (McGraw Park, Ill.). Chromogenic substrate, S-2765, for measuring factor Xa proteolytic activity was obtained from Chromogenix (Franklin, Ohio). Purified factor Xa was purchased from American Diagnostica (Greenwich, Conn.).

96 and 48 flat bottom microtiter plates were obtained from Falcon (Becton Dickinson and Co., Lincoln Park, N.J.). Sepharose-Protein G beads and S200 Superdex were purchased from Pharmacia (Piscataway, N.J.). Recombinant murine IL-1α was purchased from R&D Systems (Minneapolis, Minn.).

2. Antibodies

The MK2.7 hybridoma, secreting a rat IgG1 antibody against murine VCAM-1, was obtained from the American Type Culture Collection (ATCC, Rockville, Md.; ATCC CRL 1909). The characterization of this anti-VCAM-1 antibody has been reported by Miyake et al. (1991, incorporated herein by reference). The R187 hybridoma, secreting a rat IgG1 antibody against murine viral protein p30 gag, was also obtained from the ATCC, and was used as an isotype matched control for the anti-VCAM-1 antibody.

Mouse monoclonal antibody, 10H10, against human tissue factor was prepared as described in Morrissey et al. (1988), and in U.S. application Ser. No. 08/482,369, each incorporated herein by reference.

MECA 32, a pan anti-mouse vascular endothelial cell antibody, was prepared as described by Leppink et al. (1989, incorporated herein by reference). MJ 7/18 rat IgG, reactive with murine endoglin, was prepared as described by Ge and Butcher (1994, incorporated herein by reference). The MECA 32 and MJ 7/18 antibodies served as positive controls for immunohistochemical studies.

Rabbit anti-rat and rat anti-mouse secondary antibodies conjugated with horseradish peroxidase (HRP) were purchased from Dako (Carpinteria, Calif.).

3. Antibody Purification

Anti-VCAM-1 hybridoma, MK 2.7, and the irrelevant control hybridoma, R187, were grown in bioreactors (Heraeus, Inc., Germany) for 12 days. Supernatants were centrifuged, filtered through 0.22 μm filters and loaded onto Sepharose-Protein G columns. IgG was eluted with citric acid buffer, pH 3.5, dialyzed into PBS and stored thereafter at 4° C. in the same buffer. Purity was estimated by SDS-PAGE and was routinely >90%. Binding capacity of the purified anti-VCAM-1 antibody was assessed immunohistochemically on frozen sections of L540 tumor and by cell-based ELISA using IL-1α stimulated bEnd.3 cells, as described herein below.

4. Tumor-Bearing Mice and Immunohistochemistry

Male CB17 SCID mice (Charles River, Wilmington, Mass.) weighing approximately 25 g were injected with 1×10$^7$ L540 Hodgkin's lymphoma cells subcutaneously into the right flank. Tumors were allowed to grow to a size of 0.4–0.7 cm$^3$. Animals were anesthetized with metafane and their blood circulation was perfused with heparinized saline as described by Burrows et al. (1992, incorporated herein by reference). The tumor and major organs were removed and snap-frozen in liquid nitrogen.

Cryostat sections of the tissues were cut, incubated with the anti-VCAM-1 antibody and stained immunohistochemically to detect VCAM-1. Rat IgG was detected using rabbit anti-rat IgG conjugated to HRP followed by development with carbazole (Fries et al., 1993).

B. Results

The blood vessels of the major organs and a tumor from mice bearing subcutaneous L540 human Hodgkin's tumors were examined immunohistochemically for VCAM-1 expression using an anti-VCAM-1 antibody. VCAM-1 expression on tumor blood vessels was more peripheral than central. However, as demonstrated in Example VI and Example VII, the anti-VCAM-1 antibody and coaguligand were evidently binding to blood transporting vessels, as clearly shown by the ability of the coaguligand to arrest blood flow in all tumor regions and to cause destruction of the intratumoral region.

Overall, VCAM-1 expression was observed on 20–30% of total tumor blood vessels stained by the anti-endoglin antibody, MJ 7/18. VCAM-1 staining of the tumor vessels was largely observed on venules. VCAM-1 expression was similar in tumors up to 1500 mm$^3$, but larger tumors appeared to have reduced staining, with 5–10% of MJ 7/18 positive vessels being positive for VCAM-1.

Constitutive vascular expression of VCAM-1 was found in heart and lungs in both tumor-bearing and normal animals (Table 1). In the heart, strong staining was observed on venules and veins. Approximately 10% of MECA 32 positive vessels were positive for VCAM-1. Staining in lung endothelium was weak in comparison to heart and tumor, and was confined to a few large blood vessels. Strong stromal staining was observed in testis where VCAM-1 expression was strictly extravascular. Similar findings regarding constitutive VCAM-1 expression in rodent lung and testis were previously reported (Fries et al., 1993).

TABLE 1

Expression of VCAM-1 on Endothelium in Tissues of L540 Tumor Bearing Mice and Localization of Anti-VCAM-1 Antibody

| Tissue | VCAM-1 expression[a] | anti-VCAM-1 antibody localization[b] |
| --- | --- | --- |
| Adrenal | –[c] | – |
| Brain Cerebellum | – | – |
| Brain Cortex | – | – |
| Heart | ++ | ++ |
| Kidney | – | – |
| Large Intestine | – | – |
| Liver | – | – |
| Lung | + | + |
| Pancreas | – | – |
| Small Intestine | – | – |
| Spleen | – | – |
| Testis | –[d] | – |
| L540 Hodgkin's tumor | +++ | +++ |

[a]VCAM-1 was detected by anti-VCAM-1 antibody followed by anti-rat IgG-HRP.
[b]Localization of anti-VCAM-1 antibody in vivo was determined by injecting the antibody, exsanguinating the mice and staining tissues staining with anti-rat IgG-HRP.
[c]Intensity of staining was compared to pan-endothelial markers MJ 7/18 and MECA 32; – no staining; + weak; ++ moderate; +++ strong.
[d]No vascular expression was observed; however, extravascular stroma of testis was stained by anti-VCAM-1 antibody.

EXAMPLE II

Localization of Anti-VCAM-1 Antibody In Vivo

A. Methods

Male CB17 SCID mice (Charles River, Wilmington, Mass.) weighing approximately 25 g were injected with 1×10$^7$ L540 Hodgkin's lymphoma cells subcutaneously into the right flank. Tumors were allowed to grow to a size of 0.4–0.7 cm$^3$.

Mice were injected intravenously with 30 μg/25 g body weight of anti-VCAM-1 antibody, R187 antibody or corresponding coaguligands in 200 μl of saline. Two hours later, animals were anesthetized with metafane and their blood circulation was perfused with heparinized saline as described (Burrows et al., 1992; incorporated herein by reference). The tumor and major organs were removed and snap-frozen in liquid nitrogen.

Cryostat sections of the tissues were cut and were stained immunohistochemically for the presence of rat IgG or TF. Rat IgG was detected using rabbit anti-rat IgG conjugated to HRP followed by development with carbazole (Fries et al., 1993). Coaguligand was detected using the 10H10 antibody that recognizes human tissue factor, followed by HRP-labeled anti-mouse IgG. 10H10 antibody does not cross-react detectably with murine tissue factor (Morrissey et al., 1988, incorporated herein by reference) or other murine proteins.

B. Results

Mice bearing subcutaneous L540 tumors were injected intravenously with anti-VCAM-1 antibody and, two hours later, the mice were exsanguinated. The tumor and normal organs were removed and frozen sections were prepared and examined immunohistochemically to determine the location of the antibody. Serial sections of the tissues were examined. Localized rat IgG was detected by HRP-labeled anti-rat Ig; and murine blood vessels were identified by pan-endothelial antibody, MECA 32.

Anti-VCAM-1 antibody was detected on endothelium of tumor, heart and lung (Table 1). The intensity and number of stained vessels was identical to that on serial sections of the same tissues stained directly with anti-VCAM-1 antibody (Table 1). Staining was specific as no staining of endothelium was observed in the tumor and organs of mice injected with a species isotype matched antibody of irrelevant specificity, R187. No localization of anti-VCAM-1 antibody was found in testis or any normal organ except heart and lung.

EXAMPLE III

Preparation of Anti-VCAM-1.tTF Coaguligand

An anti-VCAM-1.tTF conjugate or "coaguligand" was prepared as follows. Truncated tissue factor (tTF), with an additional added cysteine introduced at N-terminus (U.S. application Ser. No. 08/482,369, incorporated herein by reference), was expressed in *E. coli* and purified as described by Stone et al. (1995, incorporated herein by reference). After purification, the sulfhydryl group of N' cysteine-tTF was protected by reaction with Ellman's reagent. The tTF derivative was stored in small volumes at −70° C.

To prepare the anti-VCAM-1 coaguligand, 5 ml of anti-VCAM-1 antibody IgG (2 mg/ml) in PBS were mixed with 36 µL of SMPT (10 mM) dissolved in dry DMF and incubated at room temperature for 1 h. The mixture was filtered through a column of Sephadex G25 equilibrated in PBS containing 1 mM EDTA. The fractions containing the SMPT-derivatized antibody were concentrated to 4 ml by ultrafiltration in an Amicon cell equipped with a 10,000 Da cut-off filter. Freshly thawed tTF derivative was incubated with 30 µl of DTT (10 mM) in $H_2O$ for 10 min. at room temperature and was filtered through a column of Sephadex G25 equilibrated in PBS containing 1 mM EDTA. The eluted fractions containing reduced tTF were concentrated by ultrafiltration under nitrogen to a final volume of 3 ml.

The reduced tTF was mixed with the SMPT-derivatized antibody and the mixture was allowed to react for 24 h at room temperature. At the end of the incubation, the reaction mixture was resolved by gel filtration on a column of Superdex S200 equilibrated in PBS. Fractions containing anti-VCAM-1.tTF having a $M_r$ of 180,000 and corresponding to one molecule of antibody linked to one molecule of tTF were collected.

EXAMPLE IV

Binding of Anti-VCAM-1 Coaguligand to Activated Endothelial Cells

A. Methods

1. Iodination of 10H10 Antibody

Anti-human tissue factor antibody, 10H10, was radiolabeled with $^{125}I$ using Chloramine T as described by Bocci (1964, incorporated herein by reference). The specific activity was approximately 10,000 cpm/µg, as calculated from protein determinations measured by a Bradford assay (Bradford, 1976).

2. Cells

L540 Hodgkin cells (L540 Cy), derived from a patient with end-stage disease, were prepared as described in Diehl et al. (1985, incorporated herein by reference), and were obtained from Prof. Volker Diehl (Klinik fur Innere Medizin der Universitaet, Köeln, Germany). bEnd.3 cells (murine brain endothelioma) were prepared as described in Bussolino et al. (1991) and Montesano et al. (1990), each incorporated herein by reference, and were obtained from Prof. Werner Risau (Max Planck Institute, Bäd Nauheim, Germany).

3. Tissue Culture bEnd.3 cells and hybridomas were maintained in DMEM supplemented with 10% fetal calf serum, 2 mM L-glutamine, 2 units/ml penicillin G and 2 µg/ml streptomycin. L540 cells were maintained in RPMI 1640 containing the same additives. All cells were subcultured once a week. bEnd.3 trypsinization was performed using 0.125% trypsin in PBS solution containing 0.2% EDTA. For binding studies, cells were seeded at a density of $5 \times 10^4$ cells/ml in 0.5 ml of medium in 48 well plates and incubated for 48–96 h. Medium was refreshed 24 h before each study.

4. Binding of Coaguligand to Activated Endothelial Cells

Binding of the anti-VCAM-1 antibody and coaguligand to VCAM-1 on activated bEnd.3 cells was determined using a cell based ELISA, as described by Hahne (1993, incorporated herein by reference). bEnd.3 cells were incubated with 10 units/ml of IL-1α for 4 h at 37° C. in 96-well microtiter plates. At the end of this incubation, medium was replaced by DPBS containing 2 mM $Ca^{2+}$ and $Mg^{2+}$ and 0.2% (w/v) gelatin as a carrier protein. The same buffer was used for dilution of antibodies and for washing of cell monolayers between steps.

Cells were incubated with 4 µg/ml of anti-VCAM-1.tTF conjugate, anti-VCAM-1 antibody or control reagents for 2 h, and were then washed and incubated for 1 h with rabbit anti-rat IgG-HRP conjugate (1:500 dilution). All steps were performed at room temperature. HRP activity was measured by adding O-phenylenediamine (0.5 mg/ml) and hydrogen peroxide (0.03% w/v) in citrate-phosphate buffer, pH 5.5. After 30 min., 100 µl of supernatant were transferred to 96 well plates, 100 µl of 0.18 M $H_2SO_4$ were added and the absorbance was measured at 492 nm. Each study was performed in duplicate and repeated at least twice.

5. Detection of Coaguligand Bound to Endothelial Cells

Anti-VCAM-1 coaguligand and appropriate controls were incubated with IL-1α stimulated bEnd.3 cells in 96-well microtiter plates, as described above. Bound coaguligands were detected by identifying both the tissue factor component and the rat IgG component bound to bEnd.3 cells.

After removing the excess of unbound antibody, cells were incubated with 100 µl/well of $^{125}I$-labeled 10H10 antibody (0.2 µg/ml) or $^{125}I$-labeled rabbit anti-rat Ig (0.2 µg/ml) in binding buffer. After 2 h incubation at room temperature, cells were washed extensively and dissolved in 0.5 M of NaOH. The entire volume of 0.5 ml was transferred to plastic tubes and counted in a γ counter. Each study was performed in duplicate and repeated at least twice.

B. Results

The ability of an anti-VCAM-1.tTF coaguligand to bind to IL-1α activated murine bEnd.3 cells was determined by measuring the binding of radioiodinated anti-TF antibody to coaguligand-treated cells in vitro. VCAM-1 expression by bEnd.3 cells is transiently inducible by IL-1α with a peak of VCAM-1 expression being obtained 4–6 h after addition of the cytokine (Hahne et al., 1993). Strong binding of the coaguligand to activated bEnd.3 cells was observed (FIG. 1A).

At saturation, 8.7 fmoles of anti-TF antibody was bound to the cells, which is equivalent to 540,000 molecules of anti-TF antibody per cell. Binding of the coaguligand was specific; no detectable binding over background was observed with an isotype matched control coaguligand of irrelevant specificity. Binding of coaguligand to unstimulated cells was about half of that to activated cells and is probably attributable to constitutive VCAM-1 expression by cultured endothelioma cells.

In further studies, the anti-VCAM-1.tTF coaguligand was found to bind as strongly as unconjugated anti-VCAM-1 antibody to activated bEnd.3 cells, using detection by peroxidase-labeled anti rat IgG in the assay. This was done at both saturating and subsaturating concentrations. Thus, the conjugation procedure (Example III) did not diminish antibody's capacity to bind to VCAM-1 on intact endothelial monolayers.

EXAMPLE V

Factor X Activation by Endothelial Cell-Bound Coaguligand

A. Methods

The activity of the anti-VCAM-1.tTF coaguligand bound to activated bEnd.3 cells was determined indirectly by using a chromogenic assay to detect factor Xa (Schorer et al., 1985; Nawroth et al., 1985; each incorporated herein by reference). IL-1α-stimulated and unstimulated bEnd.3 cells were incubated with specific and control coaguligands in 96-well microtiter plates as described above. The cells were washed with PBS containing 2 mg/ml of BSA and were incubated with 150 µl/well of freshly prepared Proplex T solution diluted 1:20 in 50 mM Tris-HCl (pH 8.1), 150 mM NaCl, 2 mg/ml BSA (tissue culture grade, endotoxin-free) and 2.5 mM $CaCl_2$. After incubation for 60 min. at 37° C., 100 µl were withdrawn from each well, transferred to 96-well plates and mixed with 100 µl of the same buffer containing 12.5 mM EDTA (pH 8.1).

Chromogenic substrate S2765 for measuring factor Xa proteolytic activity was added in 50 µl, giving a final concentration of 300 µM. The breakdown of the substrate was determined by reading the absorbance at 405 nm over a 2 h period in a microplate reader (Molecular Devices, Palo Alto, Calif.).

Production of the chromogenic product was completely dependent on the presence of Proplex T and bEnd.3 cells preincubated with the specific coaguligand. Background hydrolysis of the substrate by Proplex T in the absence of cells was approximately 10% of the maximal value and was subtracted from each determination. Free coaguligands diluted in Proplex T solution were unable to generate factor Xa. The amount of Xa generated was calculated by reference to a standard curve constructed with known concentrations of purified factor Xa.

At the end of the study, cells were detached with trypsin-EDTA and counted. The results are expressed as the amount of factor Xa generated per $10^4$ cells. Each study was performed in duplicate and was repeated at least 3 times.

B. Results

1. Factor X Activation

Figure 1B:
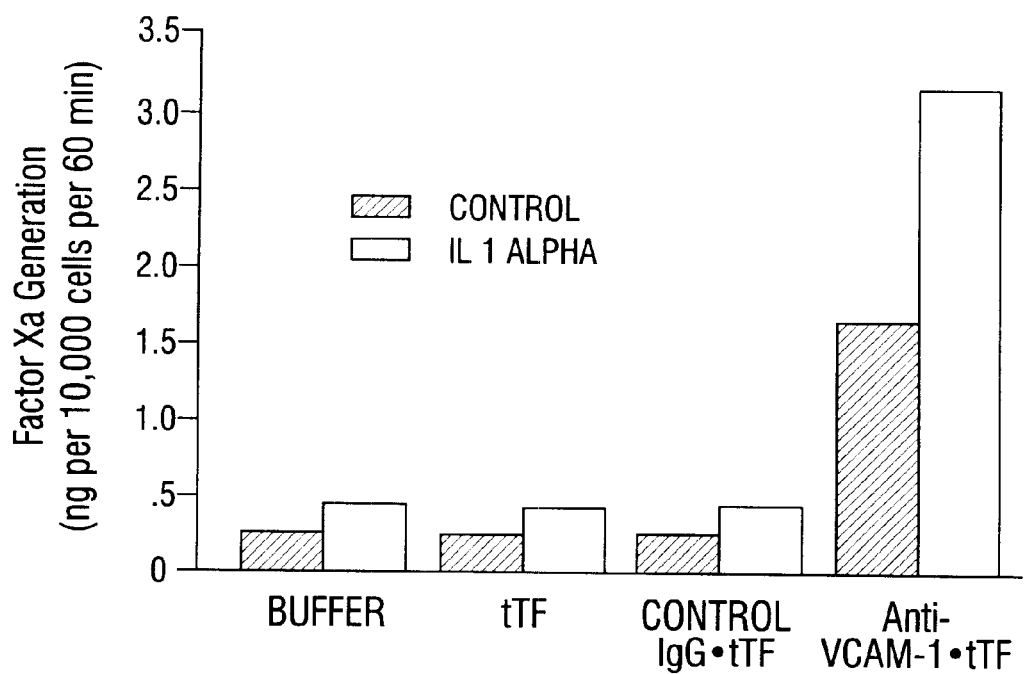

Anti-VCAM-1.tTF coaguligand bound to IL-1α-activated bEnd.3 cells was capable of specifically activating factor X. The rate of generation of factor Xa by anti-VCAM-1.tTF coated cells was 3.2 ng per $10^4$ cells per hour, which is 7–10 fold higher than was observed with activated cells treated with a control coaguligand of irrelevant specificity or with tTF alone (FIG. 1B). Anti-VCAM-1.tTF in the absence of cells had undetectable factor X activating activity, confirming that cell binding is essential for coaguligand activity.

Anti-VCAM-1-tTF bound to unstimulated bEnd.3 cells activated factor X at a rate of 1.6 ng per $10^4$ cells per hour. This rate is about half that observed with the IL-1α-stimulated cells, in accordance with the 50% lower amount of coaguligand that binds to unstimulated as compared with stimulated cells. Similar results to those shown in FIG. 1B were obtained in three separate studies.

2. Effect of Endothelial Cell Permeabilization

Permeabilization of bEnd.3 monolayers with saponin after treating them with anti-VCAM-1.tTF coaguligand increased the ability of the bound coaguligand to activate factor X by about 30-fold (Table 2). The rate of factor Xa generation by unstimulated cells treated with anti-VCAM-1.tTF increased from 1.6 to 49.2 ng per $10^4$ cells per hour after permeabilization, while that of IL-1α stimulated cells increased from 3.2 to 98.8 ng per $10^4$ cells per hour. The factor Xa generating activity of the permeabilized cells was due to the bound coaguligand rather than to endogenous TF since permeabilized untreated cells or cells treated with control coaguligand of irrelevant specificity had low factor Xa generating activity (2 ng per $10^4$ cells per hour).

These results indicate that the coaguligand is able to function more efficiently in the environment of a permeabilized cell. Possibly, permeabilization exposes negatively-charged phospholipids from within the cell that accelerate the formation of the coagulation-initiation complexes, or else prevents the inactivation of such complexes by TFPI.

TABLE 2

Generation of Factor Xa by Anti-VCAM-1·tTF Bound to Intact or Permeabilized bEnd·3 cells (ng per $10^4$ cells per 60 min.)

| Treatment[a] | Intact cells | | Permeabilized cells[b] | |
|---|---|---|---|---|
| | Control | IL-1α | Control | IL-1α |
| Buffer | 0.25[c] | 0.43 | 0.45 | 2.0 |
| tTF | 0.26 | 0.42 | 0.39 | 2.1 |
| Control IgG·tTF | 0.26 | 0.43 | 0.41 | 2.1 |
| Anti-VCAM-1·tTF | 1.64 | 3.17 | 49.2 | 98.8 |

[a]IL-1α stimulated and unstimulated bEnd.3 cells were incubated with buffer alone or with 4 µg/ml of tTF, control IgG·tTF or anti-VCAM-1·tTF followed by 60 min. incubation with Proplex T solution at 37° C.
[b]Cells were treated with 0.2% saponin 5 min. before addition of Proplex T.
[c]Amount of factor Xa was determined as described above. Results are expressed as ng of factor Xa generated per $10^4$ cells per 60 min. The arithmetic mean values from triplicate wells are shown. SE were less than 5 percent of the mean values.

EXAMPLE VI

Tumor Blood Vessel Thrombosis by Anti-VCAM-1 Coaguligand

A. Methods

SCID mice bearing L540 tumors (0.4–0.7 $cm^3$) were injected intravenously with 40 µg (total protein) of anti-VCAM-1.tTF or R187.tTF. This dose corresponds to 32 µg of antibody and 8 µg of tTF. Other animals received equivalent quantities of free antibody, free tTF or a mixture of both. Animals were anesthetized 4 or 24 h later and their blood circulations were perfused with heparinized saline. The tumor and major organs were removed and were fixed in formalin and paraffin-embedded or snap-frozen for cryosectioning. Sections were cut through the center of the tissue or tumor. The number of thrombosed and non-thrombosed blood vessels in 5 cross-sections were counted. The percentage of thrombosed vessels was calculated.

B. Results
1. Thrombosis of Tumor Blood Vessels

This study shows that intravenous administration of the anti-VCAM-1.tTF coaguligand induces selective thrombosis of tumor blood vessels, as opposed to vessels in normal tissues, in tumor-bearing mice.

The anti-VCAM-1.tTF coaguligand was administered to mice bearing subcutaneous L540 tumors of 0.4 to 0.6 cm in diameter. Before coaguligand injection, tumors were healthy, having a uniform morphology lacking regions of necrosis. The tumors were well vascularized and had a complete absence of spontaneously thrombosed vessels or hemorrhages. Within four hours of coaguligand injection, 40–70% of blood vessels were thrombosed, despite the initial staining of only 20–30% of tumor blood vessels shown in Example I. The thrombosed vessels contained occlusive platelet aggregates, packed erythrocytes and fibrin. In several regions, the blood vessels had ruptured, spilling erythrocytes into the tumor interstitium.

By 24 h after coaguligand injection, the blood vessels were still occluded and extensive hemorrhage had spread throughout the tumor. Tumor cells had separated from one another, had pyknotic nuclei and were undergoing cytolysis. By 72 h, advanced necrosis was evident throughout the tumor. Necrosis was clearly present in the intratumoral region of the tumor, where VCAM-1 expression on the vessels was not originally prominent. The coaguligand binding was evidently effective to curtail blood flow in all tumor regions, resulting in widespread tumor destruction. Furthermore, it is likely that the initial coaguligand-induced thrombin deposition results in increased induction of the VCAM-1 target antigen on central vessels, thus amplifying targeting and tumor destruction.

The thrombotic action of anti-VCAM-1.tTF on tumor vessels was antigen specific. None of the control reagents administered at equivalent quantities (tTF alone, anti-VCAM-1 antibody alone, tTF plus anti-VCAM-1 antibody or the control coaguligand of irrelevant specificity) caused thrombosis (Table 3).

TABLE 3

Anti-VCAM-1·tTF-Mediated Thrombosis in L540 Tumor Bearing Mice

| Treatment[a] | Thrombosed Vessels (%)[b] | | |
|---|---|---|---|
| | L540 Tumor | Heart and Lung | Other Organs |
| Saline | 0–2 | 0 | 0 |
| TTF | 0–2 | 0 | 0 |
| Anti-VCAM-1 Antibody | 0–2 | 0 | 0 |
| Anti-VCAM-1 Antibody + tTF | 0–2 | 0 | 0 |
| Control IgG·tTF | 0–2 | 0 | 0 |
| Anti-VCAM-1·tTF (<0.3 cm3)[c] | 0–10 | 0 | 0 |
| Anti-VCAM-1·tTF (>0.3 cm$^3$) | 40–70 | 0 | 0 |

[a]L540 tumor-bearing mice were injected i.v. with one of the following reagents: saline; 8 µg of unconjugated tTF; 32 µg of unconjugated anti-VCAM-1 antibody; mixture of 8 µg of tTF and 32 µg of anti-VCAM-1 antibody; 40 µg of control IgG·tTF coaguligand; or 40 µg of anti-VCAM-1·tTF coaguligand. Animals were sacrificed 4 h after injection. Tissues were removed and fixed in formalin.
[b]Histological quantification was performed by counting numbers of thrombosed blood vessels in 5 cross sections of tissue. The number of thrombosed vessels is expressed as a percentage of total vessels. The range of results from three mice is given.
[c]L540 tumor bearing mice were divided into two groups (5–8 animals per group) having tumors smaller or larger than 0.3 cm$^3$.

2. Lack of Thrombosis of Normal Blood Vessels

In addition to the thrombosis of tumor blood vessels, this study also shows that intravenous administration of the anti-VCAM-1.tTF coaguligand does not induce thrombosis of blood vessels in normal organs.

Despite expression of VCAM-1 on vessels in the heart and lung of normal or L540 tumor-bearing mice (Table 1), thrombosis did not occur after anti-VCAM-1.tTF coaguligand administration. No signs of thrombosis, tissue damage or altered morphology were seen in 25 mice injected with 5 to 45 µg of coaguligand 4 or 24 h earlier. There was a normal histological appearance of the heart and lung from the same mouse that had major tumor thrombosis. All other major organs (brain, liver, kidney, spleen, pancreas, intestine, testis) also had unaltered morphology.

Frozen sections of organs and tumors from coaguligand-treated mice gave coincident staining patterns when developed with either the anti-TF antibody, 10H10, or an anti-rat IgG antibody and confirmed that the coaguligand had localized to vessels in the heart, lung and tumor. The intensity of staining was equal to that seen when coaguligand was applied directly to the sections at high concentrations followed by development with anti-TF or anti-rat IgG, indicating that saturation of binding had been attained in vivo.

These studies show that binding of coaguligand to VCAM-1 on normal vasculature in heart and lung is not sufficient to induce thrombosis, and that tumor vasculature provides additional factors to support coagulation.

EXAMPLE VII

In Vivo Tumor Destruction by Anti-VCAM-1 Coaguligand

A. Methods

Male CB17 SCID mice were injected subcutaneously with 1×10$^7$ L540 cells as described above. When the tumors had reached a volume of 0.4–0.6 cm$^3$, the mice were injected intravenously with either 20 µg of anti-VCAM-1.tTF, 16 µg anti-VCAM-l antibody, 4 µg tTF, a mixture of 16 µg of anti-VCAM-1 antibody and 4 µg of tTF, 20 µg control IgG.tTF or saline. In some studies, the treatment was given 3 times, on days 0, 4 and 8. A minimum of 8 animals were treated in each group.

Animals were monitored daily for tumor measurements and body weight. Mice were sacrificed when tumors had reached a diameter of 2 cm$^3$, or earlier if tumors showed signs of necrosis or ulceration. Tumor volume was calculated according to the formula: $\pi/6 \times D \times d^2$, where D is the larger tumor diameter and d is the smaller diameter. Differences in tumor growth rates were tested for statistical significance using a non-parametric test (Mann-Whitney rank sum test) that makes no assumptions about tumor size being normally distributed (Gibbons, 1976).

B. Results

Figure 2:
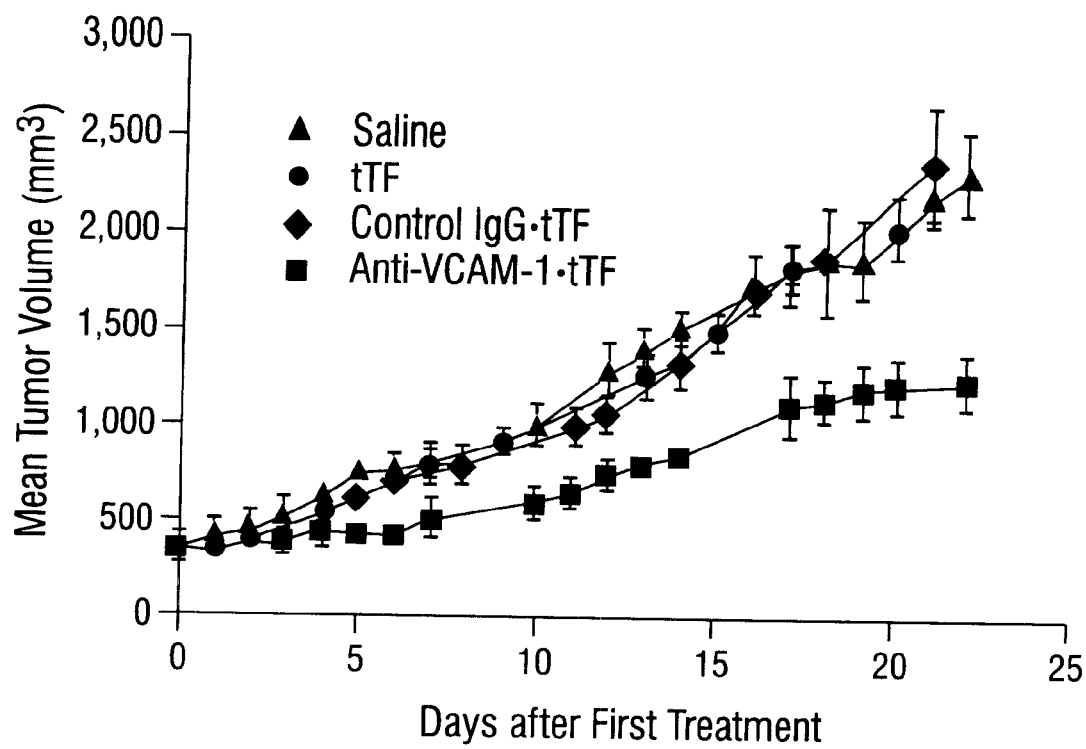
FIG. 2. Retardation of growth of L540 tumors in mice treated with anti-VCAM-1.tTF. L540 tumor bearing mice were injected i.v. with either saline, 20 µg of anti-VCAM-1.tTF, 4 µg of unconjugated tTF or 20 µg of control IgG.tTF. Injections were repeated on day 4 and 8 after the first treatment. Tumors were measured daily. Mean tumor volume and SD of 8 mice per group is shown.

The anti-tumor activity of anti-VCAM-1.tTF coaguligand was determined in SCID mice bearing 0.3–0.4 cm$^3$ L540 tumors. The drug was administered i.v. 3 times at intervals of 4 days. The pooled results from 3 separate studies are presented in FIG. 2 and Table 4. Mean tumor volume of anti-VCAM-1.tTF treated mice was significantly reduced at 21 days of treatment (P<0.001) in comparison to all other groups. Nine of a total of 15 mice treated with the specific coaguligand showed more than 50% reduction in tumor volume. This effect was specific since unconjugated tTF, control IgG coaguligand and mixture of free anti-VCAM-1 antibody and tTF did not affect tumor growth.

TABLE 4

Inhibition of Tumor Growth by Anti-VCAM-tTF Coaguligand

| Treatment[a] | N | Mean tumor volume (mm³)[b] Day 0 | Mean tumor volume (mm³)[b] Day 21 | Tumor Growth Index[c] | P versus saline[d] |
|---|---|---|---|---|---|
| Saline | 14 | 331 ± 61 | 2190 ± 210 | 6.91 | — |
| TTF | 13 | 341 ± 22 | 2015 ± 205 | 5.90 | NS |
| Anti-VCAM-1 | 16 | 363 ± 24 | 1920 ± 272 | 5.28 | NS |
| Anti-VCAM-1+tTF | 13 | 349 ± 42 | 2069 ± 362 | 5.92 | NS |
| Control IgG·tTF | 8 | 324 ± 30 | 2324 ± 304 | 7.17 | NS |
| Anti-VCAM-1·tTF | 15 | 365 ± 28 | 1280 ± 130 | 3.50 | <0.001 |

[a]L540 tumor bearing mice were injected i.v. with one of the following reagents: saline; 8 μg of unconjugated tTF; 32 μg of unconjugated anti-VCAM-1 antibody; mixture of 8 μg of tTF and 32 μg of anti-VCAM-1 antibody; 40 μg of control IgG·tTF (R187) coaguligand; or 40 μg of anti-VCAM-1·tTF coaguligand. The treatment was repeated on day 4 and 7 after first injection.
[b]Mean tumor volume ± SD.
[c]The tumor growth index is the ratio of mean tumor volume on day 21 to mean tumor volume on day 0.
[d]Two tailed P values are for differences in tumor volume (day 21) for the treated groups versus the saline group as determined by the Mann-Whitney rank sum test.

EXAMPLE VIII

Phosphatidylserine Expression on Tumor Blood Vessels

A. Methods

1. Antibodies

Anti-phosphatidylserine (anti-PS) and anti-cardiolipin antibodies, both mouse monoclonal IgM antibodies, were produced as described by Rote (Rote et al., 1993). Details of the characterization of the anti-PS and anti-cardiolipin antibodies were also reported by Rote et al. (1993, incorporated herein by reference).

2. Detection of PS Expression on Vascular Endothelium

L540 tumor-bearing mice were injected i.v. with 20 μg of either anti-PS or anti-cardiolipin mouse IgM antibodies. After 10 min., mice were anesthetized and their blood circulations were perfused with heparinized saline. Tumors and normal tissues were removed and snap-frozen. Serial sections of organs and tumors were stained with either HRP-labeled anti-mouse IgM for detection of anti-PS antibody or with anti-VCAM-1 antibody followed by HRP-labeled anti-rat Ig.

To preserve membrane phospholipids on frozen sections, the following protocol was developed. Animals were perfused with DPBS containing 2.5 mM Ca²⁺. Tissues were mounted on 3-aminopropyltriethoxysilane-coated slides and were stained within 24 h. No organic solvents, formaldehyde or detergents were used for fixation or washing of the slides. Slides were re-hydrated by DPBS containing 2.5 mM Ca²⁺ and 0.2% gelatin. The same solution was also used to wash sections to remove the excess of reagents. Sections were incubated with HRP-labeled anti-mouse IgM for 3.5 h at room temperature to detect anti-PS IgM.

B. Results

To explain the lack of thrombotic effect of anti-VCAM-1.tTF on VCAM-1 positive vasculature in heart and lungs, the inventors developed a concept of differential PS localization between normal and tumor blood vessels. Specifically, they hypothesized that endothelial cells in normal tissues segregate PS to the inner surface of the plasma membrane phospholipid bilayer, where it is unable to participate in thrombotic reactions; whereas endothelial cells in tumors translocate PS to the external surface of the plasma membrane, where it can support the coagulation action of the coaguligand. PS expression on the cell surface allows coagulation because it enables the attachment of coagulation factors to the membrane and coordinates the assembly of coagulation initiation complexes (Ortel et al., 1992).

The inventors' model of PS translocation to the surface of tumor blood vessel endothelial cells, as developed herein, is surprising in that PS expression does not occur after, and does not inevitably trigger, cell death. PS expression at the tumor endothelial cell surface is thus sufficiently stable to allow PS to serve as a targetable entity for therapeutic intervention.

To confirm the hypothesis that tumor blood vessel endothelium expresses PS on the luminal surface of the plasma membrane, the inventors used immunohistochemistry to determine the distribution of anti-PS antibody after intravenous injection into L540 tumor bearing mice. Anti-PS antibody localized within 10 min. to the majority of tumor blood vessels, including vessels in the central region of the tumor that can lack VCAM-1. Vessels that were positive for VCAM-1 were also positive for PS. Thus, there is coincident expression of PS on VCAM-1-expressing vessels in tumors.

In the in vivo localization studies, none of the vessels in normal organs, including VCAM-1-positive vasculature of heart and lung, were stained, indicating that PS is absent from the external surface of the endothelial cells. In contrast, when sections of normal tissues and tumors were directly stained with anti-PS antibody in vitro, no differences were visible between normal and tumor, endothelial or other cell types, showing that PS is present within these cells but only becomes expressed on the surface of endothelial cells in tumors.

The specificity of PS detection was confirmed by two independent studies. First, a mouse IgM monoclonal antibody directed against a different negatively charged lipid, cardiolipin, did not home to tumor or any organs in vivo. Second, pretreatment of frozen sections with acetone abolished staining with anti-PS antibody, presumably because it extracted the lipids together with the bound anti-PS antibody.

EXAMPLE IX

Annexin V Blocks Coaguligand Activation of Factor X In Vitro

A. Methods

The ability of Annexin V to affect Factor Xa formation induced by coaguligand was determined by a chromogenic assay described above in Example V. IL-1α-stimulated bEnd.3 cells were incubated with anti-VCAM-.tTF and permeabilized by saponin. Annexin V was added at concentrations ranging from 0.1 to 10 μg/ml and cells were incubated for 30 min. before addition of diluted Proplex T. The amount of Factor Xa generated in the presence or absence of Annexin V was determined as described in Example V. Each treatment was performed in duplicate and repeated at least twice.

B. Results

The need for surface PS expression in coaguligand action is further indicated by the inventors' finding that annexin V, which binds to PS with high affinity, blocks the ability of anti-VCAM-1.tTF bound to bEnd.3 cells to generate factor Xa in vitro.

Figure 3:
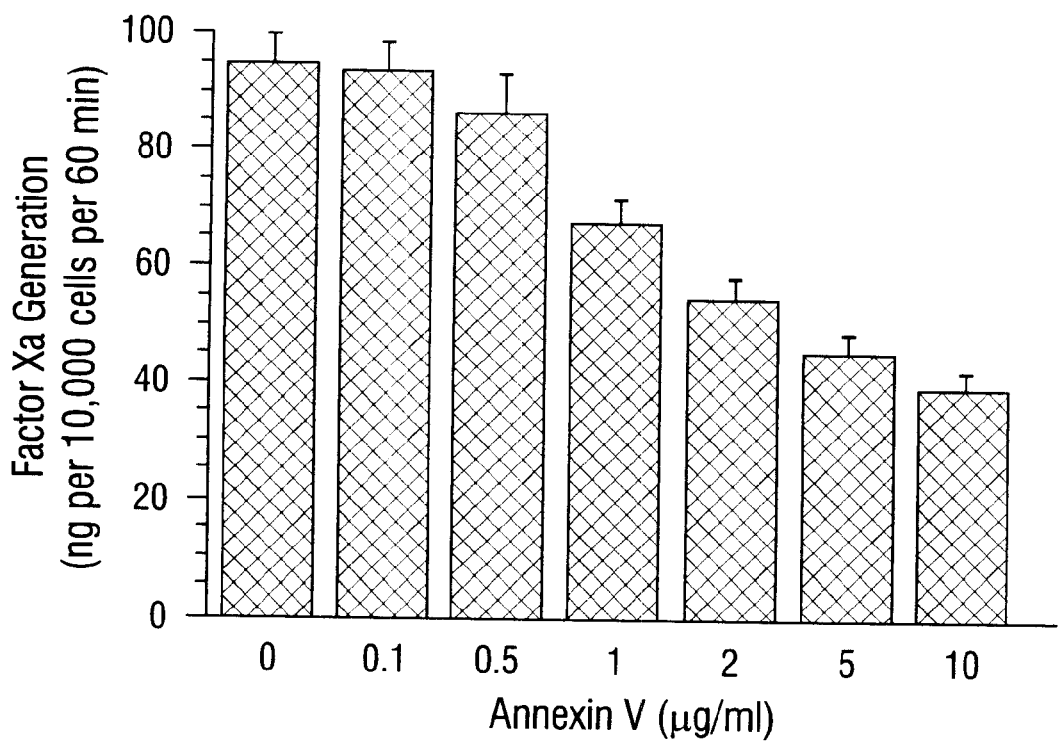
FIG. 3. Annexin V blocks coaguligand activation of Factor X in vitro. IL-1α-stimulated bEnd.3 cells were incubated with anti-VCAM.tTF coaguligand in 96-well microtiter plates, as described in Example V. Annexin V was added at concentrations ranging from 0.1 to 10 µg/ml (as shown) and cells were incubated for 30 min. before addition of diluted Proplex T. The amount of Factor Xa generated in the presence or absence of Annexin V was determined using a chromogenic substrate, as described in Example V.

Annexin V added to permeabilized cells preincubated with anti-VCAM-1.tTF inhibited the formation of factor Xa in a dose-dependent manner (FIG. 3). In the absence of Annexin V, cell-bound coaguligand produced 95 ng of factor Xa per 10,000 cells per 60 min. The addition of increasing amounts of Annexin V (in the μg per ml range) inhibited factor Xa production. At 10 μg per ml, Annexin V inhibited factor Xa production by 58% (FIG. 3). No further inhibition was observed by increasing the concentration of Annexin V during the assay, indicating that annexin V saturated all available binding sites at 10 μg per ml.

EXAMPLE X

Annexin V Blocks Coaguligand Activity In Vivo
A. Methods

The ability of Annexin V to inhibit coaguligand-induced thrombosis in vivo was examined in L540 Hodgkin-bearing SCID mice. Tumors were grown in mice as described above in Example II. Two mice per group (tumor size 0.5 cm in diameter) were injected intravenously via the tail vein with one of the following reagents: a) saline; b) 100 μg of Annexin V; c) 40 μg of anti-VCAM-1.tTF; d) 100 μg of Annexin V followed 2 hours later by 40 μg of anti-VCAM-1.tTF.

Four hours after the last injection mice were anesthetized and perfused with heparinized saline. Tumors were removed, fixed with 4% formalin, paraffin-embedded and stained with hematoxylene-eosin. The number of thrombosed and non-thrombosed blood vessels were counted and the percentage of thrombosis was calculated.

B. Results

Annexin V also blocks the activity of the anti-VCAM-1.tTF coaguligand in vivo. Groups of tumor-bearing mice were treated with one of the control or test reagents, as described in the methods. The mice were given (a) saline; (b) 100 μg of Annexin V; (c) 40 μg of anti-VCAM-1.tTF coaguligand; or (d) 100 μg of Annexin V followed 2 hours later by 40 μg of anti-VCAM-1.tTF coaguligand. Identical results were obtained in both mice per group.

No spontaneous thrombosis, hemorrhages or necrosis were observed in tumors derived from saline-injected mice. Treatment with Annexin V alone did not alter tumor morphology.

In accordance with other data presented herein, 40 μg of anti-VCAM-1.tTF coaguligand caused thrombosis in 70% of total tumor blood vessels. The majority of blood vessels were occluded with packed erythrocytes and clots, and tumor cells were separated from one another. Both coaguligand-induced anti-tumor effects, ie., intravascular thrombosis and changes in tumor cell morphology, were completely abolished by pre-treating the mice with Annexin V.

These findings confirm that the anti-tumor effects of coaguligands are mediated through the blockage of tumor vasculature. These data also demonstrate that PS is essential for coaguligand-induced thrombosis in vivo.

EXAMPLE XI

Externalized Phosphatidylserine is a Global Marker of Tumor Blood Vessels

A. Methods

PS exposure on tumor and normal vascular endothelium was examined in three animal tumor models: L540 Hodgkin lymphoma, NCI-H358 non-small cell lung carcinoma, and HT 29 colon adenocarcinoma (ATCC). To grow the tumors in vivo, $2 \times 10^6$ cells were injected into the right flank of SCID mice and allowed to reach 0.8–1.2 cm in diameter. Mice bearing large tumors (volume above 800 mm$^3$) were injected intravenously via the tail vein with 20 μg of either anti-PS or anti-cardiolipin antibodies. The anti-cardiolipin antibody served as a control for all studies since both antibodies are directed against negatively charged lipids and belong to the same class of immunoglobulins (mouse IgM).

One hour after injection, mice were anesthetized and their blood circulation was perfused with heparinized saline. Tumors and normal organs were removed and snap-frozen. Frozen sections were stained with anti-mouse IgM-peroxidase conjugate (Jackson Immunoresearch Labs) followed by development with carbazole.

B. Results

The anti-PS antibodies specifically homed to the vasculature of all three tumors (HT 29, L540 and NCI-H358) in vivo, as indicated by detection of the mouse IgM. The average percentages of vessels stained in the tumors were 80% for HT 29, 30% for L540 and 50% for NCI-H358. Vessels in all regions of the tumors were stained and there was staining both of small capillaries and larger vessels.

No vessel staining was observed with anti-PS antibodies in any normal tissues. In the kidney, tubules were stained both with anti-PS and anti-CL, and this likely relates to the secretion of IgMs by this organ (Table 5). Anti-cardiolipin antibodies were not detected in any tumors or normal tissues, except kidney.

These findings indicate that only tumor endothelium exposes PS to the outer site of the plasma membrane.

TABLE 5

Vessel Localization of Anti-PS and Anti-Cardiolipin Abs in Tumor-Bearing Mice*

| Tissue | Anti-PS† | Anti-Cardiolipin† |
|---|---|---|
| L540 Cy tumor | ++ | − |
| H358 tumor | ++ | − |
| HT29 tumor | +++ | − |
| Adrenal | − | − |
| Brain Cerebellum | − | − |
| Brain Cortex | − | − |
| Heart | − | − |
| Kidney | −‡ | −‡ |
| Large Intestine | − | − |
| Liver | − | − |
| Lung | − | − |
| Pancreas | − | − |
| Small Intestine | − | − |
| Spleen | − | − |
| Testes | − | − |

*Biodistribution in normal organs of both anti-PS and anti-cardiolipin Abs was identical in all three tumor animal models.
†Anti-PS and anti-cardiolipin antibodies were detected on frozen sections using anti-mouse IgM-peroxidase conjugate. − no staining; + weak; ++ moderate; +++ strong, equivalent to pan endothelial marker Meca 32.
‡Tubular staining was observed in the kidneys of both and-PS and anti-CL recipients.

To estimate the time at which tumor vasculature loses the ability to segregate PS to the inner side of the membrane, the inventors examined anti-PS localization in L540 tumors ranging in volume from 140 to 1,600 mm$^3$. Mice were divided into 3 groups according to their tumor size: 140–300, 350–800 and 800–1,600 mm$^3$. Anti-PS Ab was not detected in three mice bearing small L540 tumors (up to 300 mm$^3$). Anti-PS Ab localized in 3 animals of 5 in the group of intermediate size L540 tumors and in all mice (4 out of 4) bearing large L540 tumors (Table 6). Percent of PS-positive blood vessels from total (identified by pan endothelial marker Meca 32) was 10–20% in the L540 intermediate group and 20–40% in the group of large L540 tumors (Table 6).

TABLE 6

PS Externalization Detected in Mid and Large Sized Tumors

| Tumor Size (mm³) | No. Positive Tumors/Total* | % PS-Positive Vessels/Total† |
|---|---|---|
| 350–800 | 3/5 | 10–20 |
| 850–1,600 | 4/4 | 20–40 |

*Mice bearing L540 Cy tumors were divided into three groups according to tumor size. 20 µg of anti-PS antibodies were injected i.v. and allowed to circulate for 1 hour. Mouse antibodies were detected on frozen sections using anti-mouse IgM-peroxidase conjugate.
†Total number of blood vessels was determined using pan-endothelial Ab Meca 32. PS-positive and Meca-positive vessels were counted in 4 fields per cross section of tumor. Range of % PS-positive vessels within the same group is shown.

EXAMPLE XII

Anti-Tumor Effects of Unconjugated Anti-Phosphatidylserine Antibodies

A. Methods

The effects of anti-PS antibodies were examined in syngeneic and xenogeneic tumor models. For the syngeneic model, $1 \times 10^7$ cells of murine colorectal carcinoma Colo 26 (obtained from Dr. Ian Hart, ICRF, London) were injected subcutaneously into the right flank of Balb/c mice. In the xenogeneic model, a human Hodgkin's lymphoma L540 xenograft was established by injecting $1 \times 10^7$ cells subcutaneously into the right flank of male CB17 SCID mice. Tumors were allowed to grow to a size of about 0.6–0.9 cm³ before treatment.

Tumor-bearing mice (4 animals per group) were injected i.p. with 20 µg of naked anti-PS antibody (IgM), control mouse IgM or saline. Treatment was repeated 3 times with a 48 hour interval. Animals were monitored daily for tumor measurements and body weight. Tumor volume was calculated as described in Example VII. Mice were sacrificed when tumors had reached 2 cm³, or earlier if tumors showed signs of necrosis or ulceration.

B. Results

Figure 4A:
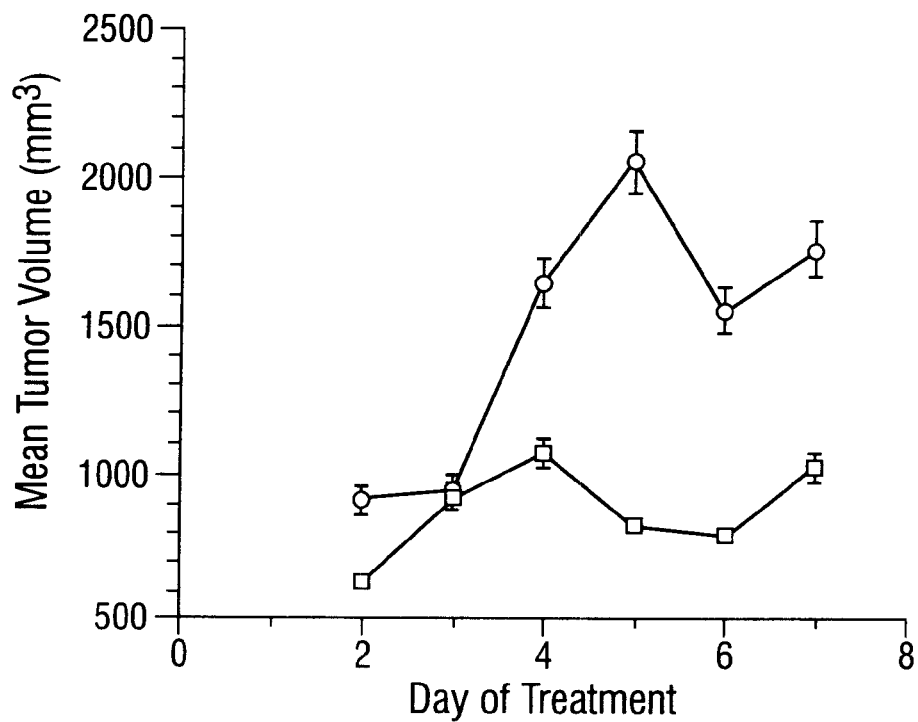
FIG. 4A and FIG. 4B. Anti-tumor effects of naked anti-PS antibodies in animals with syngeneic and xenogeneic tumors. $1 \times 10^7$ cells of murine colorectal carcinoma Colo 26 (FIG. 4A) or human Hodgkin's lymphoma L540 (FIG. 4B) were injected subcutaneously into the right flank of Balb/c mice (FIG. 4A) or male CB17 SCID mice (FIG. 4B), respectively. Tumors were allowed to grow to a size of about 0.6–0.9 cm$^3$ and then the mice (4 animals per group) were injected i.p. with 20 µg of naked anti-PS antibody (open squares) or saline (open circles) (control mouse IgM gave similar results to saline.). Treatment was repeated 3 times with a 48 hour interval. Animals were monitored daily for tumor measurements and body weight. Tumor volume was calculated as described in Example VII. Mice were sacrificed when tumors had reached 2 cm$^3$, or earlier if tumors showed signs of necrosis or ulceration.
Figure 4B:
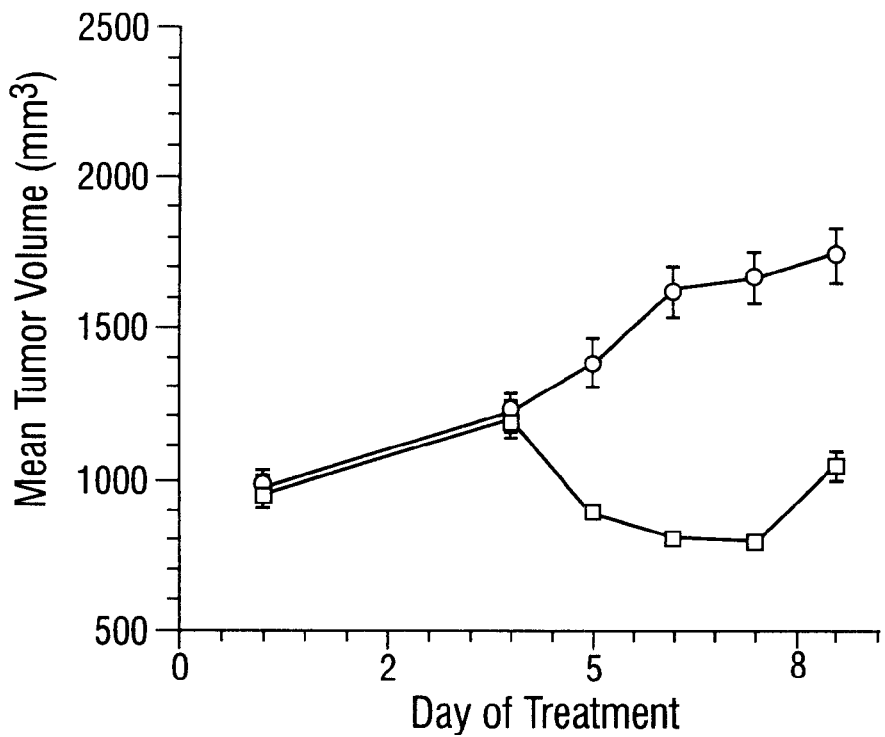

The growth of both syngeneic and xenogeneic tumors was effectively inhibited by treatment with naked anti-PS antibodies (FIG. 4A and FIG. 4B). Anti-PS antibodies caused tumor vascular injury, accompanied by thrombosis, and tumor necrosis. The presence of clots and disintegration of tumor mass surrounding blocked blood vessels was evident.

Quantitatively, the naked anti-PS antibody treatment inhibited tumor growth by up to 60% of control tumor volume in mice bearing large Colo 26 (FIG. 4A) and L540 (FIG. 4B) tumors. No retardation of tumor growth was found in mice treated with saline or control IgM. No toxicity was observed in mice treated with anti-PS antibodies, with normal organs preserving unaltered morphology, indistinguishable from untreated or saline-treated mice.

Tumor regression started 24 hours after the first treatment and tumors continue to decline in size for the next 6 days. This was observed in both syngeneic and immunocompromised tumor models, indicating that the effect was mediated by immune status-independent mechanism(s). Moreover, the decline in tumor burden was associated with the increase of alertness and generally healthy appearance of the animals, compared to control mice bearing tumors larger than 1500 mm³. Tumor re-growth occurred 7–8 days after the first treatment.

The results obtained with anti-PS treatment of L540 tumors are further compelling for the following reasons. Notably, the tumor necrosis observed in L540 tumor treatment occurred despite the fact that the percentage of vessels that stained positive for PS in L540 tumors was less than in HT 29 and NCI-H358 tumors. This implies that even more rapid necrosis would likely result when treating other tumor types. Furthermore, L540 tumors are generally chosen as an experimental model because they provide clean histological sections and they are, in fact, known to be resistant to necrosis.

EXAMPLE XIII

Anti-Tumor Effects of Annexin Conjugates

The surprising finding that aminophospholipids are stable markers of tumor vasculature also means that antibody-therapeutic agent constructs can be used in cancer treatment. In addition to using antibodies as targeting agents, the inventors reasoned that annexins, and other aminophospholipid-binding proteins, could also be used to specifically deliver therapeutic agents to tumor vasculature. The following data shows the anti-tumor effects that result from the in vivo administration of annexin-TF constructs.

A. Methods

An annexin V-tTF conjugate was prepared and administered to nu/nu mice with solid tumors. The tumors were formed from human HT29 colorectal carcinoma cells that formed tumors of at least about 1.2 cm³. The annexin V-tTF coaguligand (10 µg) was administered intravenously and allowed to circulate for 24 hours. Saline-treated mice were separately maintained as control animals. After the one day treatment period, the mice were sacrificed and exsanguinated and the tumors and major organs were harvested for analysis.

B. Results

The annexin V-tTF conjugate was found to induce specific tumor blood vessel coagulation in HT29 tumor bearing mice. Approximately 55% of the tumor blood vessels in the annexin V-tTF conjugate treated animals were thrombosed following a single injection. In contrast, there was minimal evidence of thrombosis in the tumor vasculature of the control animals.

EXAMPLE XIV

Phosphatidylserine Translocation in the Tumor Environment

The discovery of PS as an in vivo surface marker unique to tumor vascular endothelial cells prompted the inventors to further investigate the effect of a tumor environment on PS translocation and outer membrane expression. The present example shows that exposing endothelial cells in vitro to certain conditions that mimic those in a tumor duplicates the observed PS surface expression in intact, viable cells.

A. Methods

Mouse bEnd.3 endothelial cells were seeded at an initial density of 50,000 cells/well. Twenty-fours later cells were incubated with increasing concentrations of $H_2O_2$ (from 10 µM to 500 µM) for 1 hour at 37° C. or left untreated. At the end of the incubation, cells were washed 3 times with PBS containing 0.2% gelatin and fixed with 0.25% glutaraldehyde. Identical wells were either stained with anti-PS IgM or trypsinized and evaluated for viability by the Trypan Blue exclusion test. For the anti-PS staining, after blocking with 2% gelatin for 10 min., cells were incubated with 2 µg/ml of anti-PS antibody, followed by detection with anti-mouse IgM-HRP conjugate.

Wells seeded with mouse bEnd.3 endothelial cells were also incubated with different effectors and compared to control, untreated wells after the same period of incubation at 37° C. The panel of effectors tested included TNF, LPS, bFGF, IL-1α, IL-1β and thrombin. After incubation, cells were washed and fixed and were again either stained with anti-PS IgM or evaluated for viability using the Trypan Blue exclusion test, as described above.

B. Results

1. PS Induction by $H_2O_2$

Exposing endothelial cells to $H_2O_2$ at concentrations higher than 100 µM caused PS translocation in ~90% cells. However, this was accompanied by detachment of the cells from the substrate and cell viability decreasing to about 50–60%. The association of surface PS expression with decreasing cell viability is understandable, although it is still interesting to note that ~90% PS translocation is observed with only a 50–60% decrease in cell viability.

Using concentrations of $H_2O_2$ lower than 100 µM resulted in significant PS expression without any appreciable reduction in cell viability. For example, PS was detected at the cell surface of about 50% of cells in all $H_2O_2$ treated wells using $H_2O_2$ at concentrations as low as 20 µM. It is important to note that, under these low $H_2O_2$ concentrations, the cells remained firmly attached to the plastic and to each other, showed no morphological changes and had no signs of cytotoxicity. Detailed analyses revealed essentially 100% cell-cell contact, retention of proper cell shape and an intact cytoskeleton.

The 50% PS surface expression induced by low levels of $H_2O_2$ was thus observed in cell populations in which cell viability was identical to the control, untreated cells (i.e., 95%). The PS expression associated with high $H_2O_2$ concentrations was accompanied by cell damage, and the PS-positive cells exposed to over 100 µM $H_2O_2$ were detached, floating and had disrupted cytoskeletons.

The maintenance of cell viability in the presence of low concentrations $H_2O_2$ is consistent with data from other laboratories. For example, Schorer et al. (1985) showed that human umbilical vein endothelial cells (HUVEC) treated with 15 µM $H_2O_2$ averaged 90 to 95% viability (reported as 5% to 10% injury), whilst those exposed to 1500 µM $H_2O_2$ were only 0%–50% viable (50% to 100% injured).

The use of $H_2O_2$ to mimic the tumor environment in vitro is also appropriate in that the tumor environment is rich in inflammatory cells, such as macrophages, PMNs and granulocytes, which produce $H_2O_2$ and other reactive oxygen species. Although never before connected with stable tumor vascular markers, inflammatory cells are known to mediate endothelial cell injury by mechanisms involving reactive oxygen species that require the presence of $H_2O_2$ (Weiss et al., 1981; Yamada et al., 1981; Schorer et al., 1985). In fact, studies have shown that stimulation of PMNs in vitro produces concentrations of $H_2O_2$ sufficient to cause sublethal endothelial cell injury without causing cell death (measured by chromium release assays) or cellular detachment; and that these $H_2O_2$ concentrations are attainable locally in vivo (Schorer et al., 1985).

The present in vitro translocation data correlates with the earlier results showing that anti-PS antibodies localize specifically to tumor vascular endothelial cells in vivo, and do not bind to cells in normal tissues. The finding that in vivo-like concentrations of $H_2O_2$ induce PS translocation to the endothelial cell surface without disrupting cell integrity has important implications in addition to validating the original in vivo data and the inventors' therapeutic approaches.

Human, bovine and murine endothelial cells are all known to be PS-negative under normal conditions. Any previously documented PS expression has always been associated with cell damage and/or cell death. This is simply not the case in the present studies, where normal viability is maintained. This shows that PS translocation in tumor vascular endothelium is mediated by biochemical mechanisms unconnected to cell damage. This is believed to be the first demonstration of PS surface expression in morphologically intact endothelial cells and the first indication that PS expression can be disconnected from the apoptosis pathway (s). Returning to the operability of the present invention, these observations again confirm that PS is a sustainable, rather than transient, marker of tumor blood vessels and a suitable candidate for therapeutic intervention.

2. PS Expression does not Correlate with Cell Activation

The relevance of this in vitro data to the tumor environment is also strengthened by the fact that other, general cell activators are without effect on PS translocation in endothelial cells. For example, the inventors tested TNF in similarly controlled studies and found it unable to induce PS surface expression, despite the expected increases in E-selectin and VCAM expression. Likewise, LPS, bFGF, IL-1α and IL1β were all without effect on PS expression in appropriately controlled studies.

3. PS Induction by Thrombin

In contrast to the lack of effects of other cell activators, thrombin was observed to increase PS expression, although not to the same extent as $H_2O_2$. This data is also an integral part of the tumor-induction model of PS expression developed by the present inventors (thrombin-induced PS surface expression in normal tissues would also further coagulation as PS expression coordinates the assembly of coagulation initiation complexes (Ortel et al., 1992)).

The tumor environment is known to be prothrombotic, such that tumor vasculature is predisposed to coagulation (U.S. Pat. No. 5,877,289). As thrombin is a product of the coagulation cascade, it is present in tumor vasculature. In fact, the presence of thrombin induces VCAM expression, contributing to the inventors' ability to exploit VCAM as a targetable marker of tumor vasculature (U.S. Pat. Nos. 5,855,866; 5,877,289). The present data showing that thrombin also induces PS expression is thus both relevant to targeting aminophospholipids with naked antibodies and therapeutic conjugates, and further explains the beneficial effects of the anti-VCAM coaguligand containing Tissue Factor (Example VII).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abrams and Oldham, In: *Monoclonal Antibody Therapy of Human Cancer*, Foon and Morgan (Eds.), Martinus Nijhoff Publishing, Boston, pp. 103–120, 1985.

Antibodies: A Laboratory Manual, Cold Spring Harbor Laboratory, 1988.

Asahara, Chen, Takahashi, Fujikawa, Kearney, Magner, Yancopoulos, Isner, "Tie2 receptor ligands, angiopoietin-1 and angiopoietin-2, modulate VEGF-induced postnatal neovascularization" *Circ. Res.*, 83(3): 233–40, 1998.

Barbas, Kang, Lerner and Benkovic, "Assembly of combinatorial antibody libraries on phage surfaces: the gene III site," *Proc. Natl. Acad. Sci., USA*, 88(18):7978–7982, 1991.

Berard, Boffa, Karmochkine, Aillaud, Juhan-Vague, Frances, Cacoub, Piette and Harle, "Plasma reactivity to hexagonal II phase phosphatidylethanolamine is more frequently associated with lupus anticoagulant than with antiphosphatidylethanolamine antibodies," *J. Lab. Clin. Med*, 122(5):601–605, 1993.

Berman, Mellis, Pollock, Smith, Suh, Heinke, Kowal, Surti, Chess, Cantor, et al., "Content and organization of the human Ig VH locus: definition of three new VH families and linkage to the Ig CH locus," *EMBO J.*, 7(3):727–738, 1988.

Bevers, Comburius and Zwaal, "The nature of the binding site for prothrombinase at the platelet surface as revealed by lipolytic enzymes," *Eur. J. Biochem.*, 122:81–85, 1982.

Bevers, Comfurius and Zwaal, "Changes in membrane phospholipid distribution during platelet activation," *Biochim. Biophys. Acta*, 736:57–66, 1983.

Bevers, Rosing and Zwaal, "Development of procoagulant binding sites on the platelet surface," *Adv. Exp. Med. Biol.*, 192:359–371, 1985.

Bevers, Galli, Barbui, Comfurius and Zwaal, "Lupus anticoagulant IgG's (LA) are not directed to phospholipids only, but to a complex of lipid-bound human prothrombin," *Thromb. Haemost.*, 66(6):629–32, 1991.

Bevilacqua, "Endothelial-leukocyte adhesion molecules," *Ann. Rev. Immunol.*, 11:767–804, 1993.

Blankenberg, Katsikis, Tait, Davis, Naumovski, Ohtsuki, Kopiwoda, Abrams, Darkes, Robbins, Maecker and Strauss, "In vivo detection and imaging of phosphatidylserine expression during programmed cell death," *Proc. Natl. Acad. Sci., USA*, 95:6349–6354, 1998.

Bocci, "Efficient labeling of serum proteins with 131I using chloramine T," *Int. J. Appl. Radiat. Isot.*, 15:449–456, 1964.

Bombeli, Karsan, Tait and Harlan, "Apoptotic vascular endothelial cells become procoagulant," *Blood*, 89(7): 2429–2442, 1997.

Bordron, Dueymes, Levy, Jamin, Leroy, Piette, Schoenfeld and Youinou, "The binding of some human antiendothelial cell antibodies induces endothelial cell apoptosis," *J. Clin. Invest.*, 101(10):2029–2035, 1998.

Bornstein, "Thrombospondins: structure and regulation of expression," *FASEB J.*, 6(14):3290–3299, 1992.

Borrebaeck and Moller, "In vitro immunization. Effect of growth and differentiation factors on antigen-specific B cell activation and production of monoclonal antibodies to autologous antigens and weak immunogens," *J. Immunol.*, 136(10):3710–3715, 1986.

Bradford, "A rapid and sensitive method for the quantitation of microgram quantities of protein utilizing the principle of protein-dye binding," *Anal. Biochem.*, 72:248–254, 1976.

Branch, Rote, Dostal and Scott, "Association of lupus anticoagulant with antibody against phosphatidylserine," *Clin. Immun. Immunopathol.*, 42:63–75, 1987.

Brinkman, Mertens, Holthius, Zwart-Huinink, Grijm and Van Mourik, "The activation of human blood coagulation factor X on the surface of endothelial cells: a comparison with various vascular cells, platelets and monocytes," *Br. J. Haematol.*, 87:332–342, 1994.

Bruijn and Dinklo, "Distinct patterns of expression of intercellular adhesion molecule-1, vascular cell adhesion molecule-1, and endothelial-leukocyte adhesion molecule-1 in renal disease," *Lab. Invest.*, 69:329–335, 1993.

Burke et al., "Cloning of large segments of exogenous DNA into yeast by means of artificial chromosome vectors", *Science*, 236, 806–812, 1987.

Burrows, Watanabe and Thorpe, "A murine model for antibody-directed targeting of vascular endothelial cells in solid tumors," *Cancer Res.*, 52:5954–5962, 1992.

Burrows and Thorpe, "Eradication of large solid tumors in mice with an immunotoxin directed against tumor vasculature," *Proc. Natl. Acad. Sci. USA*, 90:8996–9000, 1993.

Bussolino, deRossi, Sica, Colotta, Wang, Bocchietto, Martin, Padura, Bosia, Dejana, and Mantovani, "Murine endothelial cell lines transformed by polyoma middle T oncogene as target for and producers of cytokines," *J. Immunol.*, 147:2122–2129, 1991.

Campbell, In: *Monoclonal Antibody Technology, Laboratory Techniques in Biochemistry and Molecular Biology*, Vol. 13, Burden and Von Knippenberg (Eds.), Elseview, Amsterdam, pp. 75–83, 1984.

Carnemolla et al., "A tumor-associated fibronectin isoform generated by alternative splicing of messenger RNA precursors," *J. Cell Biol.*, 108:1139–1148, 1989.

Chamley, McKay and Pattison, "Cofactor dependent and cofactor independent anticardiolipin antibodies," *Thromb. Res.*, 61(3):291–9, 1991.

Clapp et al., "The 16-kilodalton N-terminal fragment of human prolactin is a potent inhibitor of angiogenesis," *Endocrinology*, 133(3):1292–1299, 1993.

Connor, Bucana, Fidler and Schroit, "Differentiation-dependent expression of phosphatidylserine in mammalian plasma membranes: quantitative assessment of outer-leaflet lipid by prothrombinase complex formation," *Proc. Natl. Acad. Sci. USA*, 86(9):3184–3188, 1989.

Coughlin et al., "Interleukin-12 and interleukin-18 synergistically induce murine tumor regression which involves inhibition of angiogenesis," *J. Clin. Invest.*, 101(6): 1441–1452, 1998.

D'Amato et al., "Thalidomide is an inhibitor of angiogenesis," *Proc. Natl. Acad. Sci. USA*, 91(9): 4082–4085, 1994.

D'Angelo et al., "Activation of mitogen-activated protein kinases by vascular endothelial growth factor and basic fibroblast growth factor in capillary endothelial cells is inhibited by the antiangiogenic factor 16-kDa N-terminal fragment of prolactin," *Proc. Natl. Acad. Sci. USA*, 92(14): 6374–6378, 1995.

Dachary-Prigent, Toti, Satta, Pasquet, Uzan and Freyssinet, "Physiopathological significance of catalytic phospholipids in the generation of thrombin," *Seminars In Thrombosis and Hemostasis*, 22:157–164, 1996.

Davis and Yancopoulos, "The angiopoietins: Yin and Yang in angiogenesis", *Curr. Top. Microbiol. Immunol.*, 237:173–85, 1999.

de Jong, Geldwerth and Kuypers, "Oxidative damage does not alter membrane phospholipid asymmetry in human erythrocytes," *Am. Chem. Soc.*, 1997.

Denekamp, "Vascular attack as a therapeutic strategy for cancer," *Cancer Metastasis Rev.*, 9:267–282, 1990.

DeVore et al., "Phase I Study of the Antineovascularization Drug CM101," *Clin. Cancer Res.*, 3(3):365–372, 1997.

Diehl, Pfreundschuh, Fonatsch, Stein, Falk, Burrichter and Schaadt, "Phenotypic genotypic analysis of Hodgkin's disease derived cell lines: histopathological and clinical implications," *Cancer Surveys*, 4:399–416, 1985.

Donati, "Cancer and thrombosis: from Phlegmasia alba dolens to transgenic mice," *Thromb. Haemost.*, 74:278–281, 1995.

Drouvalakis and Buchanan, "Phospholipid specificity of autoimmune and drug induced lupus anticoagulants; association of phosphatidylethanolamine reactivity with thrombosis in autoimmune disease," *J. Rheumatol.*, 25(2): 290–295, 1998.

Droz, Patey, Paraf, Chretien and Gogusev, "Composition of extracellular matrix and distribution of cell adhesion molecules in renal cell tumors," *Lab. Invest.*, 71:710–718, 1994.

Dvorak, Nagy and Dvorak, "Structure of Solid Tumors and Their Vasculature: Implications for Therapy with Monoclonal Antibodies," *Cancer Cells*, 3(3):77–85, 1991.

Edgington, Mackman, Brand and Ruf, "The Structural Biology of Expression and Function of Tissue Factor," *Thromb. Haemost.*, 66(1):67–79, 1991.

Ferrara, Clapp, Weiner, "The 16K fragment of prolactin specifically inhibits basal or fibroblast growth factor stimulated growth of capillary endothelial cells," *Endocrinology*, 129(2):896–900, 1991.

Folkman et al., "Angiogenesis inhibition and tumor regression caused by heparin or a heparin fragment in the presence of cortisone," *Science*, 221:719–725, 1983.

Fotsis et al., "The endogenous oestrogen metabolite 2-methoxyoestradiol inhibits angiogenesis and suppresses tumour growth," *Nature*, 368(6468):237–239, 1994.

Flynn, Byrne, Baglin, Weissberg and Bennett, "Thrombin generation by apoptotic vascular smooth muscle cells," *Blood*, 89(12):4378–4384, 1997.

Frater-Schroder et al., "Tumor necrosis factor type alpha, a potent inhibitor of endothelial cell growth in vitro, is angiogenic in vivo," *Proc. Natl. Acad. Sci. USA*, 84(15): 5277–5281, 1987.

Frazier, "Thrombospondins," *Curr. Opin. Cell Biol.*, 3(5): 792–799, 1991.

Fries, Williams, Atkins, Newman, Lipscomb and Collins, "Expression of VCAM-1 and E-selectin in an in vivo model of endothelial activation," *Am. J. Pathol.*, 143:725–737, 1993.

Gaffet, Bettache and Bienvenüe, "Transverse redistribution of phospholipids during human platelet activation: evidence for a vectorial outflux specific to aminophospholipids," *Biochem.*, 34:6762–6769, 1995.

Gagliardi and Collins, "Inhibition of angiogenesis by antiestrogens," *Cancer Res.*, 53(3):533–535, 1993.

Gagliardi, Hadd, Collins, "Inhibition of angiogenesis by suramin," *Cancer Res.*, 52(18):5073–5075, 1992.

Gagliardi et al., "Antiangiogenic and antiproliferative activity of suramin analogues," *Cancer Chemother. Pharmacol.*, 41(2):117–124, 1998.

Galli, Comfurius, Maassen Hemker, de Baets, van Breda-Vriesman, Barbui, Zwaal and Bevers, "Anticardiolipin antibodies (ACA) directed not to cardiolipin but to a plasma protein cofactor," *Lancet*, 335(8705):1544–7, 1990.

Galli, Barbui, Zwaal, Comfurius and Bevers, "Antiphospholipid antibodies: involvement of protein cofactors," *Haematologica*, 78(1):1–4, 1993.

Ge and Butcher, "Cloning and expression of a cDNA encoding mouse endoglin, an endothelial cell TGF-beta ligand," *Gene*, 138:201–206, 1994.

Gefter et al., "A simple method for polyethylene glycol-promoted hybridization of mouse myeloma cells," *Somatic Cell Genet.*, 3:231–236, 1977.

Gibbons, "Mann-Whitney-Wilcoxon test for two independent samples," In: *Nonparametric methods for quantitative analysis*, J. D. Gibbons (ed.), Holt, Rinehart and Winston, New York, pp. 160, 1976.

Glennie, et al., "Preparation and performance of bispecific F(ab' gamma)2 antibody containing thioether-linked Fab' gamma fragments," *J. Immunol.*, 139:2367–2375, 1987.

Goding, In: *Monoclonal Antibodies: Principles and Practice*, 2nd Edition, Academic Press, Orlando, Fla., pp. 60–61, 65–66, 71–74, 1986.

Good et al., "A tumor suppressor-dependent inhibitor of angiogenesis is immunologically and functionally indistinguishable from a fragment of thrombospondin," *Proc. Natl. Acad. Sci. USA*, 87(17):6624–6628, 1990.

Grant et al., "Fibronectin fragments modulate human retinal capillary cell proliferation and migration," *Diabetes*, 47(8):1335–1340, 1998.

Hagemeier et al., "A Monoclonal Antibody Reacting with Endothelial Cells of Budding Vessels in Tumors and Inflammatory Tissues, and Non-Reactive with Normal Adult Tissues," *Int. J. Cancer*, 38:481–488, 1986.

Hahne, Jager, Isenmann, Hallmann and Vestweber, "Five tumor necrosis factor-inducible cell adhesion mechanisms on the surface of mouse endothelioma cells mediate the binding of leukocytes," *J. Cell Biol.*, 121:655–664, 1993.

Hampton, Vanags, Porn-Ares and Orrenius, "Involvement of extracellular calcium in phosphatidylserine exposure during apoptosis," *FEBS Lett.*, 399(3):277–282, 1996.

Haran et al., "Tamoxifen enhances cell death in implanted MCF7 breast cancer by inhibiting endothelium growth," *Cancer Res.*, 54(21):5511–5514, 1994.

Hasselaar and Sage, "SPARC antagonizes the effect of basic fibroblast growth factor on the migration of bovine aortic endothelial cells," *J. Cell Biochem.*, 49(3):272–283, 1992.

Hellerqvist et al., "Antitumor effects of GBS toxin: a polysaccharide exotoxin from group B beta-hemolytic streptococcus," *J. Cancer Res. Clin. Oncol.*, 120(1–2): 63–70, 1993.

Hiscox and Jiang, "Interleukin-12, an emerging anti-tumour cytokine," *In Vivo*, 11(2): 125–132, 1997.

Holash et al., "Vessel Cooption, Regression, and Growth in Tumors Mediated by Angiopoietins and VEGF", *Science*, 284:1994–1998, 1999.

Hori et al., "Differential effects of angiostatic steroids and dexamethasone on angiogenesis and cytokine levels in rat sponge implants," *Br. J. Pharmacol.*, 118(7):1584–1591, 1996.

Huang, Molema, King, Watkins, Edgington and Thorpe, "Tumor infarction in mice by antibody-directed targeting of tissue factor to tumor vasculature," *Science*, 275:547–550, 1997.

Huse, Sastry, Iverson, Kang, Alting-Mees, Burton, Benkovic and Lerner, *Science*, "Generation of a large combinatorial library of the immunoglobulin repertoire in phage lambda," 246(4935):1275–1281, 1989.

Igarashi, Umeda, Tokita, Soo Nam and Inoue, "Effective induction of anti-phospholipid and anticoagulant antibodies in normal mouse," *Thrombosis Res.*, 61:135–148, 1991.

Ingber et al., "Angioinhibins: Synthetic analogues of fumagillin which inhibit angiogenesis and suppress tumor growth," *Nature*, 48:555–557, 1990.

Iwamoto et al., "Inhibition of angiogenesis, tumour growth and experimental metastasis of human fibrosarcoma cells HT1080 by a multimeric form of the laminin sequence Tyr-Ile-Gly-Ser-Arg (YIGSR)," Br. J. Cancer, 73(5): 589–595, 1996.

Jackson et al., "Stimulation and inhibition of angiogenesis by placental proliferin and proliferin-related protein," Science, 266(5190):1581–1584, 1994.

Jamasbi, Wan and Stoner, "Epitope masking of rat esophageal carcinoma tumor-associated antigen by certain coexisting glycolipid and phospholipid molecules: a potential mechanism for tumor cell escape from the host immune responses," Cancer Immunol. Immunother., 38(2):99–106, 1994.

Jendraschak and Sage, "Regulation of angiogenesis by SPARC and angiostatin: implications for tumor cell biology," Semin. Cancer Biol., 7(3):139–146, 1996.

Jones, Dear, Foote, Neuberger and Winter, "Replacing the complementarity-determining regions in a human antibody with those from a mouse," Nature, 321(6069): 522–525, 1986.

Julien, Tournier and Tocanne, "Differences in the transbilayer and lateral motions of fluorescent analogs of phosphatidylcholine and phosphatidylethanolamine in the apical plasma membrane of bovine aortic endothelial cells," Exp. Cell. Res., 208(2):387–9, 1993.

Julien, Tournier and Tocanne, "Basic fibroblast growth factor modulates the aminophospholipid translocase activity present in the plasma membrane of bovine aortic endothelial cells," Eur. J. Biochem., 230:287–297, 1995.

Julien, Millot, Tocanne and Tournier, "12-O-Tetradecanoylphorbol-13-Acetate inhibits aminophospholipid translocase activity and modifies the lateral motions of fluorescent phospholipid analogs in the plasma membrane of bovine aortic endothelial cells," Experimental Cell Res., 234:125–131, 1997.

Kang, Barbas, Janda, Benkovic and Lemer, "Linkage of recognition and replication functions by assembling combinatorial antibody Fab libraries along phage surfaces," Proc. Natl. Acad. Sci., U.S.A, 88(10):4363–4366, 1991.

Katsuragawa, Kanzaki, Inoue, Hirano, Mori and Rote, "Monoclonal antibody against phosphatidylserine inhibits in vitro human trophoblastic hormone production and invasion," Biology of Reproduction, 56:50–58, 1997.

Kenyon, Browne, D'Amato, "Effects of thalidomide and related metabolites in a mouse corneal model of neovascularization," Exp. Eye Res., 64(6):971–978, 1997.

Kim, Kwak, Ahn, So, Liu, Koh, Koh, "Molecular cloning and characterization of a novel angiopoietin family protein, angiopoietin-3", FEBS Lett., 443(3):353–6, 1999.

Kleinman et al., "The laminins: a family of basement membrane glycoproteins important in cell differentiation and tumor metastases," Vitam. Horm., 47:161–186, 1993.

Kohler and Milstein, "Continuous cultures of fused cells secreting antibody of predefined specificity," Nature, 256:495–497, 1975.

Kohler and Milstein, "Derivation of specific antibody-producing tissue culture and tumor lines by cell fusion," Eur. J. Immunol., 6:511–519, 1976.

Konieczny, Bobrzecka, Laidler and Rybarska, "The combination of IgM subunits and proteolytic IgG fragment by controlled formation of interchain disulphides," Haematologia, 14(1):95–99, 1981.

Kuzu, Bicknell, Fletcher and Gatter, "Expression of adhesion molecules on the endothelium of normal tissue vessels and vascular tumors," Lab. Invest., 69(3): 322–328, 1993.

Lane, Iruela-Arispe, Sage, "Regulation of gene expression by SPARC during angiogenesis in vitro. Changes in fibronectin, thrombospondin-1, and plasminogen activator inhibitor-1," J. Biol. Chem., 267(23):16736–16745, 1992.

Lee et al., "Inhibition of urokinase activity by the antiangiogenic factor 16K prolactin: activation of plasminogen activator inhibitor 1 expression," Endocrinology, 139(9): 3696–3703, 1998.

Leppink, Bishop, Sedmak, Henry, Ferguson, Streeter, Butcher and Orosz, "Inducible expression of an endothelial cell antigen on murine myocardial vasculature in association with interstitial cellular infiltration," Transplantation, 48(5):874–877, 1989.

Levy, Gharavi, Sammaritano, Habina and Lockshin, "Fatty acid chain is a critical epitope for antiphospholipid antibody," J. Clin. Immunol., 10(3):141–145, 1990.

Lin, Shroyer, Walter, Lyden, Ng and Rote, "Monoclonal IgM antiphosphatidylserine antibody reacts against cytoskeleton-like structures in cultured human umbilical cord endothelial cells," Am. J. Reprod Immun., 33:97–107, 1995.

Lin, Buxton, Acheson, Radziejewski, Maisonpierre, Yancopoulos, Channon, Hale, Dewhirst, George, Peters, "Anti-angiogenic gene therapy targeting the endothelium-specific receptor tyrosine kinase Tie2", Proc. Natl. Acad. Sci., USA, 95(15):8829–34, 1998.

Lindner and Borden, "Effects of tamoxifen and interferon-beta or the combination on tumor-induced angiogenesis," Int. J. Cancer, 71(3):456–461, 1997.

Lingen, Polverini, Bouck, "Inhibition of squamous cell carcinoma angiogenesis by direct interaction of retinoic acid with endothelial cells," Lab. Invest., 74(2):476–483, 1996.

Lingen, Polverini, Bouck, "Retinoic acid and interferon alpha act synergistically as antiangiogenic and antitumor agents against human head and neck squamous cell carcinoma," Cancer Res., 58(23):5551–5558, 1998.

Liu, Moy, Kim, Xia, Rajasekaran, Navarro, Knudsen and Bander, "Monoclonal antibodies to the extracellular domain of prostate-specific membrane antigen also react with tumor vascular endothelium", Cancer Res., 57:3629–3634, 1997.

Majewski et al., "Vitamin D3 is a potent inhibitor of tumor cell-induced angiogenesis," J. Invest. Dermatol. Symp. Proc., 1(l):97–101, 1996.

Mandriota and Pepper, "Regulation of angiopoietin-2 mRNA levels in bovine microvascular endothelial cells by cytokines and hypoxia", Circ. Res., 83(8):852–9, 1998.

Maneta-Peyret, Bessoule, Geffard and Cassagne, "Demonstration of high specificity antibodies against phosphatidylserine," J. Immun. Meth., 108:123–127, 1988.

Maneta-Peyret, Freyburger, Bessoule and Cassagne, "Specific immunocytochemical visualization of phosphatidylserine," J. Immun. Methods, 122:155–159, 1989.

Manetti et al., "Synthesis and binding mode of heterocyclic analogues of suramin inhibiting the human basic fibroblast growth factor," Bioorg. Med. Chem., 6(7):947–958, 1998.

Martin, Reutelingsperger, McGahon, Rader, van Schie, LaFace and Green, "Early redistribution of plasma membrane phosphatidylserine is a general feature of apoptosis regardless of the initiating stimulus: inhibition by over-expression of Bcl–2 and Abl," J. Exp. Med., 182(5): 1545–1556, 1995.

Matsuura, Igarashi, Yasuda, Triplett and Koike, "Anticardiolipin antibodies recognize beta 2-glycoprotein I structure altered by interacting with an oxygen modified solid phase surface," *J. Exp. Med,* 179(2):457–62, 1994.

McNeil, Simpson, Chesterman and Krilis, "Antiphospholipid antibodies are directed against a complex antigen that includes a lipid-binding inhibitor of coagulation: beta 2-glycoprotein I (apolipoprotein H)," *Proc. Natl. Acad. Sci. USA,* 87(11):4120–4, 1990.

Mills, Brooker and Camerini-Otero, "Sequences of human immunoglobulin switch regions: implications for recombination and transcription," *Nucl. Acids Res.,* 18:7305–7316, 1990.

Miyake, Medina, Ishihara, Kimoto, Auerbach and Kincade, "VCAM-like adhesion molecule on murine bone marrow stromal cells mediates binding of lymphocyte precursors in culture," *J. Cell. Biol.,* 114:557–565, 1991.

Moldovan, Moldovan and Simionescu, "Binding of vascular anticoagulant alpha (annexin V) to the aortic intima of the hypercholesterolemic rabbit. An autoradiographic study," *Blood Coagul Fibrinolysis,* 5(6):921–928, 1994.

Montesano, Pepper, Mohle-Steinlein, Risau, Wagner and Orci, "Increased proteolytic activity is responsible for the aberrant morphogenetic behavior of endothelial cells expressing the middle T oncogene," *Cell,* 62:435–445, 1990.

Moore et al., "Tumor angiogenesis is regulated by CXC chemokines," *J. Lab. Clin. Med.,* 132(2):97–103, 1998.

Morrison, Johnson, Herzenberg and Oi, "Chimeric human antibody molecules: mouse antigen-binding domains with human constant region domains," *Proc. Natl. Acad. Sci. USA,* 81(21):6851–6855, 1984.

Morrison, Wims, Kobrin and Oi, "Production of novel immunoglobulin molecules by gene transfection," *Mt. Sinai J. Med.,* 53(3):175, 1986.

Morrissey, Fair and Edgington, "Monoclonal antibody analysis of purified and cell-associated tissue factor," *Thromb. Res.,* 52:247–261, 1988.

Müller, Pomorski, Müller, Zachowski and Herrmann, "Protein-dependent translocation of aminophospholipids and asymmetric transbilayer distribution of phospholipids in the plasma membrane of ram sperm cells," *Biochemistry,* 33:9968–9974, 1994.

Munro, "Endothelial-leukocyte adhesive interactions in inflammatory diseases," *European. Heart Journal,* 14:72–77, 1993.

Murphy, Joseph, Stephens and Horrocks, "Phospholipid composition of cultured human endothelial cells," *Lipids,* 27(s):150–153, 1992.

Murray, Clauss, Thurston and Stern, "Tumour-derived factors which induce endothelial tissue factor and enhance the procoagulant response to TNF," *Int. J. Radiat. Biol.,* 60(1–2):273–277, 1991.

Nagler, Feferman, Shoshan, "Reduction in basic fibroblast growth factor mediated angiogenesis in vivo by linomide," *Connect Tissue Res.,* 37(1–2):61–68, 1998.

Nakamura, Shidara, Kawaguchi, Azuma, Mitsuda, Onishi, Yamaji and Wada, "Lupus anticoagulant autoantibody induces apoptosis in umbilical vein endothelail cells: involvement of annexin V," *Biocehm. Biophys. Res. Comm.,* 205(2):1488–1493, 1994.

Nakamura, Ban, Yamaji, Yoneda and Wada, "Localization of the apoptosis-inducing activity of lupus anticoagulant in an annexin V-binding antibody subset," *J. Clin. Invest.,* 101(9):1951–1959, 1998.

Nawroth, Stern, Kisiel and Bach, "Cellular requirements for tissue factor generation by bovine aortic endothelial cells in culture," *Thromb. Res.,* 40:677–691, 1985.

Nawroth and Stern, "Modulation of endothelial cell hemostatic properties by tumor necrosis factor," *J. Exp. Med,* 163:740–745, 1986.

Nawroth, Handley, Matsueda, DeWaal, Gerlach, Blohm and Stem, "Tumor necrosis factor/cachectin-induced intravascular fibrin formation in meth A fibrosarcomas," *J. Exp. Med.,* 168:637–647, 1988.

Obringer, Rote and Walter, "Antiphospholipid antibody binding to bilayer-coated glass microspheres," *J. Immun. Methods,* 185:81–93, 1995.

Ogawa, Shreeniwas, Brett, Clauss, Furie and Stern, "The effect of hypoxia on capillary endothelial cell function: modulation of barrier and coagulant function," *J. Haematology,* 75:517–524, 1990.

Ohizumi, Tsunoda, Taniguchi, Saito, Esaki, Makimoto, Wakai, Tsutsumi, Nakagawa, Utoguchi, Kaiho, Ohsugi and Mayumi, "Antibody-based therapy targeting tumor vascular endothelial cells suppresses solid tumor growth in rats," *Biochem. Biophys. Res. Comm.,* 236:493–496, 1997.

Oikawa et al., "A highly potent antiangiogenic activity of retinoids," *Cancer Lett.,* 48(2):157–162, 1989.

O'Reilly et al., "Angiostatin: a novel angiogenesis inhibitor that mediates the suppression of metastases by a Lewis lung carcinoma," *Cell,* 79:315–328, 1994.

O'Reilly et al., "Endostatin: an endogenous inhibitor of angiogenesis and tumor growth," *Cell,* 88(2):277–285, 1997.

Ortel, Devore-Carter, Quinn-Allen and Kane, "Deletion analysis of recombinant human factor V. Evidence for a phosphatidylserine binding site in the second C-type domain," *J. Biol. Chem.,* 267:4189–4198, 1992.

Papapetropoulos, Garcia-Cardena, Dengler, Maisonpierre, Yancopoulos, Sessa, "Direct actions of angiopoietin-1 on human endothelium: evidence for network stabilization, cell survival, and interaction with other angiogenic growth factors", *Lab. Invest.,* 79(2):213–23, 1999.

Parmley and Smith, "Antibody-selectable filamentous fd phage vectors: affinity purification of target genes," *Gene,* 73(2):305–318, 1988.

Patey, Vazeux, Canioni, Potter, Gallatin and Brousse, "Intercellular adhesion molecule-3 on endothelial cells: Expression in tumors but not in inflammatory responses," *Am. J. Pathol.,* 148:465–472, 1996.

Pepper et al., "Leukemia inhibitory factor (LIF) inhibits angiogenesis in vitro," *J. Cell Sci.,* 108(Pt 1):73–83, 1995.

Qamar, Gharavi, Levy and Lockshin, "Lysophosphatidylethanolamine is the antigen to which apparent antibody to phosphatidylethanolamine binds," *J. Clin. Immunol.,* 10(4):200–203, 1990.

Qu, Conroy, Walker, Wooding and Lucy, "Phosphatidylserine-mediated adhesion of T-cells to endothelial cells," *J. Biochem.,* 317(Pt 2):343–346, 1996.

Quinn et al., CM101, a polysaccharide antitumor agent, does not inhibit wound healing in murine models," *J. Cancer Res. Clin. Oncol.,* 121(4):253–256, 1995.

Rao, Tait and Hoang, "Binding of annexin V to a human ovarian carcinoma cell line (OC-2008). Contrasting effects on cell surface factor VIIa/tissue factor activity and prothrombinase activity," *Thromb. Res.,* 67(5):517–531, 1992.

Rauch, Tannenbaum, Tannenbaum, Ramelson, Cullis, Tilcock, Hope and Janoff, "Human hybridoma lupus anticoagulants distinguish between lamellar and hexagonal phase lipid systems," *J. Biol. Chem.,* 261(21): 9672–9677, 1986.

Rauch and Janoff, "Phospholipid in the hexagonal II phase is immunogenic: evidence for immunorecognition of nonbilayer lipid phases in vivo," *Proc. Natl. Acad. Sci., USA,* 87(11):4112–4, 1990.

Ravanat, Archipoff, Beretz, Freund, Cazenave and Freyssinet, "Use of annexin-V to demonstrate the role of phosphatidylserine exposure in the maintenance of hemostatic balance by endothelial cells," *Biochem. J.,* 282:7–13, 1992.

RayChaudhury and D'Amore, "Endothelial cell regulation by transforming growth factor-beta," *J. Cell Biochem.,* 47(3):224–229, 1991.

Riechmann, Clark, Waldmann and Winter, "Reshaping human antibodies for therapy," *Nature,* 332(6162): 323–327, 1988.

Richer and Lo, "Introduction of human DNA into mouse eggs by injection of dissected human chromosome fragments", *Science* 245, 175–177, 1989.

Rote, Ng, Dostal-Johnson, Nicholson and Siekman, "Immunologic detection of phosphatidylserine externalization during thrombin-induced platelet activation," *Clin. Immunol. Immunopathol.,* 66:193–200, 1993.

Rote, Chang, Katsuragawa, Ng, Lyden and Mori, "Expression of phosphatidylserine-dependent antigens on the surface of differentiating Be Wo human choriocarcinoma cells," *Am. J. Reprod. Immun.,* 33:114–121, 1995.

Rote, "Antiphospholipid antibodies and recurrent pregnancy loss," *Am. J. Reprod Immun.,* 35:394–401, 1996.

Ruf and Edgington, "Structural biology of tissue factor, the initiator of thrombogenesis in vivo," *FASEB J.,* 8:385–390, 1994.

Ruf, Rehemtulla and Edgington, "Phospholipid-independent and -dependent interactions required for tissue factor receptor and cofactor function," *Biol. Chem.,* 266:2158–2166, 1991.

Sambrook, Fritsch and Maniatis, *Molecular Cloning: A Laboratory Manual,* 2nd Ed., Cold Spring Harbor Press, Cold Spring Harbor, N.Y., 1989.

Sakamoto et al., "Heparin plus cortisone acetate inhibit tumor growth by blocking endothelial cell proliferation," *Canc. J.,* 1:55–58, 1986.

Sang, "Complex role of matrix metalloproteinases in angiogenesis," *Cell Res.,* 8(3):171–177, 1998.

Schick, Kurica and Chacko, "Location of phosphatidylethanolamine and phosphatidylserine in the human platelet plasma membrane," *J. Clin. Invest.,* 57:1221–1226, 1976.

Schick, "The organization of aminophospholipids in human platelet membranes: selective changes induced by thrombin", *J. Lab. Clin. Med.,* 91(5):802–10, 1978.

Schorer, Rick, Swaim and Moldow, "Structural features of endotoxin required for stimulation of endothelial cell tissue factor production; exposure of preformed tissue factor after oxidant-mediated endothelial cell injury," *J. Lab. Clin. Med.,* 106:38–42, 1985.

Schuurmans Stekhoven, Tijmes, Umeda, Inoue and De Pont, "Monoclonal antibody to phosphatidylserine inhibits $Na^+$/$K^+$-ATPase activity," *Biochimica et Biophysica Acta,* 1194:155–165, 1994.

Sheibani and Frazier, "Thrombospondin 1 expression in transformed endothelial cells restores a normal phenotype and suppresses their tumorigenesis," *Proc. Natl. Acad. Sci. USA,* 92(15):6788–6792, 1995.

Sheu et al., "Inhibition of angiogenesis in vitro and in vivo: comparison of the relative activities of triflavin, an Arg-Gly-Asp-containing peptide and anti-alpha(v)beta3 integrin monoclonal antibody," *Biochim. Biophys. Acta,* 1336(3):445–454, 1997.

Shyu, Manor, Magner, Yancopoulos, Isner, "Direct intramuscular injection of plasmid DNA encoding angiopoietin-1 but not angiopoietin-2 augments revascularization in the rabbit ischemic hindlimb", *Circulation,* 98(19):2081–7, 1998.

Sideras, Mizuta, Kanamori, Suzuki, Okamoto, Kuze, Ohno, Doi, Fukuhara, Hassan, et al., "Production of sterile transcripts of C gamma genes in an IgM-producing human neoplastic B cell line that switches to IgG-producing cells," *Intl. Immunol.,* 1(6):631–642, 1989.

Sipos et al., "Inhibition of tumor angiogenesis," *Ann. NY Acad. Sci.,* 732:263–272, 1994.

Sluiter, Pietersma, Lamers and Koster, "Leukocyte adhesion molecules on the vascular endothelium: their role in the pathogenesis of cardiovascular disease and the mechanisms underlying their expression," *J. Cardiol. Pharmacol.,* 22:S37–S44, 1993.

Smirnov, Triplett, Comp, Esmon and Esmon, "On the role of phosphatidylethanolamine in the inhibition of activated protein C activity by antiphospholipid antibodies," *J. Clin. Invest.,* 95(1):309–16, 1995.

Soff et al., "Expression of plasminogen activator inhibitor type 1 by human prostate carcinoma cells inhibits primary tumor growth, tumor-associated angiogenesis, and metastasis to lung and liver in an athymic mouse model," *J. Clin. Invest.,* 96(6):2593–2600, 1995.

Staal-van den Brekel, Thunnissen, Buurman and Wouters, "Expression of E-selectin, intercellular adhesion molecule (ICAM)-1 and vascular cell adhesion molecule (VCAM)-1 in non-small-cell lung carcinoma," *Virchows Arch.,* 428:21–27, 1996.

Staub, Harris, Khamashta, Savidge, Chahade and Hughes, "Antibody to phosphatidylethanolamine in a patient with lupus anticoagulant and thrombosis," *Ann. Rheum. Dis.,* 48(2):166–169, 1989.

Stone, Ruf, Miles, Edgington and Wright, "Recombinant soluble human tissue factor secreted by *Saccharomyces cerevisiae* and refolded from *E. coli* inclusion bodies: glycosylation of mutants, activity, and physical characterization," *Biochem. J.,* 310(2):605–614, 1995.

Stout, Basse, Luhm, Weiss, Wiedmer and Sims, "Scott syndrome erythrocytes contain a membrane protein capable of mediating $Ca^{2+}$-dependent transbilayer migration of membrane phospholipids," *J. Clin. Invest.,* 99(9): 2232–8, 1997.

Stratmann, Risau, Plate, "Cell type-specific expression of angiopoietin-1 and angiopoietin-2 suggests a role in glioblastoma angiogenesis", *Am. J. Pathol.,* 153(5): 1333–9, 1998.

Sugi and McIntyre, "Autoantibodies to phosphatidylethanolamine (PE) recognize a kininogen-PE complex," *Blood,* 86(8):3083–3089, 1995.

Sugi and McIntyre, "Phosphatidylethanolamine induces specific conformational changes in the kininogens recognizable by antiphosphatidylethanolamine antibodies," *Thromb. Haemost.,* 76(3):354–360, 1996a.

Sugi and McIntyre, "Autoantibodies to kininogen-phosphatidylethanolamine complexes augment thrombin-induced platelet aggregation," *Thromb. Res.,* 84(2): 97–109, 1996b.

Sugimura, Donato, Kakar and Scully, "Annexin V as a probe of the contribution of anionic phospholipids to the procoagulant activity of tumor cell surfaces," *Blood Coagul. Fibrinolysis,* 5(3):365–373, 1994.

Tada et al., "Inhibition of tubular morphogenesis in human microvascular endothelial cells by co-culture with chondrocytes and involvement of transforming growth factor beta: a model for avascularity in human cartilage," *Biochim. Biophys. Acta,* 1201(2): 135–142, 1994.

Takano et al., "Suramin, an anticancer and angiosuppressive agent, inhibits endothelial cell binding of basic fibroblast growth factor, migration, proliferation, and induction of urokinase-type plasminogen activator," *Cancer Res.,* 54(10):2654–2660, 1994.

Tanaka et al., "Viral vector-mediated transduction of a modified platelet factor 4 cDNA inhibits angiogenesis and tumor growth," *Nat. Med.,* 3(4):437–442, 1997.

Tanaka, Mori, Sakamoto, Makuuchi, Sugimachi, Wands, "Biologic significance of angiopoietin -2 expression in human hepatocellular carcinoma", *J. Clin. Invest.,* 103(3): 341–5, 1999.

Thornhill, Kyan-Aung and Haskard, "IL-4 increases human endothelial cell adhesiveness for T cells but not for neutrophils," *J. Immunol.,* 144:3060–3065, 1990.

Thorpe et al., "Heparin-Steroid Conjugates: New Angiogenesis Inhibitors with Antitumor Activity in Mice," *Cancer Res.,* 53:3000–3007, 1993.

Tolsma et al., "Peptides derived from two separate domains of the matrix protein thrombospondin-1 have anti-angiogenic activity," *J. Cell Biol.,* 122(2):497–511, 1993.

Toti, Satta, Fressinaud, Meyer and Freyssinet, "Scott syndrome, characterized by impaired transmembrane migration of procoagulant phosphatidylserine and hemorrhagic complications, is an inherited disorder," *Blood,* 87(4):1409–1415, 1996.

Trudell, Ardies and Anderson, "Antibodies raised against trifluoroacetyl-protein adducts bind to N-trifluoroacetyl-phosphatidylethanolamine in hexagonal phase phospholipid micelies," *J. Pharmacol. Exp. Ther.,* 257(2): 657–662, 1991a.

Trudell J R, Ardies, Green and Allen, "Binding of anti-acetaldehyde IgG antibodies to hepatocytes with an acetaldehyde-phosphatidylethanolamine adduct on their surface," *Alcohol Clin. Exp. Res.,* 15(2):295–299, 1991b.

Tryggvason, "The laminin family," *Curr. Opin. Cell Biol.,* 5(5):877–882, 1993.

Umeda, Igarashi, Nam and Inoue, "Effective production of monoclonal antibodies against phosphatidylserine: Stereo-specific recognition of phosphatidylserine by monoclonal antibody," *J. Immun.,* 143(7):2273–2279, 1989.

Utsugi, Schroit, Connor, Bucana and Fidler, "Elevated expression of phosphatidylserine in the outer membrane leaflet of human tumor cells and recognition by activated human blood monocytes," *Cancer Res.,* 51(11): 3062–3066, 1991.

Valenzuela, Griffiths, Rojas, Aldrich, Jones, Zhou, McClain, Copeland, Gilbert, Jenkins, Huang, Papadopoulos, Maisonpierre, Davis, Yancopoulos, "Angiopoietins 3 and 4: diverging gene counterparts in mice and humans", *Proc. Natl. Acad. Sci., USA,* 96(5):1904–9, 1999.

van Dijk, Wamaar, van Eendenburg, Thienpont, Braakman, Boot, Fleuren and Bolhuis, "Induction of tumor-cell lysis by bi-specific monoclonal antibodies recognizing renal-cell carcinoma and CD3 antigen," *Int. J. Cancer,* 43:344–349, 1989.

Van Heerde, Poort, van T Veer, Reutelingsperger and de Groot, "Binding of recombinant annexin V to endothelial cells: effect of annexin V binding on endothelial-cell-mediated thrombin formation," *J. Biochem.,* 302:305–312, 1994.

Vermes, Haanes, Steffens-Nakken and Reutelingsperger, "A novel assay for apoptosis. Flow cytometric detection of phosphatidylserine expression on early apoptotic cells using fluorescein labeled Annexin V," *J. Immunol. Methods,* 184(1):39–51, 1995.

Vitetta et al., "Phase I immunotoxin trial in patients with B-cell lymphoma," *Cancer Res.,* 15:4052–4058, 1991.

Vlachoyiannopoulos, Beigbeder, Duelanes, Youinou, Hunt, Krilis and Moutsopoulos, "Antibodies to phosphatidylethanolamine in antiphospholipid syndrome and systemic lupus erythematosus: their correlation with anticardiolipin antibodies and beta 2 glycoprotein-I plasma levels," *Autoimmunity,* 16(4):245–249, 1993.

Vogt, Ng and Rote, "A model for the antiphospholipid antibody syndrome: Monoclonal antiphosphatidylserine antibody induces intrauterine growth restriction in mice," *Am. J. Obstet. Gynecol.,* 174:700–707, 1996.

Vogt, Ng and Rote, "Antiphosphatidylserine antibody removes Annexin V and facilitates the binding prothrombin at the surface of a choriocarcinoma model of trophoblast differentiation," *Am. J. Obstet. Gynecol.,* 177:964–972, 1997.

Volpert, Lawler, Bouck, "A human fibrosarcoma inhibits systemic angiogenesis and the growth of experimental metastases via thrombospondin-1," *Proc. Natl. Acad. Sci. USA,* 95(11):6343–6348, 1998.

Vukanovic et al., "Antiangiogenic effects of the quinoline-3-carboxamide linomide," *Cancer Res.,* 53(8): 1833–1837, 1993.

Waltenberger et al., "Suramin is a potent inhibitor of vascular endothelial growth factor. A contribution to the molecular basis of its antiangiogenic action," *J. Mol. Cell Cardiol.,* 28(7):1523–1529, 1996.

Wamil et al., "Soluble E-selectin in cancer patients as a marker of the therapeutic efficacy of CM101, a tumor-inhibiting anti-neovascularization agent, evaluated in phase I clinical trail," *J. Cancer Res. Clin. Oncol.,* 123 (3):173–179, 1997.

Wells, "Starving cancer into submission" *Chem. Biol.,* 5(4): R87–88, 1998.

Weiss, Young, LoBuglio, Slivka and Nimeh, "Role of Hydrogen Peroxide in Neutrophil-Mediated Destruction of Cultured Endothelial Cells," *J. Clin. Invest.,* 68:714–721, 1981.

White, Handler, Smith, Hill and Lehman, In: *Principles of Biochemistry,* 6th Edition, McGraw-Hill, Inc. New York, Chapter 3 and pp 48–54, 1978.

Williamson and Schlegel, "Back and forth: the regulation and function of transbilayer phospholipid movement in eukaryotic cells," *Molec. Mem. Biol.,* 11:199–216, 1994.

Winter and Milstein, "Man-made antibodies," *Nature,* 349:293–299, 1991.

Wolff et al., "Dexamethasone inhibits glioma-induced formation of capillary like structures in vitro and angiogenesis in vivo," *Klin. Padiatr.,* 209(4):275–277, 1997.

Yamada, Moldow, Sacks, Craddock, Boogaens and Jacob, "Deleterious Effects of Endotoxin on Cultured Endothelial Cells: An in vitro Model of Vascular injury," *Inflammation,* 5:115–116, 1981.

Yamamura et al., "Effect of Matrigel and laminin peptide YIGSR on tumor growth and metastasis," *Semin. Cancer Biol.,* 4(4):259–265, 1993.

Yoon et al., "Inhibitory effect of Korean mistletoe (Viscum album coloratum) extract on tumour angiogenesis and metastasis of haematogenous and non-haematogenous tumour cells in mice," *Cancer Lett,* 97(1):83–91, 1995.

Yoshida et al., "Suppression of hepatoma growth and angiogenesis by a fumagillin derivative TNP470: possible involvement of nitric oxide synthase," *Cancer Res.,* 58(16):3751–3756, 1998.

Zacharski, Memoli, Ornstein, Rousseau, Kisiel and Kudryk, "Tumor cell procoagulant and urokinase expression in carcinoma of the ovary," *J. Natl. Cancer Inst.*, 85:1225–1230, 1993.

Zhao, Zhou, Wiedmer and Sims, "Level of expression of phospholipid scramblase regulates induced movement of phosphatidylserine to the cell surface," *J. Biol. Chem.*, 273:6603–6606, 1998.

Zhou, Zhao, Stout, Luhm, Wiedmer and Sims, "Molecular cloning of human plasma membrane phospholipid scramblase. A protein mediating transbilayer movement of plasma membrane phospholipids," *J. Biol. Chem.*, 272 (29): 18240–4, 1997.

Ziche et al., "Linomide blocks angiogenesis by breast carcinoma vascular endothelial growth factor transfectants," *Br. J. Cancer*, 77(7):1123–1129, 1998.

Zwaal, Bevers, Comfurius, Rosing, Tilly and Verhallen, "Loss of membrane phospholipid asymmetry during activation of blood platelets and sickled red cells; mechanisms and physiological significance," *Mol. Cell. Biochem.*, 91:23–31, 1989.

Zwaal, Comfurius and Bevers, "Platelet procoagulant activity and microvesicle formation. Its putative role in hemostasis and thrombosis," *Biochimica et Biophysica Acta*, 1180:1–8, 1992.

What is claimed is:

1. A method for killing tumor vascular endothelial cells, comprising administering to an animal having a vascularized tumor at least a first antibody, or antigen-binding region thereof, that binds to an aminophospholipid on the luminal surface of tumor vascular endothelial cells in an amount effective to kill said tumor vascular endothelial cells.

2. A method for inducing coagulation in tumor vasculature, comprising administering to an animal having a vascularized tumor a vessel-occluding amount of at least a first antibody, or antigen-binding region thereof, that binds to an aminophospholipid on the luminal surface of tumor vasculature.

3. A method for treating an animal having a vascularized tumor, comprising administering to said animal a tumor-destructive amount of at least a first antibody, or antigen-binding region thereof, that binds to an aminophospholipid on the luminal surface of tumor vasculature.

4. A method for treating an animal having a vascularized tumor, comprising administering to said animal a therapeutically effective amount of at least a first pharmaceutical composition comprising at least a first antibody, or antigen-binding fragment thereof, that binds to an aminophospholipid on the luminal surface of blood vessels of the vascularized tumor.

5. The method of claim 4, wherein said pharmaceutical composition comprises at least a first antibody, or antigen-binding fragment thereof, that binds to phosphatidylethanolamine on the luminal surface of blood vessels of the vascularized tumor.

6. The method of claim 4, wherein said pharmaceutical composition comprises at least a first antibody, or antigen-binding fragment thereof, that binds to phosphatidylserine on the luminal surface of blood vessels of the vascularized tumor.

7. The method of claim 4, wherein said pharmaceutical composition comprises at least a first IgG or IgM anti-aminophospholipid antibody.

8. The method of claim 4, wherein said pharmaceutical composition comprises at least a first scFv, Fv, Fab', Fab or F(ab')$_2$ antigen-binding fragment of an anti-aminophospholipid antibody.

9. The method of claim 4, wherein said pharmaceutical composition comprises at least a first human, humanized or part-human chimeric anti-aminophospholipid antibody or antigen-binding fragment thereof.

10. The method of claim 4, wherein said pharmaceutical composition comprises at least a first anti-aminophospholipid monoclonal antibody or antigen-binding fragment thereof.

11. The method of claim 10, wherein said pharmaceutical composition comprises at least a first anti-aminophospholipid monoclonal antibody, or antigen-binding fragment thereof, that is prepared by a preparative process comprising:

(a) preparing an anti-aminophospholipid antibody-producing cell; and (b) obtaining an anti-aminophospholipid monoclonal antibody from said antibody-producing cell.

12. The method of claim 11, wherein said anti-aminophospholipid antibody-producing cell is obtained from a human patient having a disease associated with the production of anti-aminophospholipid antibodies.

13. The method of claim 11, wherein said anti-aminophospholipid antibody-producing cell is obtained by stimulating a mixed population of human peripheral blood lymphocytes with an immunogenically effective amount of an aminophospholipid sample.

14. The method of claim 11, wherein said anti-aminophospholipid antibody-producing cell is obtained by immunizing an animal with an immunogenically effective amount of an aminophospholipid sample.

15. The method of claim 14, wherein said anti-aminophospholipid antibody-producing cell is obtained by immunizing a transgenic mouse that comprises a human antibody library with an immunogenically effective amount of an aminophospholipid sample.

16. The method of claim 11, wherein said preparative process comprises:

(a) fusing said anti-aminophospholipid antibody-producing cell with an immortal cell to prepare a hybridoma that produces an anti-aminophospholipid monoclonal antibody; and (b) obtaining an anti-aminophospholipid monoclonal antibody from said hybridoma.

17. The method of claim 11, wherein said preparative process comprises:

(a) immunizing an animal with an immunogenically effective amount of an aminophospholipid sample;

(b) preparing a collection of antibody-producing hybridomas from the immunized animal;

(c) selecting from the collection a hybridoma that produces an anti-aminophospholipid antibody; and (d) culturing the selected hybridoma to provide the anti-aminophospholipid monoclonal antibody.

18. The method of claim 17, wherein an antigen-binding region of the anti-aminophospholipid monoclonal antibody is operatively attached to a human antibody framework or constant region.

19. The method of claim 17, wherein the immunized animal is a transgenic mouse that comprises a human antibody library and wherein the anti-aminophospholipid monoclonal antibody is a human monoclonal antibody.

20. The method of claim 11, wherein said preparative process comprises:

(a) obtaining anti-aminophospholipid antibody-encoding nucleic acids from said anti-aminophospholipid antibody-producing cell; and (b) expressing said nucleic acids to obtain a recombinant anti-aminophospholipid monoclonal antibody.

21. The method of claim 11, wherein said preparative process comprises:
(a) immunizing an animal with an immunogenically effective amount of an aminophospholipid sample;
(b) preparing a combinatorial immunoglobulin phagemid library expressing RNA isolated from the spleen of the immunized animal;
(c) selecting from the phagemid library a clone that expresses an anti-aminophospholipid antibody; and
(d) expressing an anti-aminophospholipid antibody-encoding nucleic acid from said selected clone to provide a recombinant anti-aminophospholipid monoclonal antibody.

22. The method of claim 21, wherein the immunized animal is a transgenic mouse that comprises a human antibody library and wherein the recombinant anti-aminophospholipid monoclonal antibody is a recombinant human monoclonal antibody.

23. The method of claim 4, wherein said pharmaceutical composition comprises a dimer, trimer or multimer of an anti-aminophospholipid antibody or antigen-binding fragments thereof.

24. The method of claim 4, wherein at least a second antibody that binds to an aminophospholipid, or an antigen-binding fragment thereof, is administered to said animal.

25. The method of claim 4, wherein said pharmaceutical composition is administered to said animal via intravenous administration.

26. The method of claim 4, wherein an image of the vasculature of said vascularized tumor is first obtained by administering to said animal a diagnostically effective amount of a detectably-labeled antibody, or antigen-binding fragment thereof, that binds to and identifies an aminophospholipid on the luminal surface of blood vessels of the vascularized tumor.

27. The method of claim 4, further comprising subjecting said animal to surgery or radiotherapy.

28. The method of claim 4, further comprising simultaneously or sequentially administering to said animal a therapeutically effective amount of at least a second anti-cancer agent.

29. The method of claim 28, wherein said at least a second anti-cancer agent is a chemotherapeutic, radiotherapeutic, anti-angiogenic or apoptosis-inducing agent.

30. The method of claim 28, wherein said at least a second anti-cancer agent is an antibody-therapeutic agent construct comprising a targeting antibody, or antigen-binding fragment thereof, that binds to a surface-expressed, surface-accessible or surface-localized component of a tumor cell, tumor stroma or tumor vasculature; said targeting antibody or fragment thereof operatively linked to a therapeutic agent.

31. The method of claim 30, wherein said targeting antibody, or antigen-binding fragment thereof, binds to a cell surface antigen of a tumor cell.

32. The method of claim 30, wherein said targeting antibody, or antigen-binding fragment thereof, binds to a component of tumor stroma.

33. The method of claim 30, wherein said targeting antibody, or antigen-binding fragment thereof, binds to a surface-expressed, surface-accessible, surface-localized, cytokine-inducible or coagulant-inducible component of intratumoral blood vessels of a vascularized tumor.

34. The method of claim 33, wherein said targeting antibody, or antigen-binding fragment thereof, binds to a surface-expressed component of intratumoral vasculature selected from the group consisting of an aminophospholipid, endoglin, a TGFβ receptor, E-selectin, P-selectin, VCAM-1, ICAM-1, PSMA, a VEGF/VPF receptor, an FGF receptor, a TIE, $\alpha_v\beta_3$ integrin, pleiotropin, endosialin and an MHC Class II protein.

35. The method of claim 33, wherein said targeting antibody, or antigen-binding fragment thereof, binds to a surface-localized component of intratumoral vasculature selected from the group consisting of VEGF/VPF, FGF, TGFβ, a ligand that binds to a TIE, a tumor-associated fibronectin isoform, scatter factor/hepatocyte growth factor (HGF), platelet factor 4 (PF4), PDGF and TIMP.

36. The method of claim 30, wherein said targeting antibody, or antigen-binding fragment thereof, is operatively linked to a cytotoxic agent.

37. The method of claim 36, wherein said targeting antibody, or antigen-binding fragment thereof, is operatively linked to a plant-, fungus- or bacteria-derived toxin.

38. The method of claim 37, wherein said targeting antibody, or antigen-binding fragment thereof, is operatively linked to deglycosylated ricin A chain.

39. The method of claim 30, wherein said targeting antibody, or antigen-binding fragment thereof, is operatively linked to a coagulation factor or to an antibody, or antigen-binding fragment thereof, that binds to a coagulation factor.

40. The method of claim 39, wherein said targeting antibody, or antigen-binding fragment thereof, is operatively linked to Tissue Factor, truncated Tissue Factor or a derivative thereof, or to an antibody, or antigen-binding fragment thereof, that binds to Tissue Factor, truncated Tissue Factor or a derivative thereof.

41. The method of claim 4, wherein said animal is a human patient.

42. A method for treating cancer, comprising administering to an animal having a vascularized tumor a therapeutically effective amount of at least a first pharmaceutical composition comprising at least a first naked antibody, or antigen-binding fragment thereof, that binds to an aminophospholipid on the luminal surface of intratumoral blood vessels of the vascularized tumor.

43. A method for treating cancer, comprising administering to an animal having a vascularized tumor at least a first pharmaceutical composition comprising an amount of at least a first unconjugated antibody effective to kill at least a portion of the tumor or tumor vasculature; wherein said first unconjugated antibody is an unconjugated antibody, or antigen-binding fragment thereof, that binds to an aminophospholipid expressed on the luminal surface of tumor vascular endothelial cells.

44. A method for treating cancer, comprising administering to an animal having a vascularized tumor at least a first pharmaceutical composition comprising an amount of at least a first unconjugated antibody effective to occlude or destroy tumor blood vessels, as opposed to normal blood vessels; wherein said first unconjugated antibody is an unconjugated antibody, or antigen-binding fragment thereof, that binds to an aminophospholipid expressed on the luminal surface of tumor vascular endothelial cells.

45. A method for treating cancer, comprising administering to an animal having a vascularized tumor at least a first pharmaceutical composition comprising an amount of at least a first unconjugated antibody effective to induce tumor necrosis; wherein said first unconjugated antibody is an unconjugated antibody, or antigen-binding fragment thereof, that binds to an aminophospholipid expressed on the luminal surface of blood vessels of the vascularized tumor.

46. A method for treating cancer, comprising:
(a) forming an image of a vascularized tumor by administering to an animal having a vascularized tumor a diagnostically effective amount of a detectably-labeled antibody, or antigen-binding fragment thereof, that binds to an aminophospholipid on the luminal surface of blood vessels of the vascularized tumor, thereby forming a detectable image of the tumor vasculature; and
(b) subsequently administering to said animal a therapeutically effective amount of at least a first antibody, or antigen-binding fragment thereof, that binds to an aminophospholipid on the tumor blood vessel luminal surface and thereby destroys the tumor vasculature.

47. A method for treating cancer, comprising simultaneously or sequentially administering to an animal having a vascularized tumor a therapeutically effective combination of an unconjugated antibody, or antigen-binding fragment thereof, that binds to an aminophospholipid on the luminal surface of blood vessels of the vascularized tumor and at least a second anti-cancer agent.

48. The method of claim 47, wherein said at least a second anti-cancer agent is a chemotherapeutic, radiotherapeutic, anti-angiogenic or apoptosis-inducing agent or an antibody-therapeutic agent construct comprising a therapeutic agent operatively attached to an antibody, or antigen-binding fragment thereof, that binds to a surface-expressed, surface-accessible, surface-localized, cytokine-inducible or coagulant-inducible component of tumor vasculature or tumor stroma.

49. A method for inducing cell death in tumor vascular endothelial cells, comprising administering to an animal having a vascularized tumor at least a first antibody, or antigen-binding region thereof, that binds to an aminophospholipid on the luminal surface of tumor vascular endothelial cells in an amount effective to induce cell death in tumor vascular endothelial cells.

50. A method for treating an animal having a vascularized tumor, comprising administering to said animal at least a first antibody, or antigen-binding region thereof, that binds to an aminophospholipid on the luminal surface of tumor blood vessels in an amount effective to destroy or occlude at least a portion of said tumor blood vessels upon binding to said aminophospholipid.

51. A method for killing tumor vascular endothelial cells, comprising administering to an animal having a vascularized tumor at least a first antibody that binds to an aminophospholipid on the luminal surface of tumor vascular endothelial cells in an amount effective to kill said tumor vascular endothelial cells.

52. A method for inducing coagulation in tumor vasculature, comprising administering to an animal having a vascularized tumor a vessel-occluding amount of at least a first antibody that binds to an aminophospholipid on the luminal surface of tumor vasculature.

53. A method for treating an animal having a vascularized tumor, comprising administering to said animal a tumor-destructive amount of at least a first antibody that binds to an aminophospholipid on the luminal surface of tumor vasculature.

54. A method for treating an animal having a vascularized tumor, comprising administering to said animal a therapeutically effective amount of at least a first pharmaceutical composition comprising at least a first antibody that binds to an aminophospholipid on the luminal surface of blood vessels of the vascularized tumor.

55. The method of claim 54, wherein said pharmaceutical composition comprises at least a first antibody that binds to phosphatidylserine on the luminal surface of blood vessels of the vascularized tumor.

56. The method of claim 54, wherein said animal is a human patient.

57. A method for treating cancer, comprising administering to an animal having a vascularized tumor a therapeutically effective amount of at least a first pharmaceutical composition comprising at least a first naked antibody that binds to an aminophospholipid on the luminal surface of intratumoral blood vessels of the vascularized tumor.

58. A method for treating cancer, comprising administering to an animal having a vascularized tumor at least a first pharmaceutical composition comprising an amount of at least a first unconjugated antibody effective to kill at least a portion of the tumor or tumor vasculature; wherein said first unconjugated antibody binds to an aminophospholipid expressed on the luminal surface of tumor vascular endothelial cells.

59. A method for treating cancer, comprising administering to an animal having a vascularized tumor at least a first pharmaceutical composition comprising an amount of at least a first unconjugated antibody effective to occlude or destroy tumor blood vessels, as opposed to normal blood vessels; wherein said first unconjugated antibody binds to an aminophospholipid expressed on the luminal surface of tumor vascular endothelial cells.

60. A method for treating cancer, comprising administering to an animal having a vascularized tumor at least a first pharmaceutical composition comprising an amount of at least a first unconjugated antibody effective to induce tumor necrosis; wherein said first unconjugated antibody is an unconjugated antibody that binds to an aminophospholipid expressed on the luminal surface of blood vessels of the vascularized tumor.

61. A method for treating cancer, comprising simultaneously or sequentially administering to an animal having a vascularized tumor a therapeutically effective combination of an unconjugated antibody that binds to an aminophospholipid on the luminal surface of blood vessels of the vascularized tumor and at least a second anti-cancer agent.

62. A method for inducing cell death in tumor vascular endothelial cells, comprising administering to an animal having a vascularized tumor at least a first antibody that binds to an aminophospholipid on the luminal surface of tumor vascular endothelial cells in an amount effective to induce cell death in tumor vascular endothelial cells.

63. A method for treating an animal having a vascularized tumor, comprising administering to said animal at least a first antibody that binds to an aminophospholipid on the luminal surface of tumor blood vessels in an amount effective to destroy or occlude at least a portion of said tumor blood vessels upon binding to said aminophospholipid.

* * * * *